(12) United States Patent
Pregibon et al.

(10) Patent No.: US 8,609,337 B2
(45) Date of Patent: Dec. 17, 2013

(54) NUCLEIC ACID DETECTION AND QUANTIFICATION BY POST-HYBRIDIZATION LABELING AND UNIVERSAL ENCODING

(75) Inventors: Daniel C. Pregibon, Cambridge, MA (US); Isaac Stoner, Cambridge, MA (US); Andreas Windemuth, Belmont, MA (US); Timothy Erps, Salem, MA (US)

(73) Assignee: Firefly BioWorks, Inc., Cambridge, MA (US)

( * ) Notice: Subject to any disclaimer, the term of this patent is extended or adjusted under 35 U.S.C. 154(b) by 0 days.

(21) Appl. No.: 13/568,884

(22) Filed: Aug. 7, 2012

(65) Prior Publication Data

US 2012/0309651 A1 Dec. 6, 2012

Related U.S. Application Data

(63) Continuation of application No. PCT/US2011/039531, filed on Jun. 7, 2011.

(60) Provisional application No. 61/352,018, filed on Jun. 7, 2010, provisional application No. 61/365,738, filed on Jul. 19, 2010, provisional application No. 61/387,958, filed on Sep. 29, 2010.

(51) Int. Cl.
*C12M 1/00* (2006.01)
*C40B 30/10* (2006.01)
*C07H 21/04* (2006.01)

(52) U.S. Cl.
USPC ........ 435/6.1; 453/238.1; 453/287.2; 506/12; 536/23.1

(58) Field of Classification Search
None
See application file for complete search history.

(56) References Cited

U.S. PATENT DOCUMENTS

| | | | |
|---|---|---|---|
| 5,876,924 | A | 3/1999 | Zhang et al. |
| 5,945,526 | A | 8/1999 | Lee et al. |
| 6,251,303 | B1 | 6/2001 | Bawendi et al. |
| 6,319,426 | B1 | 11/2001 | Bawendi et al. |
| 6,322,901 | B1 | 11/2001 | Bawendi et al. |
| 6,423,551 | B1 | 7/2002 | Weiss et al. |
| 6,426,513 | B1 | 7/2002 | Bawendi et al. |
| 6,444,143 | B2 | 9/2002 | Bawendi et al. |
| 6,576,291 | B2 | 6/2003 | Bawendi et al. |
| 6,649,138 | B2 | 11/2003 | Adams et al. |
| 6,815,064 | B2 | 11/2004 | Treadway et al. |
| 7,319,003 | B2 | 1/2008 | Cantor et al. |

(Continued)

FOREIGN PATENT DOCUMENTS

| | | |
|---|---|---|
| JP | 11 118819 A | 4/1999 |
| WO | WO-2007/071062 A1 | 6/2007 |
| WO | WO-2009/002225 A2 | 12/2008 |
| WO | WO-2009/021923 A1 | 2/2009 |

OTHER PUBLICATIONS

Albretsen et al., Applications of Magnetic Beads with Covalently Attached Oligonucleotides in Hybridization, Anal. Biochem., 189; 40-50 (1990).

(Continued)

*Primary Examiner* — Betty Forman
(74) *Attorney, Agent, or Firm* — Choate Hall & Stewart LLP

(57) ABSTRACT

The present invention provides, among other things, methods and compositions for encoding a substrate for detecting and quantifying target nucleic acids.

22 Claims, 36 Drawing Sheets

(56) References Cited

U.S. PATENT DOCUMENTS

| | | | |
|---|---|---|---|
| 7,709,544 | B2 | 5/2010 | Doyle et al. |
| 7,947,487 | B2 | 5/2011 | Doyle et al. |
| 2002/0197614 | A1 | 12/2002 | Weir et al. |
| 2003/0049629 | A1 | 3/2003 | Edman et al. |
| 2003/0108900 | A1 | 6/2003 | Oliphant et al. |
| 2005/0214825 | A1 | 9/2005 | Stuelpnagel |
| 2005/0233318 | A1* | 10/2005 | Chee et al. ............... 435/6 |
| 2006/0228735 | A1* | 10/2006 | Bobrow et al. ............ 435/6 |
| 2008/0176216 | A1 | 7/2008 | Doyle et al. |
| 2008/0182239 | A1 | 7/2008 | Mullinax et al. |

OTHER PUBLICATIONS

Bullard et al., Direct comparison of nick-joining activity of the nucleic acid ligases from bacteriophage T4, Biochem J, 398; 135-144 (2006).

Chapain et al., High-throughput flow alignment of barcoded hydrogel microparticles, Lab Chip, 9; 3100-3109 (2009).

Ghosh et al., Covalent attachments of oligonucleotides to solid supports, Nucleic Acids Research, 15; 5353-5372 (1987).

Ju et al., Fluorescence energy transfer dye-labeled primers for DNA sequencing and analysis, Proc. Nat'l Acad. Sci., 92; 4347 (1995).

Lund et al., Assessment of methods for covalent binding of nucleic acids to magnetic beads, DynabeadsTM and the characteristics of the bound nucletic acids in hybridization reactions, Nucleic Acids Research, 16; 10861-10880 (1988).

Pregibon et al., Optimization of Encoded Hydrogel Particles for Nucleic Acid Quantification, Anal. Chem., 81; 4873-4881 (2009).

Stears et al., A novel, sensitive detection system for high-density microarrays using dendrimer technology, Physiol Genomics, 3; 93-99, 2000.

Wolf et al., Rapid hybridization kinetics of DNA attached to submicron latex particles, Nucleic Acids Research, 15; 2911-2926 (1987).

Zhu et al., High-Sensitivity Capillary Electrophoresis of Double-Stranded DNA Fragments Using Monomeric and Dimeric Fluorescent Intercalating Dyes, Anal. Chem., 66; 1941-1948 (1994).

International Search Report of PCT/US2011/039529, dated Feb. 9, 2012, 3 pages.

Written Opinion of PCT/US2011/039529, dated Feb. 9, 2012, 5 pages.

International Search Report of PCT/US11/39531, dated Feb. 23, 2012, 6 pages.

Written Opinion of PCT/US11/39531, dated Feb. 23, 2012, 8 pages.

Bong et al., Magnetic Barcoded Hydrogel Microparticles for Multiplexed Detection, Langmuir, 26(11); 8008-8014 (2010).

Hall et al., Integrons found in different locations have identical 5' ends but variable 3' ends, Journal of Bacteriology, 179: 6286-6294 (1994).

* cited by examiner

SEQUENCE LISTING

```
<160> NUMBER OF SEQ ID NOS: 45

<210> SEQ ID NO 1
<211> LENGTH: 34
<212> TYPE: DNA
<213> ORGANISM: Artificial Sequence
<220> FEATURE:
<223> OTHER INFORMATION: probe sequence for let-7a
<220> FEATURE:
<221> NAME/KEY: misc_feature
<222> LOCATION: (1)..(1)
<223> OTHER INFORMATION: 5' acrydite
<220> FEATURE:
<221> NAME/KEY: misc_feature
<222> LOCATION: (34)..(34)
<223> OTHER INFORMATION: 3' inverted dT

<400> SEQUENCE: 1
gatatatttt aaactataca acctactacc tcat                              34

<210> SEQ ID NO 2
<211> LENGTH: 34
<212> TYPE: DNA
<213> ORGANISM: Artificial Sequence
<220> FEATURE:
<223> OTHER INFORMATION: probe sequence for miR-21
<220> FEATURE:
```

```
<221> NAME/KEY: misc_feature
<222> LOCATION: (1)..(1)
<223> OTHER INFORMATION: 5' acrydite
<220> FEATURE:
<221> NAME/KEY: misc_feature
<222> LOCATION: (34)..(34)
<223> OTHER INFORMATION: 3' inverted dT

<400> SEQUENCE: 2
gatatatttt atcaacatca gtctgataag ctat                              34

<210> SEQ ID NO 3
<211> LENGTH: 35
<212> TYPE: DNA
<213> ORGANISM: Artificial Sequence
<220> FEATURE:
<223> OTHER INFORMATION: probe sequence fof miR-29b-2
<220> FEATURE:
<221> NAME/KEY: misc_feature
<222> LOCATION: (1)..(1)
<223> OTHER INFORMATION: 5' acrydite
<220> FEATURE:
<221> NAME/KEY: misc_feature
<222> LOCATION: (35)..(35)
<223> OTHER INFORMATION: 3' inverted dT

<400> SEQUENCE: 3
gatatatttt aaacactgat ttcaaatggt gctat                             35

<210> SEQ ID NO 4
<211> LENGTH: 35
<212> TYPE: DNA
<213> ORGANISM: Artificial Sequence
<220> FEATURE:
<223> OTHER INFORMATION: probe sequence for miR-18ab-1
<220> FEATURE:
<221> NAME/KEY: misc_feature
<222> LOCATION: (1)..(1)
<223> OTHER INFORMATION: 5' acrydite
<220> FEATURE:
<221> NAME/KEY: misc_feature
<222> LOCATION: (35)..(35)
<223> OTHER INFORMATION: 3' inverted dT

<400> SEQUENCE: 4
gatatatttt aacccaccga cagcaatgaa tgttt                             35

<210> SEQ ID NO 5
<211> LENGTH: 33
<212> TYPE: DNA
<213> ORGANISM: Artificial Sequence
<220> FEATURE:
<223> OTHER INFORMATION: probe sequence for miR-143
<220> FEATURE:
<221> NAME/KEY: misc_feature
<222> LOCATION: (1)..(1)
<223> OTHER INFORMATION: 5' acrydite
<220> FEATURE:
<221> NAME/KEY: misc_feature
<222> LOCATION: (33)..(33)
<223> OTHER INFORMATION: 3' inverted dT

<400> SEQUENCE: 5
gatatatttt agagctacag tgcttcatct cat                               33

<210> SEQ ID NO 6
<211> LENGTH: 35
<212> TYPE: DNA
<213> ORGANISM: Artificial Sequence
<220> FEATURE:
<223> OTHER INFORMATION: probe sequence for miR-145
<220> FEATURE:
```

```
<221> NAME/KEY: misc_feature
<222> LOCATION: (1)..(1)
<223> OTHER INFORMATION: 5' acrydite
<220> FEATURE:
<221> NAME/KEY: misc_feature
<222> LOCATION: (35)..(35)
<223> OTHER INFORMATION: 3' inverted dT

<400> SEQUENCE: 6
gatatatttt aagggattcc tgggaaaact ggact                              35

<210> SEQ ID NO 7
<211> LENGTH: 34
<212> TYPE: DNA
<213> ORGANISM: Artificial Sequence
<220> FEATURE:
<223> OTHER INFORMATION: probe sequence for miR-146a
<220> FEATURE:
<221> NAME/KEY: misc_feature
<222> LOCATION: (1)..(1)
<223> OTHER INFORMATION: 5' acrydite
<220> FEATURE:
<221> NAME/KEY: misc_feature
<222> LOCATION: (34)..(34)
<223> OTHER INFORMATION: 3' inverted dT

<400> SEQUENCE: 7
gatatatttt aaacccatgg aattcagttc tcat                               34

<210> SEQ ID NO 8
<211> LENGTH: 34
<212> TYPE: DNA
<213> ORGANISM: Artificial Sequence
<220> FEATURE:
<223> OTHER INFORMATION: probe sequence for miR-210
<220> FEATURE:
<221> NAME/KEY: misc_feature
<222> LOCATION: (1)..(1)
<223> OTHER INFORMATION: 5' acrydite
<220> FEATURE:
<221> NAME/KEY: misc_feature
<222> LOCATION: (34)..(34)
<223> OTHER INFORMATION: 3' inverted dT

<400> SEQUENCE: 8
gatatatttt atcagccgct gtcacacgca cagt                               34

<210> SEQ ID NO 9
<211> LENGTH: 35
<212> TYPE: DNA
<213> ORGANISM: Artificial Sequence
<220> FEATURE:
<223> OTHER INFORMATION: probe sequence for miR-221
<220> FEATURE:
<221> NAME/KEY: misc_feature
<222> LOCATION: (1)..(1)
<223> OTHER INFORMATION: 5' acrydite
<220> FEATURE:
<221> NAME/KEY: misc_feature
<222> LOCATION: (35)..(35)
<223> OTHER INFORMATION: 3' inverted dT

<400> SEQUENCE: 9
gatatatttt agaaacccag cagacaatgt agctt                              35

<210> SEQ ID NO 10
<211> LENGTH: 33
<212> TYPE: DNA
<213> ORGANISM: Artificial Sequence
<220> FEATURE:
<223> OTHER INFORMATION: probe sequence for miR-222
<220> FEATURE:
```

```
<221> NAME/KEY: misc_feature
<222> LOCATION: (1)..(1)
<223> OTHER INFORMATION: 5' acrydite
<220> FEATURE:
<221> NAME/KEY: misc_feature
<222> LOCATION: (33)..(33)
<223> OTHER INFORMATION: 3' inverted dT

<400> SEQUENCE: 10
gatatatttt aacccagtag ccagatgtag ctt                              33

<210> SEQ ID NO 11
<211> LENGTH: 33
<212> TYPE: DNA
<213> ORGANISM: Artificial Sequence
<220> FEATURE:
<223> OTHER INFORMATION: probe sequence for miSpike
<220> FEATURE:
<221> NAME/KEY: misc_feature
<222> LOCATION: (1)..(1)
<223> OTHER INFORMATION: 5' acrydite
<220> FEATURE:
<221> NAME/KEY: misc_feature
<222> LOCATION: (33)..(33)
<223> OTHER INFORMATION: 3' inverted dT

<400> SEQUENCE: 11
gatatatttt aagaccgctc cgccatcctg agt                              33

<210> SEQ ID NO 12
<211> LENGTH: 54
<212> TYPE: DNA
<213> ORGANISM: Artificial Sequence
<220> FEATURE:
<223> OTHER INFORMATION: probe sequence for RNU6B
<220> FEATURE:
<221> NAME/KEY: misc_feature
<222> LOCATION: (1)..(1)
<223> OTHER INFORMATION: 5' acrydite
<220> FEATURE:
<221> NAME/KEY: misc_feature
<222> LOCATION: (54)..(54)
<223> OTHER INFORMATION: 3' inverted dT

<400> SEQUENCE: 12
gatatatttt aaaaaatatg gaacgcttca cgaatttgcg tgtcatcctt gcgt        54

<210> SEQ ID NO 13
<211> LENGTH: 34
<212> TYPE: DNA
<213> ORGANISM: Artificial Sequence
<220> FEATURE:
<223> OTHER INFORMATION: let-7a probe
<220> FEATURE:
<221> NAME/KEY: misc_feature
<222> LOCATION: (1)..(1)
<223> OTHER INFORMATION: 5' acrydite
<220> FEATURE:
<221> NAME/KEY: misc_feature
<222> LOCATION: (34)..(34)
<223> OTHER INFORMATION: 3' inverted dT

<400> SEQUENCE: 13
gatatatttt aaactataca acctactacc tcat                             34

<210> SEQ ID NO 14
<211> LENGTH: 22
<212> TYPE: RNA
<213> ORGANISM: Artificial Sequence
<220> FEATURE:
<223> OTHER INFORMATION: let-7a target
```

```
-continued

<400> SEQUENCE: 14
ugagguagua gguuguauag uu                                              22

<210> SEQ ID NO 15
<211> LENGTH: 10
<212> TYPE: DNA
<213> ORGANISM: Artificial Sequence
<220> FEATURE:
<223> OTHER INFORMATION: UA10-Cy3
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (10)..(10)
<223> OTHER INFORMATION: 3' Cy3

<400> SEQUENCE: 15
taaaatatat                                                            10

<210> SEQ ID NO 16
<211> LENGTH: 10
<212> TYPE: DNA
<213> ORGANISM: Artificial Sequence
<220> FEATURE:
<223> OTHER INFORMATION: UA10-bio
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (10)..(10)
<223> OTHER INFORMATION: 3' biotin

<400> SEQUENCE: 16
taaaatatat                                                            10

<210> SEQ ID NO 17
<211> LENGTH: 13
<212> TYPE: DNA
<213> ORGANISM: Artificial Sequence
<220> FEATURE:
<223> OTHER INFORMATION: UA10-bio
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (13)..(13)
<223> OTHER INFORMATION: 3' biotin

<400> SEQUENCE: 17
taaaatatat aaa                                                        13

<210> SEQ ID NO 18
<211> LENGTH: 16
<212> TYPE: DNA
<213> ORGANISM: Artificial Sequence
<220> FEATURE:
<223> OTHER INFORMATION: UA10-bio
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (16)..(16)
<223> OTHER INFORMATION: 3' biotin
```

```
<400> SEQUENCE: 18
taaaatatat aaaaaa                                                16

<210> SEQ ID NO 19
<211> LENGTH: 22
<212> TYPE: DNA
<213> ORGANISM: Artificial Sequence
<220> FEATURE:
<223> OTHER INFORMATION: UA10-bio
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (22)..(22)
<223> OTHER INFORMATION: 3' biotin

<400> SEQUENCE: 19
taaaatatat aaaaaaaaaa aa                                         22

<210> SEQ ID NO 20
<211> LENGTH: 21
<212> TYPE: RNA
<213> ORGANISM: Artificial Sequence
<220> FEATURE:
<223> OTHER INFORMATION: Sequences for mature miR-143

<400> SEQUENCE: 20
ugagaugaag cacuguagcu c                                          21

<210> SEQ ID NO 21
<211> LENGTH: 55
<212> TYPE: RNA
<213> ORGANISM: Artificial Sequence
<220> FEATURE:
<223> OTHER INFORMATION: Sequences for precursor miR-143

<400> SEQUENCE: 21
ggugcagugc ugcaucucug gucaguuggg agucugagau gaagcacugu agcuc      55

<210> SEQ ID NO 22
<211> LENGTH: 32
<212> TYPE: DNA
<213> ORGANISM: Artificial Sequence
<220> FEATURE:
<223> OTHER INFORMATION: probe for labeling the 3' end of mature miR-143
<220> FEATURE:
<221> NAME/KEY: misc_feature
<222> LOCATION: (1)..(1)
<223> OTHER INFORMATION: 5' acrylate

<400> SEQUENCE: 22
gatatatttt agagctacag tgcttcatct ca                              32

<210> SEQ ID NO 23
<211> LENGTH: 31
<212> TYPE: DNA
<213> ORGANISM: Artificial Sequence
<220> FEATURE:
<223> OTHER INFORMATION: probe for labeling the 5' end of mature miR-143
<220> FEATURE:
<221> NAME/KEY: misc_feature
<222> LOCATION: (1)..(1)
<223> OTHER INFORMATION: 5' acrylate

<400> SEQUENCE: 23
gagctacagt gcttcatctc aatttatatt t                               31
```

```
<210> SEQ ID NO 24
<211> LENGTH: 22
<212> TYPE: DNA
<213> ORGANISM: Artificial Sequence
<220> FEATURE:
<223> OTHER INFORMATION: adapter sequence for 3' labeling
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (22)..(22)
<223> OTHER INFORMATION: 3' biotin

<400> SEQUENCE: 24
taaaatatat aaaaaaaaaa aa                                            22

<210> SEQ ID NO 25
<211> LENGTH: 15
<212> TYPE: RNA
<213> ORGANISM: Artificial Sequence
<220> FEATURE:
<223> OTHER INFORMATION: adapter sequence for 5' labeling
<220> FEATURE:
<221> NAME/KEY: misc_feature
<222> LOCATION: (1)..(1)
<223> OTHER INFORMATION: 5' biotin

<400> SEQUENCE: 25
aaaaaaaaau auaau                                                    15

<210> SEQ ID NO 26
<211> LENGTH: 20
<212> TYPE: DNA
<213> ORGANISM: Artificial Sequence
<220> FEATURE:
<223> OTHER INFORMATION: stem-loop encoding probe
<220> FEATURE:
<221> NAME/KEY: misc_feature
<222> LOCATION: (1)..(1)
<223> OTHER INFORMATION: 5' acrydite

<400> SEQUENCE: 26
aataaacacg ggaataaccc                                               20

<210> SEQ ID NO 27
<211> LENGTH: 10
<212> TYPE: DNA
<213> ORGANISM: Artificial Sequence
<220> FEATURE:
<223> OTHER INFORMATION: probe anchor
<220> FEATURE:
<221> NAME/KEY: misc_feature
<222> LOCATION: (1)..(1)
<223> OTHER INFORMATION: 5' acrydite

<400> SEQUENCE: 27
gatatatttt                                                          10

<210> SEQ ID NO 28
<211> LENGTH: 10
<212> TYPE: DNA
<213> ORGANISM: Artificial Sequence
<220> FEATURE:
<223> OTHER INFORMATION: fluorescently-labeled encoding adapter
<220> FEATURE:
<221> NAME/KEY: misc_feature
<222> LOCATION: (1)..(1)
<223> OTHER INFORMATION: 5' phosphate
<220> FEATURE:
```

```
<221> NAME/KEY: misc_feature
<222> LOCATION: (10)..(10)
<223> OTHER INFORMATION: Cy3

<400> SEQUENCE: 28
gtgtttataa                                                              10

<210> SEQ ID NO 29
<211> LENGTH: 11
<212> TYPE: DNA
<213> ORGANISM: Artificial Sequence
<220> FEATURE:
<223> OTHER INFORMATION: unlabeled adapter
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (11)..(11)
<223> OTHER INFORMATION: inverted dT

<400> SEQUENCE: 29
gtgtttataa t                                                            11

<210> SEQ ID NO 30
<211> LENGTH: 20
<212> TYPE: DNA
<213> ORGANISM: Artificial Sequence
<220> FEATURE:
<223> OTHER INFORMATION: UCode1 probe
<220> FEATURE:
<221> NAME/KEY: misc_feature
<222> LOCATION: (1)..(1)
<223> OTHER INFORMATION: 5' acrydite

<400> SEQUENCE: 30
aataaacacg ggaataaccc                                                   20

<210> SEQ ID NO 31
<211> LENGTH: 20
<212> TYPE: DNA
<213> ORGANISM: Artificial Sequence
<220> FEATURE:
<223> OTHER INFORMATION: UCode2 probe
<220> FEATURE:
<221> NAME/KEY: misc_feature
<222> LOCATION: (1)..(1)
<223> OTHER INFORMATION: 5' acrydite

<400> SEQUENCE: 31
aataatgtgc ccaataaggg                                                   20

<210> SEQ ID NO 32
<211> LENGTH: 10
<212> TYPE: DNA
<213> ORGANISM: Artificial Sequence
<220> FEATURE:
<223> OTHER INFORMATION: UCode 1 adapter Cy3
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (9)..(9)
<223> OTHER INFORMATION: 3' Cy3Sp

<400> SEQUENCE: 32
gtgtttatta                                                              10
```

```
<210> SEQ ID NO 33
<211> LENGTH: 11
<212> TYPE: DNA
<213> ORGANISM: Artificial Sequence
<220> FEATURE:
<223> OTHER INFORMATION: UCode 1 adapter invdT
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (11)..(11)
<223> OTHER INFORMATION: 3' inverted dT

<400> SEQUENCE: 33
gtgtttatta t                                                          11

<210> SEQ ID NO 34
<211> LENGTH: 10
<212> TYPE: DNA
<213> ORGANISM: Artificial Sequence
<220> FEATURE:
<223> OTHER INFORMATION: UCode 2 adapter Cy3
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (10)..(10)
<223> OTHER INFORMATION: 3' Cy3Sp

<400> SEQUENCE: 34
cacattatta                                                            10

<210> SEQ ID NO 35
<211> LENGTH: 11
<212> TYPE: DNA
<213> ORGANISM: Artificial Sequence
<220> FEATURE:
<223> OTHER INFORMATION: UCode 2 adapter invdT
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (11)..(11)
<223> OTHER INFORMATION: 3' inverted dT

<400> SEQUENCE: 35
cacattatta t                                                          11

<210> SEQ ID NO 36
<211> LENGTH: 20
<212> TYPE: DNA
<213> ORGANISM: Artificial Sequence
<220> FEATURE:
<223> OTHER INFORMATION: UC1
<220> FEATURE:
<221> NAME/KEY: misc_feature
<222> LOCATION: (1)..(1)
<223> OTHER INFORMATION: 5' acrylate

<400> SEQUENCE: 36
aataaacacg ggaataaccc                                                 20

<210> SEQ ID NO 37
<211> LENGTH: 20
<212> TYPE: DNA
```

```
<213> ORGANISM: Artificial Sequence
<220> FEATURE:
<223> OTHER INFORMATION: US2
<220> FEATURE:
<221> NAME/KEY: misc_feature
<222> LOCATION: (1)..(1)
<223> OTHER INFORMATION: 5' acrylate

<400> SEQUENCE: 37
aataatgtgc ccaataaggg                                              20

<210> SEQ ID NO 38
<211> LENGTH: 20
<212> TYPE: DNA
<213> ORGANISM: Artificial Sequence
<220> FEATURE:
<223> OTHER INFORMATION: UC3
<220> FEATURE:
<221> NAME/KEY: misc_feature
<222> LOCATION: (1)..(1)
<223> OTHER INFORMATION: 5' acrylate

<400> SEQUENCE: 38
aataactctg ggaataaccc                                              20

<210> SEQ ID NO 39
<211> LENGTH: 10
<212> TYPE: DNA
<213> ORGANISM: Artificial Sequence
<220> FEATURE:
<223> OTHER INFORMATION: UC1-A-Cy3
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (10)..(10)
<223> OTHER INFORMATION: 3' Cy3

<400> SEQUENCE: 39
gtgtttatta                                                         10

<210> SEQ ID NO 40
<211> LENGTH: 10
<212> TYPE: DNA
<213> ORGANISM: Artificial Sequence
<220> FEATURE:
<223> OTHER INFORMATION: UC1-A-NF
<220> FEATURE:
<221> NAME/KEY: misc_feature
<222> LOCATION: (1)..(1)
<223> OTHER INFORMATION: 5' phosphate

<400> SEQUENCE: 40
gtgtttatta                                                         10

<210> SEQ ID NO 41
<211> LENGTH: 10
<212> TYPE: DNA
<213> ORGANISM: Artificial Sequence
<220> FEATURE:
<223> OTHER INFORMATION: UC1-A-FAM6
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (10)..(10)
<223> OTHER INFORMATION: 3' FAM6
```

```
<400> SEQUENCE: 41
gtgtttatta                                                          10

<210> SEQ ID NO 42
<211> LENGTH: 10
<212> TYPE: DNA
<213> ORGANISM: Artificial Sequence
<220> FEATURE:
<223> OTHER INFORMATION: UC2-Cy5
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (10)..(10)
<223> OTHER INFORMATION: 3' Cy5

<400> SEQUENCE: 42
cacattatta                                                          10

<210> SEQ ID NO 43
<211> LENGTH: 10
<212> TYPE: DNA
<213> ORGANISM: Artificial Sequence
<220> FEATURE:
<223> OTHER INFORMATION: UC3-A-Cy3
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (10)..(10)
<223> OTHER INFORMATION: 3' Cy3

<400> SEQUENCE: 43
agagttatta                                                          10

<210> SEQ ID NO 44
<211> LENGTH: 10
<212> TYPE: DNA
<213> ORGANISM: Artificial Sequence
<220> FEATURE:
<223> OTHER INFORMATION: UC3-A-NF
<220> FEATURE:
<221> NAME/KEY: misc_feature
<222> LOCATION: (1)..(1)
<223> OTHER INFORMATION: 5' phosphate

<400> SEQUENCE: 44
agagttatta                                                          10

<210> SEQ ID NO 45
<211> LENGTH: 10
<212> TYPE: DNA
<213> ORGANISM: Artificial Sequence
<220> FEATURE:
<223> OTHER INFORMATION: UC3-A-FAM6
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (10)..(10)
<223> OTHER INFORMATION: 3' FAM6

<400> SEQUENCE: 45
agagttatta                                                          10
```

NUCLEIC ACID DETECTION AND QUANTIFICATION BY POST-HYBRIDIZATION LABELING AND UNIVERSAL ENCODING

RELATED REFERENCES

This application is a continuation of International Application No. PCT/US11/39531, filed Jun. 7, 2011 which claims priority to U.S. provisional patent applications Ser. No. 61/352,018, filed Jun. 7, 2010, Ser. No. 61/365,738, filed Jul. 19, 2010, and Ser. No. 61/387,958, filed Sep. 29, 2010, the entire contents of which are herein incorporated by reference.

SEQUENCE LISTING

In accordance with 37 CFR 1.52(e)(5), a Sequence Listing in the form of a text file (entitled "Sequence Listing.txt," created on Aug. 6, 2012, and 14 kilobytes in size) is incorporated herein by reference in its entirety.

BACKGROUND

The multiplexed detection of biomolecules plays an important role in clinical diagnostics, discovery, and basic science. This requires the ability to both encode substrates associated with specific biomolecule targets, and also to associate a detectable signal to the biomolecule target being quantified. For multiplexed assays, it is common to use functionalized substrates, planar or particle-based, to capture and quantify targets. In the case of particle-based multiplexed assays, each particle is functionalized with a probe that captures a specific target, and encoded for identification during analysis. In order to quantify the amount of target captured on a particle, a suitable labeling scheme is typically used to provide a measurable signal associated with the target. One class of molecules that is particularly challenging to quantify due to limitations with existing approaches to labeling is microRNA (miRNA).

miRNAs are short non-coding RNAs that mediate protein translation and are known to be dysregulated in diseases including diabetes, Alzheimer's, and cancer. With greater stability and predictive value than mRNA, this relatively small class of biomolecules has become increasingly important in disease diagnosis and prognosis. However, the sequence homology, wide range of abundance, and common secondary structures of miRNAs have complicated efforts to develop accurate, unbiased quantification techniques. Applications in the discovery and clinical fields require high-throughput processing, large coding libraries for multiplexed analysis, and the flexibility to develop custom assays. Microarray approaches provide high sensitivity and multiplexing capacity, but their low-throughput, complexity, and fixed design make them less than ideal for use in a clinical setting. PCR-based strategies suffer from similar throughput issues, require lengthy optimization for multiplexing, and are only semi-quantitative. Existing bead-based systems provide a high sample throughput (>100 samples per day), but with reduced sensitivity, dynamic range, and multiplexing capacities. Therefore, there is a need for improved methods for detecting and quantifying nucleic acids, such as, miRNA.

The multiplexed detection of miRNAs, or any other biomolecules requires the ability to encode a substrate associated with each. There are two broad classes of technologies used for multiplexing—planar arrays and suspension (particle-based) arrays, both of which have application-specific advantages. While planar arrays rely strictly on positional encoding, suspension arrays have utilized a great number of encoding schemes that can be classified as spectrometric, graphical, electronic, or physical.

Spectrometric encoding encompasses any scheme that relies on the use of specific wavelengths of light or radiation (including fluorophores, chromophores, photonic structures, or Raman tags) to identify a species. Fluorescence-encoded microbeads can be rapidly processed using conventional flow-cytometry (or on fiber-optic arrays), making them a popular platform for multiplexing. Most spectrometric encoding methods rely on the encapsulation of detectable entities for encoding, which can be very challenging depending on the substrate used. A more robust and generally-applicable encoding method is needed to enable rapid, universal encoding of substrates for multiplexed detection.

SUMMARY

The present invention provides improved methods and compositions for highly efficient, multiplexing, robust and reproducible nucleic acid detection and quantification. The present invention is, in part, based on the discovery that a post-hybridization labeling technique can be used with a suitable flow-through scanning or static imaging system for rapid, high-performance nucleic acid detection and/or quantification. Surprisingly, this post-hybridization labeling approach, when used with a versatile particle encoding method, provides scalable multiplexing and attomole sensitivity with a simple workflow. As described in detail below, using this robust platform, miRNA expression profiling can be accurately analyzed for various cancer types within three hours using low-input total RNA. Although miRNA was used as an example, inventive methods and compositions according to the invention may be used to detect any nucleic acids (e.g., DNA, RNA) or other types of analytes. Thus, the present invention represent a significant advance in the field of multiplexed biomolecule detection and quantification.

In one aspect, the disclosure in the present application provides a substrate comprising at least one region bearing one or more nucleic acid probes, each nucleic acid probe comprising a capturing sequence for capturing sequence for binding a target nucleic acid and an adjacent adapter sequence for binding a universal adapter such that binding of both the target nucleic acid and the universal adapter to a same nucleic acid probe is detectable via post-hybridization labeling.

In one aspect, the disclosure in the present application provides a nucleic acid probe comprising a capturing sequence for binding a target nucleic acid and an adjacent adapter sequence for binding a universal adapter such that binding of both the target nucleic acid and the universal adapter to the nucleic acid probe is detectable via post-hybridization labeling.

In one aspect, the disclosure in the present application provides a substrate comprising one or more universal encoding regions, each universal encoding region bearing one or more single-stranded polynucleotide templates, wherein each template comprises a stem-loop structure and a predetermined nucleotide sequence adjacent to the stem-loop structure.

Among other things, the present invention provides a method for detecting the presence and/or abundance of target nucleic acids in a sample. In some embodiments, such a method includes steps of: contacting a plurality of nucleic acid probes with a sample, each nucleic acid probe comprising a capturing sequence for binding a target nucleic acid and an adjacent adapter sequence for binding a universal adapter; incubating the plurality of probes and the sample, in the presence of one or more universal adapters, under conditions that permit binding of both an individual target nucleic acid and an individual universal adapter to a same individual nucleic acid probe; carrying out a reaction that allows coupling of the individual universal adapter to the individual target nucleic acid when hybridized to the same individual nucleic acid probe; and detecting the presence of the one or more universal adapters associated with the plurality of nucleic acid probes, thereby detecting the presence of the target nucleic acids in the sample.

Among other things, the present invention provides a method of encoding a substrate. In some embodiments, such a method includes steps of: providing a substrate comprising one or more encoding regions, each encoding region bearing one or more single-stranded polynucleotide templates; providing a plurality of labeled and unlabeled single-stranded encoding adapters, wherein each individual single-stranded encoding adapter comprises a sequence designed to specifically bind an individual polynucleotide template and wherein a labeled single-stranded encoding adapter comprises a detectable moiety; incubating the substrate with the plurality of labeled and unlabeled single-stranded encoding adapters under conditions that allow an individual encoding adapter to bind its corresponding single-stranded polynucleotide template; and coupling the individual encoding adapter to its corresponding polynucleotide template, thereby encoding the substrate.

Also provided is a kit for detecting target nucleic acids. In some embodiments, such a kit includes: a plurality of nucleic acid probes, wherein each individual nucleic acid probe comprises a capturing sequence for binding a target nucleic acid of interest and an adjacent adapter sequence for binding a universal adapter; and one or more universal adapters.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/ approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE FIGURES

The drawings are for illustration purposes only, not for limitation.

DEFINITIONS

Figure 1A:
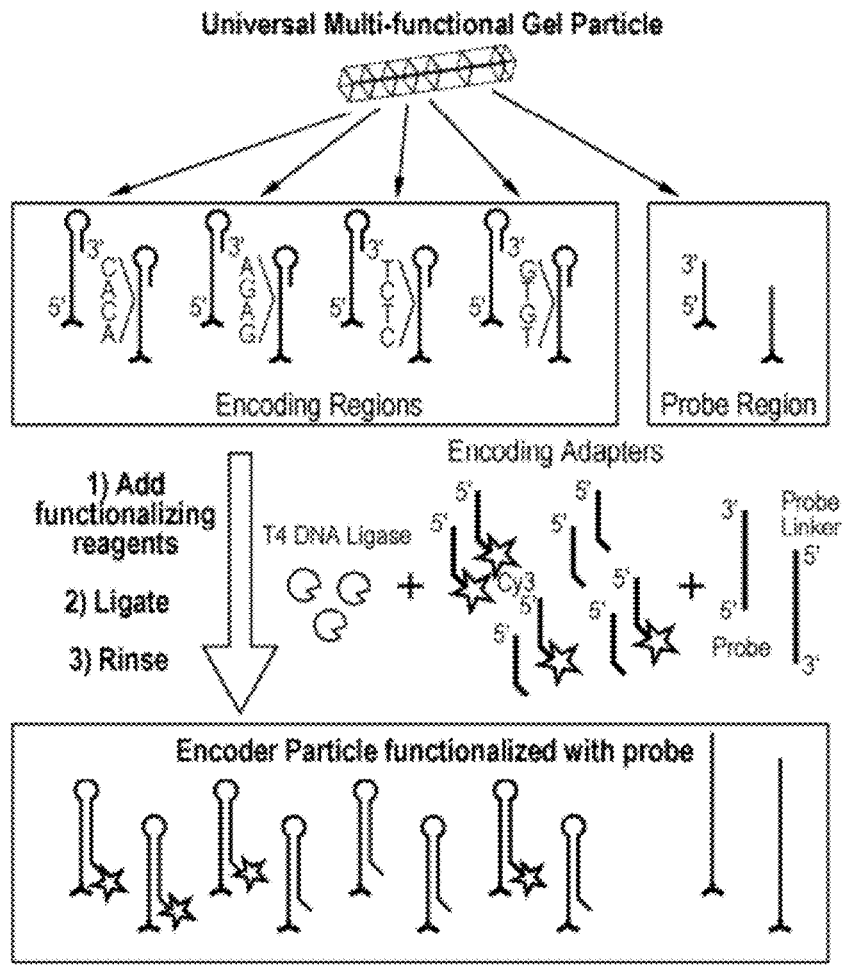
FIG. 1 illustrates an exemplary schematic for universal encoding and functionalization. (a) Hydrogel particles are made to have several universal encoding regions, each with a stem-loop structure and unique 4 bp sequence adjacent to the stem-loop, and a universal anchor in the probe region. In a ligation reaction, encoding adapters are added at varying ratios of fluorescently-modified to unmodified in order to achieve a desired fluorescence level in each region while probes are added with linker sequence to add functionality to the particle probe region. (b) An example of two batches of particles with unique code and probes generated using a universal particle set with varying ligation adapters.

In order for the present invention to be more readily understood, certain terms are first defined below. Additional definitions for the following terms and other terms are set forth throughout the specification.

In order for the present invention to be more readily understood, certain terms are first defined below. Additional definitions for the following terms and other terms are set forth throughout the specification.

"Adjacent": As used herein, the term "adjacent" means "next to," "contiguous," "adjoining," "abutting" or having a common boundary.

"Analyte": As used herein, the term "analyte" broadly refers to any substance to be analyzed, detected, measured, or quantified. Examples of analytes include, but are not limited to, proteins, peptides, hormones, haptens, antigens, antibodies, receptors, enzymes, nucleic acids, polysaccharides, chemicals, polymers, pathogens, toxins, organic drugs, inorganic drugs, cells, tissues, microorganisms, viruses, bacteria, fungi, algae, parasites, allergens, pollutants, and combinations thereof.

"Associated": As used herein, the terms "associated", "conjugated", "linked", "attached", "complexed", and "tethered," and grammatical equivalents, typically refer to two or more moieties connected with one another, either directly or indirectly (e.g., via one or more additional moieties that serve as a linking agent), to form a structure that is sufficiently stable so that the moieties remain connected under the conditions in which the structure is used, e.g., physiological conditions. In some embodiments, the moieties are attached to one another by one or more covalent bonds. In some embodiments, the moieties are attached to one another by a mechanism that involves specific (but non-covalent) binding (e.g. streptavidin/avidin interactions, antibody/antigen interactions, etc.). Alternatively or additionally, a sufficient number of weaker interactions (non-covalent) can provide sufficient stability for moieties to remain connected. Exemplary non-covalent interactions include, but are not limited to, affinity interactions, metal coordination, physical adsorption, host-guest interactions, hydrophobic interactions, pi stacking interactions, hydrogen bonding interactions, van der Waals interactions, magnetic interactions, electrostatic interactions, dipole-dipole interactions, etc.

"Biomolecules": The term "biomolecules", as used herein, refers to molecules (e.g., proteins, amino acids, peptides, polynucleotides, nucleotides, carbohydrates, sugars, lipids, nucleoproteins, glycoproteins, lipoproteins, steroids, etc.) whether naturally-occurring or artificially created (e.g., by synthetic or recombinant methods) that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

"Biocompatible": The term "biocompatible", as used herein is intended to describe materials that do not elicit a substantial detrimental response in vivo. In some embodiments, a substance is considered to be "biocompatible" if its addition to cells in vitro or in vivo results in less than or equal to about 50%, about 45%, about 40%, about 35%, about 30%, about 25%, about 20%, about 15%, about 10%, about 5%, or less than about 5% cell death.

"Biodegradable": As used herein, the term "biodegradable" refers to substances that are degraded under physiological conditions. In some embodiments, a biodegradable substance is a substance that is broken down by cellular machinery. In some embodiments, a biodegradable substance is a substance that is broken down by chemical processes.

"Complement": As used herein, the terms "complement," "complementary" and "complementarity," refer to the pairing of nucleotide sequences according to Watson/Crick pairing rules. For example, a sequence 5'-GCGGTCCCA-3' has the complementary sequence of 5'-TGGGACCGC-3'. A complement sequence can also be a sequence of RNA complementary to the DNA sequence. Certain bases not commonly found in natural nucleic acids may be included in the complementary nucleic acids including, but not limited to, inosine, 7-deazaguanine, Locked Nucleic Acids (LNA), and Peptide Nucleic Acids (PNA). Complementary need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

"Contemporaneous" and "non-contemporaneous": As used herein, the terms "contemporaneous," "contemporaneously," or grammatical equivalents, mean that multiple events occur or happen at the same time without a detectable or identifiable sequential order. As used herein, the terms "non-contemporaneous," "non-contemporaneously," or grammatical equivalents, mean that multiple events occur or happen in a detectable or identifiable sequential order.

"Crude": As used herein, the term "crude," when used in connection with a biological sample, refers to a sample which is in a substantially unrefined state. For example, a crude sample can be cell lysates or biopsy tissue sample. A crude sample may exist in solution or as a dry preparation.

"Encoding region," "coding region," or "barcoded region": As used herein, the terms "encoding region," "coding region," "barcoded region", or grammatical equivalents, refer to a region on an object or substrate (e.g., particle) that can be used to identify the object or substrate (e.g., particle). These terms may be used inter-changeably. Typically, an encoding region of an object bears graphical and/or optical features associated with the identity of the object. Such graphical and/or optical features are also referred to as signature features of the object. In some embodiments, an encoding region of an object bears spatially patterned features (e.g., stripes with various shapes and/or dimensions, or a series of holes with various sizes) that give rise to variable fluorescent intensities (of one or multiple wavelengths). In some embodiments, an encoding region of an object bears various type and/or amount of fluorophores or other detectable moieties, in various spatial patterns, that give rise to variable fluorescent signals (e.g., different colors and/or intensities) in various patterns.

"Functionalization: As used herein, the term "functionalization" refers to any process of modifying a material by bringing physical, chemical or biological characteristics different from the ones originally found on the material. Typically, functionalization involves introducing functional groups to the material. As used herein, functional groups are specific groups of atoms within molecules that are responsible for the characteristic chemical reactions of those molecules. As used herein, functional groups include both chemical (e.g., ester, carboxylate, alkyl) and biological groups (e.g., adapter, or linker sequences).

"Hybridize": As used herein, the term "hybridize" or "hybridization" refers to a process where two complementary nucleic acid strands anneal to each other under appropriately stringent conditions. Oligonucleotides or probes suitable for hybridizations typically contain 10-100 nucleotides in length (e.g., 18-50, 12-70, 10-30, 10-24, 18-36 nucleotides in length). Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to estimate and adjust the stringency of hybridization conditions such that sequences having at least a desired level of complementary will stably hybridize, while those having lower complementary will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

"Hydrodynamic diameter": The term "hydrodynamic diameter", as used herein, generally refers to the effective diameter of a hydrated molecule (e.g., macromolecules, colloids, or particles) in solution, corresponding to the diameter of a sphere with equal mobility in solution. In some embodiments, a hydrodynamic diameter is used to describe the measured size of particles in solution. In certain embodiments, hydrodynamic diameter may be determined by dynamic light scattering size measurement. For example, Zetasizer Nano ZS instrument (Malvern) can be used to measure the hydrodynamic diameter of particles as demonstrated in the Example Section below.

"Inert region": As used herein, the terms "inert region," "inert spacer" or grammatical equivalents, when used in connection with a region on an object (e.g., particle), refer to a region that is not detectable above a pre-determined triggering threshold by a flow-through scanning device such as a flow cytometer. Typically, an inert region or spacer is a non-functionalized region. For example, an inert region is a region not loaded with probes or other detectable moieties.

"Interrogate": As used herein, the terms "interrogate," "interrogating," "interrogation" or grammatical equivalents, refer to a process of characterizing or examining to obtain data.

"Labeled": The terms "labeled" and "labeled with a detectable agent or moiety" are used herein interchangeably to specify that an entity (e.g., a nucleic acid probe, antibody, etc.) can be visualized, for example following binding to another entity (e.g., a nucleic acid, polypeptide, etc.). The detectable agent or moiety may be selected such that it generates a signal which can be measured and whose intensity is related to (e.g., proportional to) the amount of bound entity. A wide variety of systems for labeling and/or detecting proteins and peptides are known in the art. Labeled proteins and peptides can be prepared by incorporation of, or conjugation to, a label that is detectable by spectroscopic, photochemical, biochemical, immunochemical, electrical, optical, chemical or other means. A label or labeling moiety may be directly detectable (i.e., it does not require any further reaction or manipulation to be detectable, e.g., a fluorophore is directly detectable) or it may be indirectly detectable (i.e., it is made detectable through reaction or binding with another entity that is detectable, e.g., a hapten is detectable by immunostaining after reaction with an appropriate antibody comprising a reporter such as a fluorophore). Suitable detectable agents include, but are not limited to, radionucleotides, fluorophores, chemiluminescent agents, microparticles, enzymes, colorimetric labels, magnetic labels, haptens, molecular beacons, aptamer beacons, and the like.

"Monodisperse": As used herein, the terms "monodisperse" or "monosized" refer to a collection of objects that have substantially the same size and shape when in the context of particles, and substantially the same mass in the context of polymers. Conversely, a collection of objects that have an inconsistent size, shape and mass distribution are called polydisperse. Monodisperse particles are typically synthesized through the use of template-based synthesis.

"Object" or "substrate": As used herein, the terms "object" and "substrate" are used interchangeably and refer to any discrete mass. An object or substrate can be a particle, bead, planar surface, phage, macromolecules, cell, micro-organism, and the like.

"Particle": The term "particle," as used herein, refers to a discrete object. Such object can be of any shape or size. Composition of particles may vary, depending on applications and methods of synthesis. Suitable materials include, but are not limited to, plastics, ceramics, glass, polystyrene, methylstyrene, acrylic polymers, metal, paramagnetic materials, thoria sol, carbon graphited, titanium dioxide, latex or cross-linked dextrans such as Sepharose, cellulose, nylon, cross-linked micelles and teflon. In some embodiments, particles can be optically or magnetically detectable. In some embodiments, particles contain fluorescent or luminescent moieties, or other detectable moieties. In some embodiments, particles having a diameter of less than 1000 nanometers (nm) are also referred to as nanoparticles.

"Polynucleotide", "nucleic acid", or "oligonucleotide": The terms "polynucleotide", "nucleic acid", or "oligonucleotide" refer to a polymer of nucleotides. The terms "polynucleotide", "nucleic acid", and "oligonucleotide", may be used interchangeably. Typically, a polynucleotide comprises at least three nucleotides. DNAs and RNAs are polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5"-N-phosphoramidite linkages).

"Probe": As used herein, the term "probe" refers to a fragment of DNA or RNA of variable length (e.g., 3-1000 bases long), which is used to detect the presence of target nucleotide sequences that are complementary to the sequence in the probe. Typically, the probe hybridizes to single-stranded nucleic acid (DNA or RNA) whose base sequence allows probe-target base pairing due to complementarity between the probe and target.

"Secondary Structure": As used herein, the term "secondary structure", when used in connection with a nucleic acid structure, refers to any structure formed by basepairing interactions within a single molecule or set of interacting molecules. Exemplary secondary structures include stem-loop or double helix.

"Signal": As used herein, the term "signal" refers to a detectable and/or measurable entity. In certain embodiments, the signal is detectable by the human eye, e.g., visible. For example, the signal could be or could relate to intensity and/or wavelength of color in the visible spectrum. Non-limiting examples of such signals include colored precipitates and colored soluble products resulting from a chemical reaction such as an enzymatic reaction. In certain embodiments, the signal is detectable using an apparatus. In some embodiments, the signal is generated from a fluorophore that emits fluorescent light when excited, where the light is detectable with a fluorescence detector. In some embodiments, the signal is or relates to light (e.g., visible light and/or ultraviolet light) that is detectable by a spectrophotometer. For example, light generated by a chemiluminescent reaction could be used as a signal. In some embodiments, the signal is or relates to radiation, e.g., radiation emitted by radioisotopes, infrared radiation, etc. In certain embodiments, the signal is a direct or indirect indicator of a property of a physical entity. For example, a signal could be used as an indicator of amount and/or concentration of a nucleic acid in a biological sample and/or in a reaction vessel.

"Specific": As used herein, the term "specific," when used in connection with an oligonucleotide primer, refers to an oligonucleotide or primer, under appropriate hybridization or washing conditions, is capable of hybridizing to the target of interest and not substantially hybridizing to nucleic acids which are not of interest. Higher levels of sequence identity are preferred and include at least 60%, 65%, 70%, 75%, 80%, 85%, 90%, 95%, 98%, 99%, or 100% sequence identity. In some embodiments, a specific oligonucleotide or primer contains at least 4, 6, 8, 10, 12, 14, 16, 18, 20, 22, 24, 26, 28, 30, 35, 40, 45, 50, 55, 60, 65, 70, or more bases of sequence identity with a portion of the nucleic acid to be hybridized or amplified when the oligonucleotide and the nucleic acid are aligned.

"Stem-loop": As used herein, the term "stem-loop", when used in connection with a nucleic acid structure, refers to a structure caused by an intramolecular base pairing typically occurring in single-stranded DNA or in RNA. The structure is also known as a hairpin or hairpin loop. Typically, it occurs when two regions of the same strand, usually complementary in nucleotide sequence when read in opposite directions, base-pair to form a double helix that ends in an unpaired loop, resulting in lollipop-shaped structure.

"Substantially": As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

"Substantially complementary": As used herein, the term "substantially complementary" refers to two sequences that can hybridize under stringent hybridization conditions. The skilled artisan will understand that substantially complementary sequences need not hybridize along their entire length. In some embodiments, "stringent hybridization conditions" refer to hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5×Denhart's solution at 42° C. overnight; washing with 2×SSC, 0.1% SDS at 45° C.; and washing with 0.2×SSC, 0.1% SDS at 45° C. In some embodiments, stringent hybridization conditions should not allow for hybridization of two nucleic acids which differ over a stretch of 20 contiguous nucleotides by more than two bases.

DETAILED DESCRIPTION OF CERTAIN EMBODIMENTS

The present invention provides, among other things, methods and compositions for detecting and quantifying target nucleic acids via post-hybridization labeling. In some embodiments, the present invention provides a method for detecting the presence and/or abundance of target nucleic acids in a sample by (a) contacting a plurality of nucleic acid probes with a sample, each nucleic acid probe comprising a capturing sequence for binding a target nucleic acid and an adjacent adapter sequence for binding a universal adapter; (b) incubating the plurality of probes and the sample, in the presence of one or more universal adapters, under conditions that permit binding of both an individual target nucleic acid and an individual universal adapter to a same individual nucleic acid probe; (c) carrying out a reaction that allows coupling of the individual universal adapter to the individual target nucleic acid when hybridized to the same individual nucleic acid probe; (d) detecting the presence of the one or more universal adapters associated with the plurality of nucleic acid probes, thereby detecting the presence of the target nucleic acids in the sample. Typically, universal adapters are labeled with detectable moieties or other labeling groups to facilitate detection. In some embodiments, the plurality of nucleic acid probes suitable for the invention are attached to a substrate or object (e.g., microarray, or particle).

In addition, it is contemplated that such ligation-based approach (or other coupling approach) may be used to encode or otherwise functionalize various objects or substrates (e.g., particles). Thus, in some embodiments, the present invention provides methods and compositions for universal encoding. In particular embodiments, the present invention provides a method of encoding an object (e.g., particle) by (a) providing an object or a substrate (e.g., particle) containing one or more encoding regions with each encoding region bearing one or more single-stranded polynucleotide templates; (b) providing a blend of detectably labeled (e.g., labeled with fluorophores or other detectable moieties) and unlabeled single-stranded encoding adapters, wherein each individual encoding adapter contains a sequence designed to specifically bind a polynucleotide template; (c) incubating the object with the encoding adapters under conditions that allow individual encoding adapters to bind their corresponding polynucleotide templates; and (d) coupling the encoding adapters to their corresponding polynucleotide templates, thereby encoding the object or substrate. In some embodiments, by varying the amount of labeled adapter versus unlabeled adapter (with the same or similar sequence), it is possible to control the amount of signal generated (e.g., fluorescence) in each encoding region. Alternatively or additionally, objects or substrates (e.g., particles) embedded with nucleic acid anchors in a probe region can be used to attach desired probes to functionalize the probe region of objects or substrates (e.g., particles). In this manner, encoding and probe functionalization can be achieved in a single reaction.

Thus, inventive methods according to the present invention enable the production of several batches of objects (e.g., particles) with unique codes and probes from a single batch of objects (e.g., particles) with a universal architecture. For highly multiplexed assays, this greatly reduces production time and cost compared to independent synthesis particle batches for each target. Importantly, particles generated using this method can also be used with post-hybridization labeling approach for highly effective nucleic acid (e.g., microRNA) detection and quantification described herein.

Various aspects of the invention are described in further detail in the following subsections. The use of subsections is not meant to limit the invention. Each subsection may apply to any aspect of the invention. In this application, the use of "or" means "and/or" unless stated otherwise.

Nucleic Acid Probes for Post-Hybridization Labeling

Nucleic acid probes suitable for the present invention are designed to generate a detectable signal indicating the presence and capture of nucleic acid targets, e.g., miRNA targets. Thus, in some embodiments, a nucleic acid probe suitable for the present invention includes a capturing sequence for binding a target nucleic acid of interest and an adjacent adapter sequence for binding a universal adapter. According to the invention, the capturing sequence and the adapter sequence are configured such that binding of both the target nucleic acid and the universal adapter to the nucleic acid probe permits joining of the universal adapter to the target nucleic acid. In some embodiments, once both the target nucleic acid and the universal adapter bound to the nucleic acid probe, the 3' end of the target would abut the 5' end of the universal adapter. In some embodiments, once both the target nucleic acid and the universal adapter bound to the nucleic acid probe, the 5' end of the target would abut the 3' end of the universal adapter. In some embodiments, the universal adapter may be joined, linked, attached or coupled to the targeted nucleic acid by enzymatic or chemical coupling. In some embodiments, a DNA or RNA ligase is used to link the universal adapter to the target nucleic acid. In some embodiments, a T4 DNA ligase is used to link the universal adapter to the target nucleic acid. In some embodiments, a common, detectable universal adapter can be used to label multiple targets in a single reaction.

Capturing Sequence

In some embodiments, a suitable capturing sequence is specific to a target nucleic acid (e.g., DNA, mRNA, or microRNA). The term "specific" when used in connection with a hybridization probe refers to a sequence that can bind to its target under stringent conditions but not to other regions.

For example, a suitable capturing sequence may contain a sequence substantially complementary to a target sequence on a target nucleic acid, such as a microRNA. Typically, a capturing sequence is based on a target-specific nucleotide sequence. In some embodiments, a capturing sequence may contain a sequence substantially complementary to a sequence specific to an microRNA of interest, e.g., microRNAs indicative of certain cancer, diabetes, Alzheimer's or other diseases including but not limited to, let-7a, miR-21, miR-29b-2, miR-181b-1, miR-143, miR-145, miR-146a, miR-210, miR-221, miR-222, miR-10b, miR-15a, miR-16, miR-17, miR-18a, miR-19a, miR20a, miR-1, miR-29, miR-181, miR372, miR-373, miR-155, miR-101, miR-195, miR-29, miR-17-3p, miR-92a, miR-25, miR-223, miR-486, miR-223, miR-375, miR-99b, miR-127, miR-126, miR-184.

In some embodiments, a suitable capturing sequence may be designed to distinguish different variable species of target nucleic acids. The present invention is particularly useful to distinguish among multiple species of target nucleic acids with identical sequences at one end and variable sequences at the other end. Thus, in some embodiments, a capturing sequence can be designed to be complementary to a desired variable end nucleotide sequence. Only the binding of a desired target species will have a perfectly matching 3' end that abut the 5'end of the adapter sequence thereby permitting ligation of the adapter to the target. Therefore, the detection of the universal adapter associated with the probe indicates the presence of the target nucleic acid with the desired end variability in the sample. In particular embodiments, the present invention is used to distinguish a precursor-microRNA from a mature microRNA. Typically, a precursor-microRNA and mature microRNA have identical 5' region but distinct 3' region due to the cleavage of the 3' arm from the precursor form during the maturation process. In order to specifically detect a mature microRNA, a capturing sequence may be designed to be substantially complementary to the sequence at the 3' end of the mature microRNA. Therefore, only the binding of a correct mature microRNA to the capturing sequence would result in the perfectly matching 3' end of the microRNA abutting the 5' end of the adapter sequence permitting ligation of the adapter sequence to the target sequence.

In some embodiments, a capturing sequence for nucleic acid targets contains up to 50 nucleotides (e.g., up to 25, 20, 18, 16, 15, 14, 13, 12, 11, 10, 9, 8, 7, 6, 5, 4, 3, 2, or 1 nucleotides). In some embodiments, a capturing sequence is also chosen to ensure that the melting temperature Tm is between 20-50 C in ligation buffer.

Adapter Sequence

Generally, an adapter sequence can be any sequence and length. Typically, an adapter sequence and length are designed to such that (1) the melting temperature is between about 10-20 C in ligation buffer, (2) the sequence is not significantly self-complementary in order to avoid formation of hairpin, other secondary structure or homodimer, and/or (3) complete DNA probes (with adapter and miRNA sequence) does not form appreciable hairpins or other secondary structures. In some embodiments, a suitable adapter sequence contains up to 20 nucleotides (e.g., up to 19, 18, 17, 16, 15, 14, 13, 12, 11, 10, 9, 8, 7, 6, 5, 4, 3, 2, or 1 nucleotides).

In some embodiments, a suitable nucleic acid probe contains a 3' cap to prevent or mitigate incidental ligation. Exemplary suitable 3' caps include, but are not limited to, inverted dT, or 3' phosphates. In some embodiments, a suitable nucleic acid probe contains a chemical anchor at the 5' or 3' end such that the probe can be attached to a substrate. Suitable exemplary chemical anchor groups include, but are not limited to, carboxy groups, amine groups, thiol groups, biotin, and/or azide groups. In some embodiments, a suitable probe may contain a particular nucleic acid sequence for association of the probe with a particular substrate or a specific location of on a substrate. Typically, such particular nucleic acid sequence is predetermined to be complementary to a capturing sequence embedded on a desired location of a substrate. In some embodiments, the capture of the nucleic acid probe at a desired location is associated with the identity of the probe. Therefore, such particular nucleic acid sequences are also referred to as nucleic acid barcode.

Suitable probes typically are of a length that is large enough to hybridize specifically with its target but not so large as to impede the hybridization process. The size may be dependent on the desired melting temperature of the target-probe complex or required specificity of target discrimination. In some embodiments, suitable probes contains about 10-70 nucleotides (e.g., 10-60, 10-50, 10-40, 10-30, 10-25, 10-20, 15-70, 15-60, 15-50, 15-40, 15-30, 15-25, 20-70, 20-60, 20-50, 20-40, 20-30 nucleotides). Various methods and softwares available in the art can be used to design specific probes.

Nucleic acid probes according to the invention may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

Universal Adapter

According to the invention, a suitable universal adapter contains a sequence complementary to the adapter sequence of a corresponding nucleic acid probe such that, once the universal adapter bound to the nucleic acid probe, the 5' or 3' end of the adapter abuts the 3' or 5' end of a target nucleic acid, respectively. Suitable lengths and sequences of a universal adaptor can be selected using methods well known and documented in the art. For example a suitable adapter may contain between 1 and 25 nucleotides in length (e.g., 1-20, 1-18, 1-16, 1-14, 1-12, 1-10, 5-20, 5-15, or 5-10 nucleotides).

Adapters may be DNA, RNA, or any type of nucleic acid analog. The nucleotides in adapters may be natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2"-fluororibose, ribose, 2'-deoxyribose, arabinose, and hexose), or modified phosphate groups (e.g., phosphorothioates and 5"-N-phosphoramidite linkages).

In some embodiments, a universal adapter is biotinylated. In some embodiments, a biotinylated universal adapter may be detected by a streptavidin reporter conjugated to a detectable moiety including, but not limited to, phycoerythrin, PE-Cy5, PE-Cy5.5, PE-Cy7, APC, PerCP, quantum dots, fluorophores or other detectable entities as described herein (see the "Detectable entities" section below). In some embodiments, a biotinylated universal adapter may be detected by a streptavidin reporter conjugated to enzyme for enzymatic signal generation. In some embodiments, a suitable streptavidin reporter is conjugated to Alkaline Phosphatase, beta-Galactosidase, horse radish peroxidase, or other enzyme capable of turning over detectable products. In some embodiments, enzymatic signal generation permits chemiluminescence, fluorescence, or chromogenic detection (see the Detectable entities section). In some embodiments, a universal adapter contains a nucleotide tail (also referred to as spacer or linker) to extend the biotin or enzyme group away from the polymer backbone of the gel matrix to avoid possible steric hindrance. A suitable nucleotide tail (spacer or linker) may contain various sequences. In some embodiments, a poly(A) or poly(T) tail is used. In some embodiments, a suitable nucleotide (such as a poly(A)) tail contains up to 12, 11, 10, 9, 8, 7, 6, 5, 4, 3, 2, or 1 bases.

In some embodiments, a universal adapter is directly labeled with fluorophores or other detectable entities (see the "Detectable moieties" section).

In some embodiments, multiple universal adapters may be used to label multiple distinct target nucleic acids in one reaction. Typically, in such cases, each individual universal adapter is labeled with distinctively detectable moieties or is detected by distinct biotin-streptavidin reporter system.

Exemplary detectable entities suitable for the present invention are described below.

Detectable Entities

Any of a wide variety of detectable agents can be used in the practice of the present invention. Suitable detectable agents include, but are not limited to: various ligands, radionuclides; fluorescent dyes; chemiluminescent agents (such as, for example, acridinum esters, stabilized dioxetanes, and the like); bioluminescent agents; spectrally resolvable inorganic fluorescent semiconductors nanocrystals (i.e., quantum dots); microparticles; metal nanoparticles (e.g., gold, silver, copper, platinum, etc.); nanoclusters; paramagnetic metal ions; enzymes; colorimetric labels (such as, for example, dyes, colloidal gold, and the like); biotin; dioxigenin; haptens; and proteins for which antisera or monoclonal antibodies are available.

In some embodiments, the detectable moiety is biotin. Biotin can be bound to avidins (such as streptavidin), which are typically conjugated (directly or indirectly) to other moieties (e.g., fluorescent moieties) that are detectable themselves.

Below are described some non-limiting examples of other detectable moieties.

Fluorescent Dyes

In certain embodiments, a detectable moiety is a fluorescent dye. Numerous known fluorescent dyes of a wide variety of chemical structures and physical characteristics are suitable for use in the practice of the present invention. A fluorescent detectable moiety can be stimulated by a laser with the emitted light captured by a detector. The detector can be a charge-coupled device (CCD) or a confocal microscope, which records its intensity.

Suitable fluorescent dyes include, but are not limited to, fluorescein and fluorescein dyes (e.g., fluorescein isothiocyanine or FITC, naphthofluorescein, 4',5'-dichloro-2',7'-dimethoxyfluorescein, 6-carboxyfluorescein or FAM, etc.), carbocyanine, merocyanine, styryl dyes, oxonol dyes, phycoerythrin, erythrosin, eosin, rhodamine dyes (e.g., carboxytetramethyl-rhodamine or TAMRA, carboxyrhodamine 6G, carboxy-X-rhodamine (ROX), lissamine rhodamine B, rhodamine 6G, rhodamine Green, rhodamine Red, tetramethylrhodamine (TMR), etc.), coumarin and coumarin dyes (e.g., methoxycoumarin, dialkylaminocoumarin, hydroxycoumarin, aminomethylcoumarin (AMCA), etc.), Oregon Green Dyes (e.g., Oregon Green 488, Oregon Green 500, Oregon Green 514, etc.), Texas Red, Texas Red-X, SPECTRUM RED™, SPECTRUM GREEN™, cyanine dyes (e.g., CY-3™, CY-5™, CY-3.5™, CY-5.5™, etc.), ALEXA FLUOR™ dyes (e.g., ALEXA FLUOR™ 350, ALEXA FLUOR™ 488, ALEXA FLUOR™ 532, ALEXA FLUOR™ 546, ALEXA FLUOR™ 568, ALEXA FLUOR™ 594, ALEXA FLUOR™ 633, ALEXA FLUOR™ 660, ALEXA FLUOR™ 680, etc.), BODIPY™ dyes (e.g., BODIPY™ FL, BODIPY™ R6G, BODIPY™ TMR, BODIPY™ TR, BODIPY™ 530/550, BODIPY™ 558/568, BODIPY™ 564/570, BODIPY™ 576/589, BODIPY™ 581/591, BODIPY™ 630/650, BODIPY™ 650/665, etc.), IRDyes (e.g., IRD40, IRD 700, IRD 800, etc.), and the like. For more examples of suitable fluorescent dyes and methods for coupling fluorescent dyes to other chemical entities such as proteins and peptides, see, for example, "The Handbook of Fluorescent Probes and Research Products", 9th Ed., Molecular Probes, Inc., Eugene, Oreg. Favorable properties of fluorescent labeling agents include high molar absorption coefficient, high fluorescence quantum yield, and photostability. In some embodiments, labeling fluorophores exhibit absorption and emission wavelengths in the visible (i.e., between 400 and 750 nm) rather than in the ultraviolet range of the spectrum (i.e., lower than 400 nm).

A detectable moiety may include more than one chemical entity such as in fluorescent resonance energy transfer (FRET). Resonance transfer results an overall enhancement of the emission intensity. For instance, see Ju et. al. (1995) Proc. Nat'l Acad. Sci. (USA) 92: 4347, the entire contents of which are herein incorporated by reference. To achieve resonance energy transfer, the first fluorescent molecule (the "donor" fluor) absorbs light and transfers it through the resonance of excited electrons to the second fluorescent molecule (the "acceptor" fluor). In one approach, both the donor and acceptor dyes can be linked together and attached to the oligo primer. Methods to link donor and acceptor dyes to a nucleic acid have been described previously, for example, in U.S. Pat. No. 5,945,526 to Lee et al., the entire contents of which are herein incorporated by reference. Donor/acceptor pairs of dyes that can be used include, for example, fluorescein/tetramethylrhodamine, IAEDANS/fluorescein, EDANS/DABCYL, fluorescein/fluorescein, BODIPY FL/BODIPY FL, and Fluorescein/QSY 7 dye. See, e.g., U.S. Pat. No. 5,945,526 to Lee et al. Many of these dyes also are commercially available, for instance, from Molecular Probes Inc. (Eugene, Oreg.). Suitable donor fluorophores include 6-carboxyfluorescein (FAM), tetrachloro-6-carboxyfluorescein (TET), 2'-chloro-7'-phenyl-1,4-dichloro-6-carboxyfluorescein (VIC), and the like.

A suitable detectable moiety can be an intercalating DNA/RNA dye that have dramatic fluorescent enhancement upon binding to double-stranded DNA/RNA. Examples of suitable dyes include, but are not limited to, SYBR™ and Pico Green (from Molecular Probes, Inc. of Eugene, Oreg.), ethidium bromide, propidium iodide, chromomycin, acridine orange, Hoechst 33258, Toto-1, Yoyo-1, and DAPI (4',6-diamidino-2-phenylindole hydrochloride). Additional discussion regarding the use of intercalation dyes is provided by Zhu et al., Anal. Chem. 66:1941-1948 (1994), which is incorporated by reference in its entirety.

Enzymes

In certain embodiments, a detectable moiety is an enzyme. Examples of suitable enzymes include, but are not limited to, those used in an ELISA, e.g., horseradish peroxidase, beta-galactosidase, luciferase, alkaline phosphatase, etc. Other examples include beta-glucuronidase, beta-D-glucosidase, urease, glucose oxidase, etc. An enzyme may be conjugated to a molecule using a linker group such as a carbodiimide, a diisocyanate, a glutaraldehyde, and the like.

Radioactive Isotopes

In certain embodiments, a detectable moiety is a radioactive isotope. For example, a molecule may be isotopically-labeled (i.e., may contain one or more atoms that have been replaced by an atom having an atomic mass or mass number different from the atomic mass or mass number usually found in nature) or an isotope may be attached to the molecule. Non-limiting examples of isotopes that can be incorporated into molecules include isotopes of hydrogen, carbon, fluorine, phosphorous, copper, gallium, yttrium, technetium, indium, iodine, rhenium, thallium, bismuth, astatine, samarium, and lutetium (i.e., 3H, 13C, 14C, 18F, 19F, 32P, 35S, 64Cu, 67Cu, 67Ga, 90Y, 99 mTc, 111In, 125I, 123I, 129I, 131I, 135I, 186Re, 187Re, 201Tl, 212Bi, 213Bi, 211At, 153Sm, 177Lu).

In some embodiments, signal amplification is achieved using labeled dendrimers as the detectable moiety (see, e.g., Physiol Genomics 3:93-99, 2000), the entire contents of which are herein incorporated by reference in their entirety. Fluorescently labeled dendrimers are available from Genisphere (Montvale, N.J.). These may be chemically conjugated to the oligonucleotide primers by methods known in the art.

Substrates

In some embodiments, a nucleic acid probe suitable for post-hybridization labeling is attached to a substrate or object. Suitable substrates or objects may have a planer, spherical or non-spherical morphologies. Suitable substrates or objects may be solid, semi-solid, polymer, emulsion, or the like. Suitable substrates or objects include, but are not limited to, microarrays, glasses, slides, particles, beads, films, membranes, microspheres (e.g., glass, polymer, etc.) with exterior or interior surface, cells including any genetically engineered cells, micro-organisms (e.g., C. elegans (e.g., engineered nematodes for drug testing), bacteria, yeast, and/or fungi) including any genetically engineered micro-organisms.

For illustration purposes, particles are used in various embodiments below.

Particles

Particles suitable for use in accordance with the present invention can be made of any materials. Suitable particles can be biocompatible, non-biocompatible. Suitable particles can also be biodegradable or non-biodegradable.

Materials

In some embodiments, particles are made of polymers. Exemplary polymers include, but are not limited to, poly(arylates), poly(anhydrides), poly(hydroxy acids), polyesters, poly(ortho esters), poly(alkylene oxides), polycarbonates, polypropylene fumerates), poly(caprolactones), polyamides, polyamino acids, polyacetals, polylactides, polyglycolides, poly(dioxanones), polyhydroxybutyrate, polyhydroxyvalyrate, poly(vinyl pyrrolidone), polycyanoacrylates, polyurethanes and polysaccharides. In some embodiments, polymers of particles include polyethylene glycol (PEG). In some embodiments, polymers of particles may be formed by step or chain polymerization. The amount and kind of radical initiator, e.g., photo-active initiator (e.g., UV or infrared), thermally-active initiator, or chemical initiator, or the amount of heat or light employed, may be used to control the rate of reaction or modify the molecular weight. Where desired, a catalyst may be used to increase the rate of reaction or modify the molecular weight. For example, a strong acid may be used as a catalyst for step polymerization. Trifunctional and other multifunctional monomers or cross-linking agents may also be used to increase the cross-link density. For chain polymerizations, the concentration of a chemical initiator in a mixture of one or more monomers may be adjusted to manipulate final molecular weight.

Exemplary methods for making particles are described in U.S. Pat. No. 7,709,544 and US Application Publication No.: 20080176216, the entire contents of which are incorporated herein by reference. For example, processes as discussed can be conducted with any polymerizable liquid-phase monomer in which shapes of particles suitable for use in the present invention, can be defined and polymerized in a single lithography-polymerization step. Exemplary monomers include Allyl Methacrylate, Benzyl Methylacrylate, 1,3-Butanediol Dimethacrylate, 1,4-Butanediol Dimethacrylate, Butyl Acrylate, n-Butyl Methacrylate, Diethyleneglycol Diacrylate, Diethyleneglycol Dimethacrylate, Ethyl Acrylate, Ethyleneglycol Dimethacrylate, Ethyl Methacrylate, 2-Ethyl Hexyl Acrylate, 1,6-Hexanediol Dimethacrylate, 4-Hydroxybutyl Acrylate, Hydroxyethyl Acrylate, 2-Hydroxyethyl Methacrylate, 2-Hydroxypropyl Acrylate, Isobutyl Methacrylate, Lauryl Methacrylate, Methacrylic Acid, Methyl Acrylate, Methyl Methacrylate, Monoethylene Glycol, 2,2,3,3,4,4,5,5-Octafluoropentyl Acrylate, Pentaerythritol Triacrylate, Polyethylene Glycol (200) Diacrylate, Polyethylene Glycol (400) Diacrylate, Polyethylene Glycol (600) Diacrylate, Polyethylene Glycol (200) Dimethacrylate, Polyethylene Glycol (400) Dimethacrylate, Polyethylene Glycol (600) Dimethacrylate, Stearyl Methacrylate, Triethylene Glycol, Triethylene Glycol Dimethacrylate, 2,2,2-Trifluoroethyl 2-methylacrylate, Trimethylolpropane Triacrylate, Acrylamide, N,N,-methylene-bisacryl-amide, Phenyl acrylate, Divinyl benzene, etc. In certain embodiments, a monomer is characterized by a polymerization reaction that can be terminated with a termination species. The terminating species, lithographic illumination, and monomer constituents are therefore selected in cooperation to enable making particles suitable for use in the present invention.

In some embodiments, particles are hydrogels. In general, hydrogels comprise a substantially dilute crosslinked network. Water or other fluids can penetrate in the network forming such a hydrogel. In some embodiments, hydrogels suitable for use in the present invention are made of or comprise a hydrophilic polymer. For example, hydrophilic polymers may comprise anionic groups (e.g. phosphate group, sulphate group, carboxylate group); cationic groups (e.g. quaternary amine group); or polar groups (e.g. hydroxyl group, thiol group, amine group). In some embodiments, hydrogels are superabsorbent (e.g. they can contain over 99% water) and possess a degree of flexibility very similar to natural tissue, due to their significant water content. Both of weight and volume, hydrogels are fluid in composition and thus exhibit densities to those of their constituent liquids (e.g., water). The present invention encompasses the recognition that hydrogels are particularly useful in some embodiments of the present invention. Without wishing to be bound to any particular theory, it is contemplated that hydrogels enable 1) ease of implementation with detection instruments, in particular, commercially available instruments without substantial modifications (e.g., flow cytometers), and 2) ease of incorporation of functional moieties (e.g., in a single lithography-polymerization step) without requiring surface functionalization. Due to their bio-friendly nature, hydrogels have been used extensively in the fields of tissue engineering, drug delivery, and biomolecule separation.

Various additional materials and methods can be used to synthesize particles. In some embodiments, particles may be made of or comprise one or more polymers. Polymers used in particles may be natural polymers or unnatural (e.g. synthetic) polymers. In some embodiments, polymers can be linear or branched polymers. In some embodiments, polymers can be dendrimers. Polymers may be homopolymers or copolymers comprising two or more monomers. In terms of sequence, copolymers may be block copolymers, graft copolymers, random copolymers, blends, mixtures, and/or adducts of any of the foregoing and other polymers.

In some embodiments, particles of the present invention may be made of or comprise a natural polymer, such as a carbohydrate, protein, nucleic acid, lipid, etc. In some embodiments, natural polymers may be synthetically manufactured. Many natural polymers, such as collagen, hyaluronic acid (HA), and fibrin, which derived from various components of the mammalian extracellular matrix can be used in particles of the present invention. Collagen is one of the main proteins of the mammalian extracellular matrix, while HA is a polysaccharide that is found in nearly all animal tissues. Alginate and agarose are polysaccharides that are derived from marine algae sources. Some advantages of natural polymers include low toxicity and high biocompatibility.

In some embodiments, a polymer is a carbohydrate. In some embodiments, a carbohydrate may be a monosaccharide (i.e. simple sugar). In some embodiments, a carbohydrate may be a disaccharide, oligosaccharide, and/or polysaccharide comprising monosaccharides and/or their derivatives connected by glycosidic bonds, as known in the art. Although carbohydrates that are of use in the present invention are typically natural carbohydrates, they may be at least partially-synthetic. In some embodiments, a carbohydrate is a derivatized natural carbohydrate.

In certain embodiments, a carbohydrate is or comprises a monosaccharide, including but not limited to glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid. In certain embodiments, a carbohydrate is or comprises a disaccharide, including but not limited to lactose, sucrose, maltose, trehalose, and cellobiose. In certain embodiments, a carbohydrate is or comprises a polysaccharide, including but not limited to hyaluronic acid (HA), alginate, heparin, agarose, chitosan, N,O-carboxylmethylchitosan, chitin, cellulose, microcrystalline cellulose, hydroxypropyl methylcellulose (HPMC), hydroxycellulose (HC), methylcellulose (MC), pullulan, dextran, cyclodextran, glycogen, starch, hydroxyethylstarch, carageenan, glycon, amylose, starch, heparin, konjac, glucommannan, pustulan, curdlan, and xanthan. In certain embodiments, the carbohydrate is a sugar alcohol, including but not limited to mannitol, sorbitol, xylitol, erythritol, maltitol, and lactitol.

In some embodiments, particles of the present invention may be made of or comprise synthetic polymers, including, but not limited to, poly(arylates), poly(anhydrides), poly(hydroxy acids), poly(alkylene oxides), polypropylene fumerates), polymethacrylates polyacetals, polyethylenes, polycarbonates (e.g. poly(1,3-dioxan-2-one)), polyanhydrides (e.g. poly(sebacic anhydride)), polyhydroxyacids (e.g. poly($\beta$-hydroxyalkanoate)), polypropylfumarates, polycaprolactones, polyamides (e.g. polycaprolactam), polyacetals, polyethers, polyesters (e.g. polylactide, polyglycolide, poly(dioxanones), polyhydroxybutyrate,), poly(orthoesters), polycyanoacrylates, polyvinyl alcohols, polyurethanes, polyphosphazenes, polyacrylates, polymethacrylates, polyureas, polyamines and copolymers thereof. Exemplary polymers also include polyvalerolactone, poly(sebacic anhydride), polyethylene glycol, polystyrenes, polyhydroxyvalyrate, poly(vinyl pyrrolidone)poly(hydroxyethyl methacrylate) (PHEMA), poly(vinyl alcohol) (PVA), and derivatives and copolymers thereof.

In some embodiments, polymers of particles may be formed by step or chain polymerization. The amount and kind of radical initiator, e.g., photo-active initiator (e.g., UV or infrared), thermally-active initiator, or chemical initiator, or the amount of heat or light employed, may be used to control polymerization rate or modify molecular weights of resulting polymers. Where desired, a catalyst may be used to increase the rate of reaction or modify the molecular weight. For example, a strong acid may be used as a catalyst for step polymerization. Trifunctional and other multifunctional monomers or cross-linking agents may also be used to increase cross-link density of polymers. For chain polymerizations, the concentration of a chemical initiator in a mixture of one or more monomers may be adjusted to manipulate final molecular weight.

In some embodiments, photocrosslinking methods are utilized to make polymeric particles in accordance with the present invention. Photoinitiators produce reactive free radical species that initiate the crosslinking and/or polymerization of monomers upon exposure to light. Any photoinitiator may be used in the crosslinking and/or polymeriation reaction. Photoinitiated polymerizations and photoinitiators are discussed in detail in Rabek, *Mechanisms of Photophysical Processes and Photochemical Reactions in Polymers*, New York: Wiley & Sons, 1987; Fouassier, *Photoinitiation, Photopolymerization, and Photocuring*, Cincinnati, Ohio: Hanser/Gardner; Fisher et al., 2001, *Annu. Rev. Mater. Res.,* 31:171. A photoinitiator may be designed to produce free radicals at any wavelength of light. In certain embodiments, the photoinitiator is designed to work using UV light (200-500 nm). In certain embodiments, long UV rays are used. In other embodiments, short UV rays are used. In some embodiments, a photoinitiator is designed to work using visible light (400-800 nm). In certain embodiments, a photoinitiator is designed to work using blue light (420-500 nm). In some embodiments, the photoinitiator is designed to work using IR light (800-2500 nm). The output of light can be controlled to provide greater control over the crosslinking and/or polymerization reaction. Control over polymerization in turn results in control over characteristics and/or properties of the resulting hydrogel.

In some embodiments, particle can be or comprises inorganic polymer such as silica ($SiO_2$). In some embodiments, particles according to the invention are silica-based. For example, silicate materials may be useful for the present applications due to their biocompatibility, ease of production and functionalization, and large surface-to-volume ratio. Silica-based particles such as porous silica particles, and any modified or hybrid particles can be of use in accordance with the present invention.

As well known in the art, silica-based particles may be made by a variety of methods. Some methods utilize the Stöber synthesis which involves hydrolysis of tetraethoxyorthosilicate (TEOS) catalyzed by ammonia in water/ethanol mixtures, or variations thereof. In some embodiments, silica-based particles are synthesized using known sol-gel chemistry, e.g., by hydrolysis of a silica precursor or precursors. Silica precursors can be provided as a solution of a silica precursor and/or a silica precursor derivative. Hydrolysis can be carried out under alkaline (basic) or acidic conditions. For example, hydrolysis can be carried out by addition of ammonium hydroxide to a solution comprising one or more silica precursor and/or derivatives. Silica precursors are compounds which under hydrolysis conditions can form silica. Examples of silica precursors include, but are not limited to, organosilanes such as, for example, tetraethoxysilane (TEOS), tetramethoxysilane (TMOS) and the like. In some embodiments, silica precursor has a functional group. Examples of such silica precursors includes, but is not limited to, isocyanatopropyltriethoxysilane (ICPTS), aminopropyltrimethoxysilane (APTS), mercaptopropyltrimethoxysilane (MPTS), and the like. In some embodiments, microemulsion procedures can be used to synthesize particles suitable for use in the present invention. For example, a water-in-oil emulsion in which water droplets are dispersed as nanosized liquid entities in a continuous domain of oil and surfactants and serve as nanoreactors for nanoparticle synthesis offer a convenient approach.

In some embodiments, particles may contain detectable moieties that generate fluorescent, luminescent and/or scatter signal. In certain embodiments, particles contain quantum dots (QDs). QDs are bright, fluorescent nanocrystals with physical dimensions small enough such that the effect of quantum confinement gives rise to unique optical and electronic properties. Semiconductor QDs are often composed of atoms from groups II-VI or III-V in the periodic table, but other compositions are possible. By varying their size and composition, the emission wavelength can be tuned (i.e., adjusted in a predictable and controllable manner) from the blue to the near infrared. QDs generally have a broad absorption spectrum and a narrow emission spectrum. Thus different QDs having distinguishable optical properties (e.g., peak emission wavelength) can be excited using a single source. In general, QDs are brighter and photostable than most conventional fluorescent dyes. QDs and methods for their synthesis are well known in the art (see, e.g., U.S. Pat. Nos. 6,322,901; 6,576,291; and 6,815,064; all of which are incorporated herein by reference). QDs can be rendered water soluble by applying coating layers comprising a variety of different materials (see, e.g. U.S. Pat. Nos. 6,423,551; 6,251,303; 6,319,426; 6,426,513; 6,444,143; and 6,649,138; all of which are incorporated herein by reference). For example, QDs can be solubilized using amphiphilic polymers. Exemplary polymers that have been employed include octylamine-modified low molecular weight polyacrylic acid, polyethylene-glycol (PEG)-derivatized phospholipids, polyanhydrides, block copolymers, etc.

Exemplary QDs suitable for use in accordance with the present invention in some embodiments, includes ones with a wide variety of absorption and emission spectra and they are commercially available, e.g., from Quantum Dot Corp. (Hayward Calif.; now owned by Invitrogen) or from Evident Technologies (Troy, N.Y.). For example, QDs having peak emission wavelengths of approximately 525 nm, approximately 535 nm, approximately 545 nm, approximately 565 nm, approximately 585 nm, approximately 605 nm, approximately 655 nm, approximately 705 nm, and approximately 800 nm are available. Thus QDs can have a range of different colors across the visible portion of the spectrum and in some cases even beyond.

In certain embodiments, optically detectable particles are or comprise metal particles. Metals of use include, but are not limited to, gold, silver, iron, cobalt, zinc, cadmium, nickel, gadolinium, chromium, copper, manganese, palladium, tin, and alloys thereof. Oxides of any of these metals can be used.

Certain metal particles, referred to as plasmon resonant particles, exhibit the well known phenomenon of plasmon resonance. The features of the spectrum of a plasmon resonant particle (e.g., peak wavelength) depend on a number of factors, including the particle's material composition, the shape and size of the particle, the refractive index or dielectric properties of the surrounding medium, and the presence of other particles in the vicinity. Selection of particular particle shapes, sizes, and compositions makes it possible to produce particles with a wide range of distinguishable optically detectable properties thus allowing for concurrent detection of multiple analytes by using particles with different properties such as peak scattering wavelength.

Magnetic properties of particles can be used in accordance with the present invention. Particles in some embodiments are or comprise magnetic particles, that is, magnetically responsive particles that contain one or more metals or oxides or hydroxides thereof. Magnetic particles may comprise one or more ferrimagnetic, ferromagnetic, paramagnetic, and/or superparamagnetic materials. Useful particles may be made entirely or in part of one or more materials selected from the group consisting of: iron, cobalt, nickel, niobium, magnetic iron oxides, hydroxides such as maghemite ($\gamma$-$Fe_2O_3$), magnetite ($Fe_3O_4$), feroxyhyte (FeO(OH)), double oxides or hydroxides of two- or three-valent iron with two- or three-valent other metal ions such as those from the first row of transition metals such as Co(II), Mn(II), Cu(II), Ni(II), Cr(III), Gd(III), Dy(III), Sm(III), mixtures of the afore-mentioned oxides or hydroxides, and mixtures of any of the foregoing. See, e.g., U.S. Pat. No. 5,916,539 (incorporated herein by reference) for suitable synthesis methods for certain of these particles. Additional materials that may be used in magnetic particles include yttrium, europium, and vanadium.

Size and Shape

In general, particles suitable for the present invention can be of any size. In some embodiments, suitable particles have a greatest dimension (e.g. diameter) of less than 1000 micrometers (µm). In some embodiments, suitable particles have a greatest dimension of less than 500 µm. In some embodiments, suitable particles have a greatest dimension of less than about 250 µm. In some embodiments, suitable particles have a greatest dimension (e.g. diameter) of less than about 200 µm, about 150 µm, about 100 µm, about 90 µm, about 80 µm, about 70 µm, about 60 µm, about 50 µm, about 40 µm, about 30 µm, about 20 µm, or about 10 µm. In some embodiments, suitable particles have a greatest dimension of less than 1000 nm. In some embodiments, suitable particles have a greatest dimension of less than 500 nm. In some embodiments, suitable particles have a greatest dimension of less than about 250 nm. In some embodiments, a greatest dimension is a hydrodynamic diameter.

Suitable particles can have a variety of different shapes including, but not limited to, spheres, oblate spheroids, cylinders, ovals, ellipses, shells, cubes, cuboids, cones, pyramids, rods (e.g., cylinders or elongated structures having a square or rectangular cross-section), tetrapods (particles having four leg-like appendages), triangles, prisms, etc. In some embodiments, particles are rod-shaped. In some embodiments, particles are bar-shaped. In some embodiments, particles are bead-shaped. In some embodiments, particles are column-shaped. In some embodiments, particles are ribbon or chain-like. In some embodiments, particles can be of any geometry or symmetry. For example, planar, circular, rounded, tubular, ring-shaped, tetrahedral, hexagonal, octagonal particles, particles of other regular geometries, and/or particles of irregular geometries can also be used in the present invention. Additional suitable particles with various sizes and shapes are disclosed in U.S. Pat. No. 7,709,544 and U.S. Pat. No. 7,947,487 and can be used in the present invention, which are incorporated herein by reference.

Particles may have various aspect ratios of their dimensions, such as length/width, length/thickness, etc. Particles, in some embodiments, can have at least one dimension, such as length, that is longer than another dimension, such as width. According to the present invention, particles having at least one aspect ratio greater than one may be particularly useful in flow-through scanning (e.g., in a flow cytometer) to facilitate their self-alignment. In some embodiments, particles may have at least one aspect ratio of at least 1.5:1, at least 2:1, at least 2.5:1, at least 3:1, at least 5:1, at least 10:1, at least 15:1, or even greater.

It is often desirable to use a population of particles that is relatively uniform in terms of size, shape, and/or composition so that each particle has similar properties. In some embodiments, a population of particles with homogeneity with diameters (e.g., hydrodynamic diameters) are used. As used herein, a population of particles with homogeneity with diameters (e.g., hydrodynamic diameters) refers to a population of particles with at least about 80%, at least about 90%, or at least about 95% of particles with a diameter (e.g., hydrodynamic diameter) that falls within 5%, 10%, or 20% of the average diameter (e.g., hydrodynamic diameter). In some embodiments, the average diameter (e.g., hydrodynamic diameter) of a population of particles with homogeneity with diameters (e.g., hydrodynamic diameters) ranges as discussed above. In some embodiments, a population of particles with homogeneity with diameters (e.g., hydrodynamic diameters) refers to a population of particles that has a polydispersity index less than 0.2, 0.1, 0.05, 0.01, or 0.005. For example, polydispersity index of particles used in accordance with the present invention is in a range of about 0.005 to about 0.1. Without wishing to be bound by any theory, it is contemplated that particles with homogeneity (e.g., with respect to particle size) may have higher repeatability and can produce more accuracy in the present application. In some embodiments, a population of particles may be heterogeneous with respect to size, shape, and/or composition.

Particles can be solid or hollow and can comprise one or more layers (e.g., nanoshells, nanorings, etc.). Particles may have a core/shell structure, wherein the core(s) and shell(s) can be made of different materials. Particles may comprise gradient or homogeneous alloys. Particles may be composite particles made of two or more materials, of which one, more than one, or all of the materials possesses magnetic properties, electrically detectable properties, and/or optically detectable properties.

Particles may have a coating layer. Use of a biocompatible coating layer can be advantageous, e.g., if the particles contain materials that are toxic to cells. Suitable coating materials include, but are not limited to, natural proteins such as bovine serum albumin (BSA), biocompatible hydrophilic polymers such as polyethylene glycol (PEG) or a PEG derivative, phospholipid-(PEG), silica, lipids, polymers, carbohydrates such as dextran, other nanoparticles that can be associated with inventive nanoparticles etc. Coatings may be applied or assembled in a variety of ways such as by dipping, using a layer-by-layer technique, by self-assembly, conjugation, etc. Self-assembly refers to a process of spontaneous assembly of a higher order structure that relies on the natural attraction of the components of the higher order structure (e.g., molecules) for each other. It typically occurs through random movements of the molecules and formation of bonds based on size, shape, composition, or chemical properties. In some embodiments, particles with coating are also referred to as functionalized particles or surface treated particles.

In certain embodiments of the invention, a particle is porous, by which is meant that the particle contains holes or channels, which are typically small compared with the size of a particle. For example a particle may be a porous silica particle, e.g., a porous silica nanoparticle or may have a coating of porous silica. Particles may have pores ranging from about 1 nm to about 200 nm in diameter, e.g., between about 1 nm and 50 nm in diameter. Between about 10% and 95% of the volume of a particle may consist of voids within the pores or channels.

In some embodiments, particles may optionally comprise one or more dispersion media, surfactants, release-retarding ingredients, or other pharmaceutically acceptable excipient. In some embodiments, particles may optionally comprise one or more plasticizers or additives.

In various embodiments, particles described herein may have at least one region bearing one or more probes described herein. In some embodiments, particles may have at least one encoded region. In some embodiments, particles have at least one encoded region and at least one region bearing one or more probes. Such regions can be discrete regions of substrates (objects) including particles used in accordance with the present invention. Each region, in some embodiments, can be optionally functionalized. In various embodiments, particles described herein may bear an indicator for orientation (e.g., indicating coding region first followed by probe region or vice versa).

Functionalization

Various methods known in the art (e.g., as discussed in U.S. Pat. No. 7,709,544 and U.S. Pat. No. 7,947,487) and provided in the present application are useful for functionalization of substrates or objects (e.g., particles) described herein.

Various functional moieties or groups may be introduced to the surface of the substrates that produce selected functionality (e.g., to capture encoding adapters, probes or target nucleic acids). Such functional moieties can be chemically attached to the surface, e.g., by covalent incorporation, or can be physically attached thereto or entrapped therein.

In some embodiments, at least a portion of a substrate is made from a monomer. Such a monomer can be used alone or in combination with copolymerized species to provide a selected functionality in the resulting substrate. For example, a functional moiety can be provided as a monomer or a part of a monomer that are polymerized, for example, by a lithography-polymerization step of particle synthesis (see, U.S. Pat. No. 7,709,544 and U.S. Pat. No. 7,947,487 for details).

It is not intended that the present invention be limited to a particular coding scheme. A signature for encoding can be a visually detectable feature such as, for example, color, apparent size, or visibility (i.e. simply whether or not the particle is visible under particular conditions).

In many embodiments, graphical signatures and/or optically detectable signatures are particularly useful in the present invention. In various embodiments of the present invention, graphically encoding as discussed in U.S. Pat. No. 7,947,487 and encoding (e.g., universal encoding) as disclosed herein are used.

In some embodiments, a graphical signature for encoding is or comprises one or more spatially patterned features. In some embodiments, spatially patterned features include a plurality of open and closed coding elements. Coding elements can be arranged in a two-dimensional grid. Coding elements can also have non-uniform shapes or sizes. In certain embodiments, spatially patterned features further include an orientation indicator.

Additionally or alternatively, an optical signature can be used in accordance with the present invention. In some embodiments, an optical signature for encoding is or comprises a feature of an absorption, emission, reflection, refraction, interference, diffraction, dispersion, scattering, or any combination thereof.

In some embodiments, an optical signature is intrinsic to functionalized substrates in accordance with the present invention. In some embodiments, an optical signature is introduced to functionalized substrates. Such introduction can be done before, with or after contacting with a sample, generating a signal from such contacting, and/or detecting such a signal.

To give but one example, a functionalized substrate may carry a functional moiety that is not itself detectable, but upon further interaction with and/or modification by other moieties can become detectable. In some embodiments, such a functional moiety can be a functional group or moiety to facilitate association between a substrate and other entities.

Thus, additionally or alternatively, substrate surface is functionalized to introduce chemical functional moieties that are designed to facilitate association between a substrate and other entities (e.g., probes, encoding agents, etc.). Suitable functional moieties can be introduced to a surface of substrates by covalent attachment. In some embodiments, coupling agents can be used with various substrates for functionalization. Exemplary coupling agents may include bifunctional, tri-functional, and higher functional coupling agents, which are well known in the art, such as $MeSiCl_3$, dioctylphthalate, polyethylene-glycol (PEG), etc. In some embodiments, substrates are functionalized by covalent attachment of streptavidin onto their surface via a heterobifunctional cross-linker with a polyethylene-glycol (PEG) spacer arm. A variety of functionalization methods are known in the art and can be used to practice the present invention.

In some embodiments, a substrate surface is functionalized by introducing capturing or anchor oligonucleotides to facilitate capturing and immobilization of individual nucleic acid molecules such as single-stranded polynucleotide templates, encoding adapters or probes. In some embodiments, capturing or anchor oligonucleotides can contain sequences complementary to a universal sequence present on nucleic acid template molecules. Exemplary capturing or anchor oligonucleotides can contain various numbers of nucleotides. For example, suitable oligonucleotides may contain 1-50 nucleotides (e.g., 3-40, 3-30, 3-20, 30-15, 3-10, 6-40, 6-30, 6-20, 6-10, 8-30, 8-20, 8-15, 10-30, 10-20, 10-15 nucleotides). In some embodiments, suitable oligonucleotides may contain 1, 2, 3, 6, 8, 10, 12, 14, 16, 18, 20, 25, 30, 35, 40, 45, or 50 nucleotides. Various methods are known in the art for design and synthesize suitable capturing or anchor oligonucleotides and such methods are well within skills of ordinary artisan.

In some embodiments, capturing or anchor oligonucleotides may be separately synthesized and attached to a substrate surface for use, e.g. as disclosed by Lund et al. Nucleic Adds Research, 16: 10861-10880 (1988); Albretsen et al, Anal. Biochem., 189: 40-50 (1990); Wolf et al, Nucleic Acids Research, 15: 2911-2926 (1987); or Ghosh et al, Nucleic Acids Research, 15: 5353-5372 (1987).

In some embodiments, the attachment is covalent in nature. In further embodiments, the covalent binding of the capturing or anchor oligonucleotides and nucleic acid template(s) to the substrate is induced by a crosslinking agent such as for example 1-ethyl-3-(3-dimethylaminopropyl)-carbodiimide hydrochloride (EDC), succinic anhydride, phenyldiisothiocyanate or maleic anhydride, or a hetero-bifunctional crosslinker such as for example m-maleimidobenzoyl-N-hydroxysuccinimide ester (MBS), N-succinimidyl[4-iodoacethyl]aminobenzoate (SIAB), Succinimidyl 4-[N-maleimidomethyl]cyclohexane-1-carboxylate (SMCC), N-y-maleimidobutyryloxy-succinimide ester (GMBS), Succinimidyl-4-[p-maleimidophenyl]butyrate (SMPB) and the sulfo (water-soluble) corresponding compounds.

In some embodiments, functionalized substrates bearing chemical groups or capturing or anchor oligonucleotides are used for universal encoding and/or probe region functionalization.

Universal Encoding

Universal encoding enables the production of functionalized substrates with a universal architecture, which can be further encoded to generate subgroups of substrates with distinct barcode giving rise to distinct identity. For highly multiplexed assays, this greatly reduces production time and cost compared to independent synthesis of subpopulations of substrates for each target.

In some embodiments, a functionalized substrate comprises one or more universal encoding regions. Such encoding regions may be separated by inert or nonfunctionalized regions. Typically, each universal encoding region bearing one or more templates for capturing encoding adapters by covalent link via the functional groups or by hybridization and/or ligation to a capturing or anchor oligonucleotides on the functionalized surface. In some embodiments, a template is or comprises a single-stranded polynucleotide. For example, such a single-stranded polynucleotide can include a predetermined nucleotide sequence that specifically bind a desired encoding adapter. In some embodiments, a template further include a stem-loop structure (i.e., a hairpin structure). Predetermined nucleotide sequences, in certain embodiments, may be adjacent to stem-loop structures to facilitate ligation between the template and the encoding adapter. In such embodiments, an encoding adapter that binds the template typically does not form a secondary structure. In some embodiments, a single stranded template does not forms a hairpin structure, while an encoding adapter does.

In general, a predetermined nucleotide sequence with any base combinations or lengths can be used in accordance with the present invention. In some embodiments, a predetermined nucleotide sequence has a length of 1, 2, 3 bases or more. In some embodiments, a predetermined nucleotide sequence has a length of or more than 4 bases, 5 bases, 6 bases, 7 bases, 8 bases, 9 bases, 10 bases, 11 base, 12 bases, 13 bases, 14 bases, 15 bases, 20 bases, 25 bases or 30 bases. In some embodiments, a predetermined nucleotide sequence has a length in a range of any two values above. The length of predetermined nucleotide sequences can be the same for one substrate or can vary from each other.

In some embodiments, single-stranded polynucleotide templates can be used to capture encoding adapters. Suitable encoding adapters may be DNA, RNA, or any type of nucleic acid analog. In many embodiments, an encoding adapter is or comprises a single-stranded polynucleotide. In some embodiments, an encoding adapter comprises a nucleotide sequence that is complementary to the predetermined sequence of a corresponding template. Typically, an encoding adapter contains up to 30, 25, 20, 18, 16, 15, 14, 13, 12, 11, 10, 9, 8, 7, 6, 5, 4, 3, 2, or 1 nucleotides.

In some embodiments, encoding adapters, once bound to the template, can be joined to the template by T4 DNA ligase or via other enzymatic or chemical coupling.

Encoding adapters can be labeled or unlabeled. In some embodiments, encoding adapters is labeled with a detectable moiety (e.g., an optically detectable moiety). Various detectable moieties may be used including fluorophores, chromophores, radioisotopes, quantum dots, nanoparticles and/or intercalating DNA/RNA dyes. Additional examples of detectable moieties are described in the Detectable Moieties section above.

In various embodiments, encoding adapters used in accordance with the present invention is a blend of labeled and unlabeled encoding adapters. In some embodiments, the labeled and unlabeled encoding adapters have the same or similar sequences and bind the same templates. In some embodiments, by varying the amount of labeled encoding adapters versus unlabeled encoding adapter, it is possible to control the amount of signal generated (e.g. fluorescence) in a region to achieve desired level. In some embodiments, a lock sequence can be used to selectively dictate which adapters will bind and be ligated to each hairpin probe region. In this way, several stripes of independently addressable hairpin probe regions can be used for encoding.

In some embodiments, a signal of at least one labeled encoding adapter is used to determine the orientation of the substrate. In some embodiments, a signal of at least one labeled encoding adapter is used to normalized detectable signals form other labeled encoding adapters.

It is possible to use multiple colors (or emission wavelengths in general) when implementing the universal encoding scheme described herein. This may be accomplished by using blends of universal adapters modified with varying species, such as fluorophores, with unique emission spectra. Depending on the amount of each adapter added to the ligation mix, varying amounts will be ligated to the templates embedded in the particles, allowing levels of multiple "colors" to be adjusted in each encoding region. In one example, two fluorophores can be used to generate two-color codes on particles/substrates as shown below, but more colors can easily be used.

In some embodiments, fluorescence in each coding region can be distinguishable at multiple levels, e.g., up to 10-20 levels (e.g., up to 1, 2, 3, 4, 5, 6, 7, 8, 9, 10, 11, 12, 13, 14, 15, 16, 17, 18, 19, or 20 levels). For example, when three encoding regions are used and 10 levels are distinguishable for each, it would allow up to 1000 (10×10×10) unique codes. Additionally or alternatively, multiple signals (e.g., different fluorescent colors) can be used for encoding. In some embodiments, each encoding region has one signal distinct from each other. In some embodiments, substrates and encoding adapters can be designed such that at least one encoding region of the substrates is attached with one or more kinds of encoding adapters generating multiple signals. In some embodiments, each encoding region has multiple signals and by varying the amount of encoding adapters, a desired signal ratio can be achieved for encoding.

Probe Region Functionalization

Figure 1B:
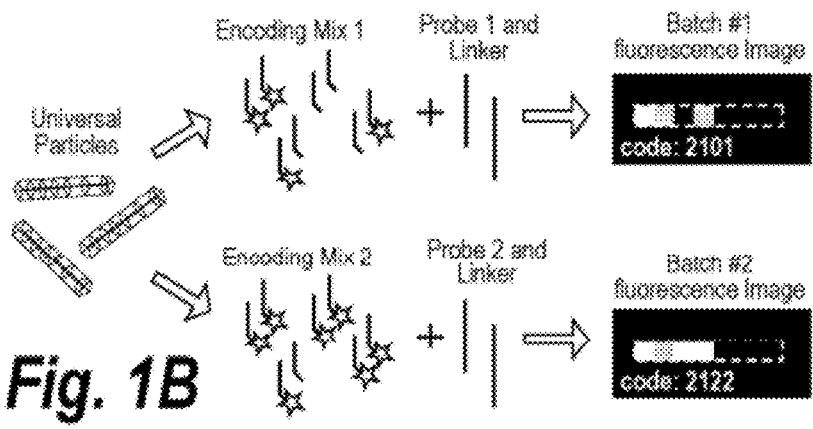
Figure 2:
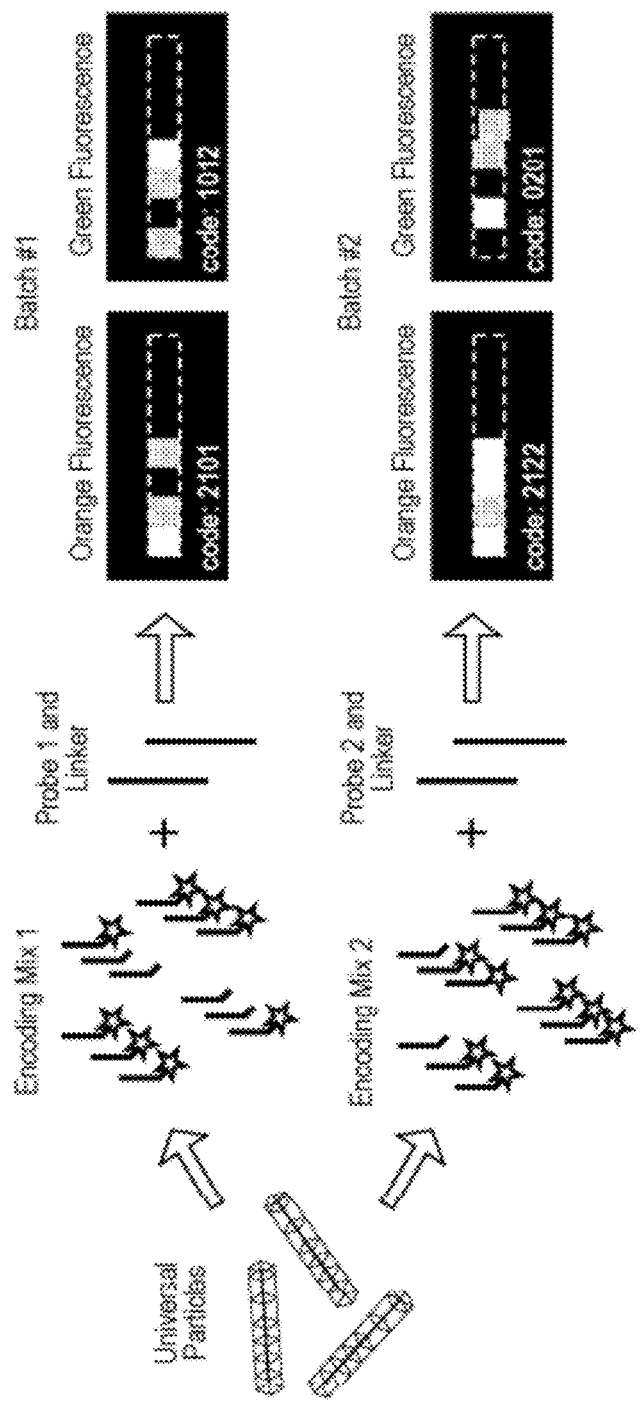
FIG. 2 illustrates an exemplary schematic for universal encoding using multiple fluorophores. Multiple adapter variants may be used, each with unique emission spectrum, to encode particles or substrates with more than one color (or otherwise functional species). The level of each color can be modulated by adjusting the ratio of each adapter variant to give unique signatures of multiple fluorescent colors in the coding regions of the particles.

A substrate used in accordance with the present invention can comprise one or more probe-bearing regions in addition to encoding regions. Two typical schematics for universal encoding and probe functionalization are represented in FIG. 1 and FIG. 2.

Figure 3:
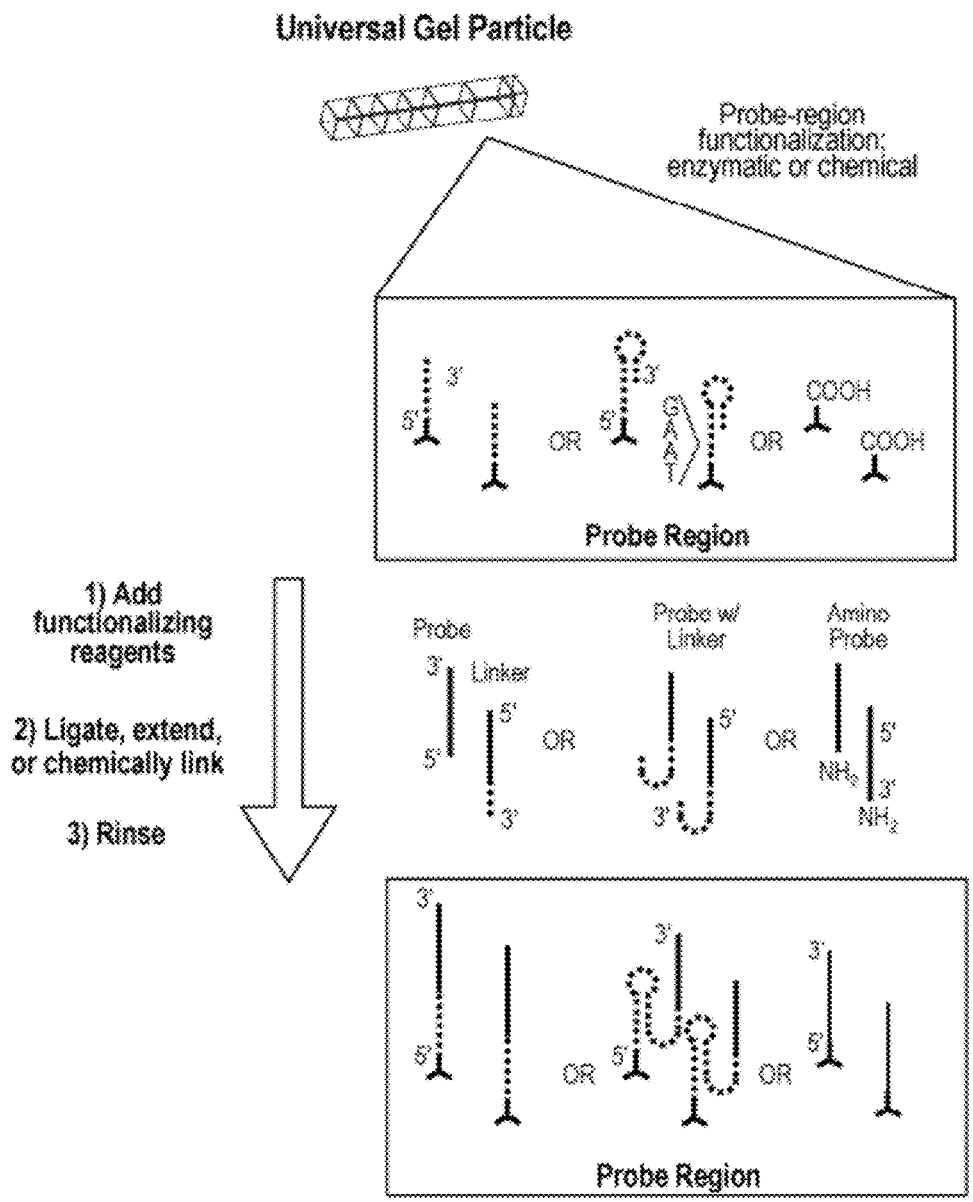
FIG. 3 illustrates an exemplary schematic of probe-region functionalization using three-species ligation, two-species ligation, and chemical modification.

In some embodiments, each probe region bears anchors for attaching probes of interest via, e.g., ligation-based approach. Ligation can be performed with three species (anchor, linker, and probe) or two species (hairpin anchor and probe). A schematic of probe-region functionalization using three-species ligation, two-species ligation, and chemical modification is depicted in FIG. 3.

In some embodiments, probe region functionalization includes chemical modification, such as the use of peptide chemistry to attach aminated probes to carboxylated substrates using carbodiimide chemistry. Detailed exemplary methods for functionalization are shown in the Examples section below.

Desired probes specific for target nucleic acids may be designed using various methods known in the art. In some embodiments, desired probes for probe region functionalization include nucleic acid probes for post-hybridization labeling described herein.

In some embodiments, probe regions and encoding regions are separated from one another by inert regions. In some embodiments, one or more probe-bearing regions and one or more encoding regions overlap with each other. In some embodiments, an encoding and probe-bearing region can be the same region.

In some embodiments, different detectable signals (e.g., different fluorescent colors) may be used for encoding regions and probe-bearing regions. In some embodiments, same type of detectable signals are used, in particular, when encoding regions and probe-bearing regions are separated from each other.

For two-species functionalization, it is possible to use linear anchors and adapters that have hairpins. The adapter and anchor species may be designed to have minimal hairpin formation in ligation conditions or vary tightly bound hairpins. Detectable moieties for encoding may include fluorophores, chromophores, radioactive species, magnetic species, quantum dots, conductive materials, etc. Any number of coding regions may be used, and they need not be stripes. Any number of colors or otherwise distinguishable signals may be included in each encoding region. This approach may be used with other substrates including beads, planar surfaces, gel pads, etc. The substrates may be solid, polymer, emulsions, etc.

Figure 4:
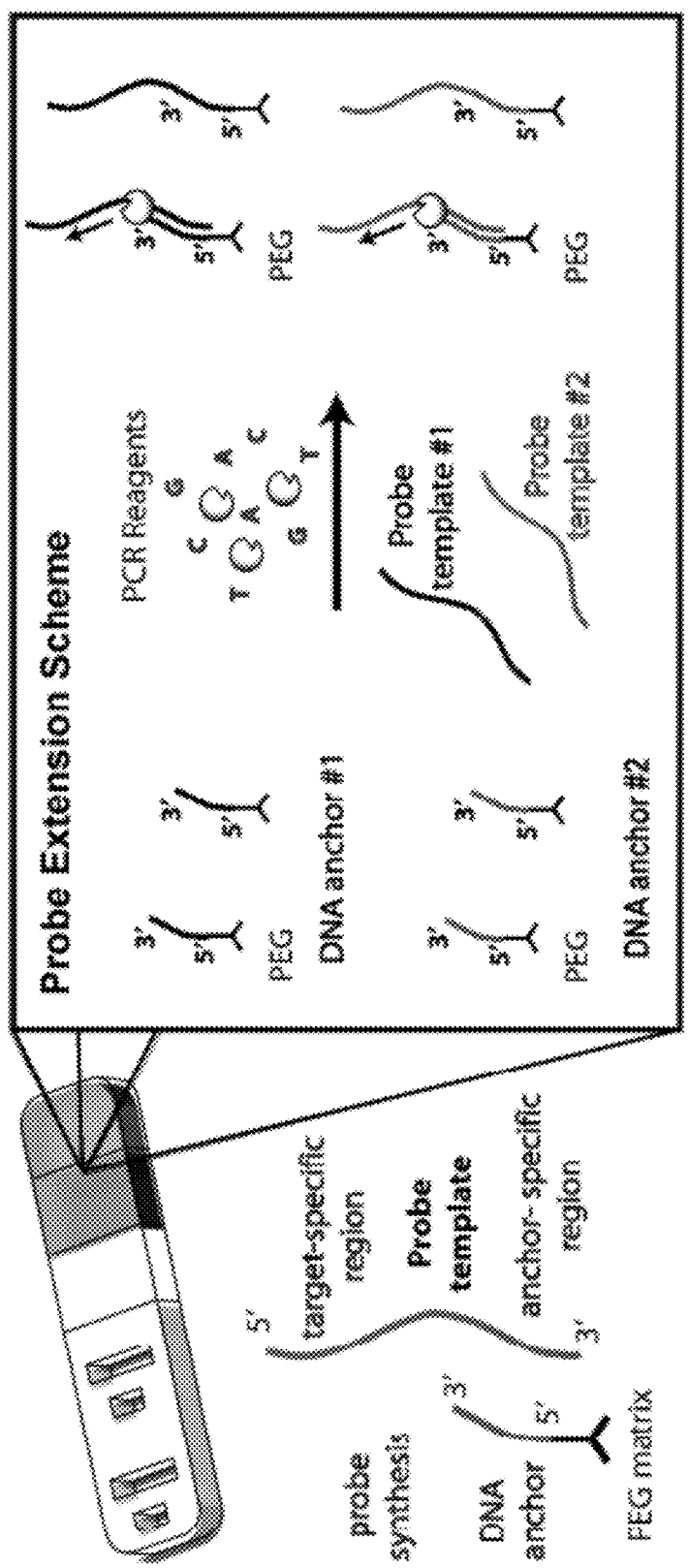
FIG. 4 illustrates an exemplary schematic showing the use of polymerase with probe-specific templates to add functionality to particles or substrates. Universal anchors (in this case there are two different anchors) are used with linkers that bear a region specific for one anchor and a probe sequence. Polymerases are used to extend the anchors along the linker, functionalizing the particles/substrates in one or multiple regions.

In addition to ligation based approach, inventive methods for universal encoding and/or functionalization can be implemented with other enzymes including ligases, polymerases, among others. For example, although T4 DNA ligase was used in the experiments described below, it is possible to use other enzymes to join oligonucleotides together. Other possible enzymes include, but are not limited to, other DNA ligases, RNA ligases, polymerases, etc. In a slightly different approach, polymerases can also be used to extend oligonucleotides, using a desired nucleic acid template, as means of adding nucleic acid probes for functionalization or labeled species for encoding or detection (FIG. 4). Using this approach or ligation-based approaches, multiple probe regions can be added to a single particle when multiple probe "anchors" are used.

Target Nucleic Acids

Methods and compositions described herein may be used to detect any target nucleic acids. In general, target nucleic acids may be any form of DNA, RNA, or any combination thereof. In certain embodiments of the present invention, a target nucleic acid may be or contain a portion of a gene, a regulatory sequence, genomic DNA, cDNA, RNA including mRNA, rRNA, microRNA, or any combination thereof.

A target nucleic acid, in various embodiments, can be one that is found in a biological organism including, for example, a microorganism or infectious agent, or any naturally occurring, bioengineered or synthesized component thereof.

According to the present invention, provided compositions and methodologies are particularly useful in quantifying transcript (e.g., primary transcripts, mRNA, etc.) nucleic acids. In some embodiments, provided methods herein are used to detect and/or quantify miRNAs. miRNAs can be found in genomes of humans, animals, plants and viruses. According to the present invention, a target nucleic acid, in some embodiments, can be or comprise one or more miRNAs that is/are generated from endogenous hairpin-shaped transcripts. In some embodiments, a target nucleic acid can be or comprise one or more miRNAs that is/are transcribed as long primary transcripts (pri-microRNAs), for example, by RNA polymerase II enzyme in animals. There are total 1424 human miRNA genes currently listed in the miRNA database (http://microrna.sanger.ac.uk/sequences/ftp.shtml), which is equivalent to almost 3% of protein-coding genes. Many miRNAs are thought to be important in the regulation of gene expression. Typically, microRNAs are produced in precursor form and then processed to mature form by typically cleaving the 3' arm of the precursor stem-loop structure. Therefore, a precursor microRNA and a mature microRNA have identical 5' end but distinct 3' end. Selective end-labeling can be used to detect mature microRNA species without detection of precursor species by designing a capturing sequence complementary to the 3' end sequence. An example of selective end-labeling is described in the examples section.

Any of a variety of biological samples may be suitable for use with methods disclosed herein. Generally, any biological samples containing nucleic acids (e.g., cells, tissue, etc.) may be used. Types of biological samples include, but are not limited to, cells, tissue, whole blood, plasma, serum, urine, stool, saliva, cord blood, chorionic villus samples amniotic fluid, and transcervical lavage fluid. Tissue biopsies of any type may also be used. Cell cultures of any of the aforementioned biological samples may also be used in accordance with inventive methods, for example, chorionic villus cultures, amniotic fluid and/or amniocytes cultures, blood cell cultures (e.g., lymphocyte cultures), etc. In some embodiments, biological specimens comprise diseased cells such cancer or tumor cells.

Thus, a typical biological sample suitable for the present invention contain heterogeneous nucleic acids. In some embodiments, a biological sample contains a mixture of nucleic acids from different cell types (e.g., normal cells and diseased cells such as tumor cells). In some embodiments, a biological sample (e.g., blood, serum or plasma) contains a mixture of maternal nucleic acids and fetal nucleic acids.

In some embodiments, the present invention is used to detect target nucleic acids that are present in low abundance or as rare events in a biological sample. In some embodiments, target nucleic acids that may be detected by an inventive method of the present invention are present at a concentration ranging from 0.1 amol-10,000 amol. In some embodiments, the target nucleic acids are present at a concentration below 10,000 amol, below 5,000 amol, below 1,000 amol, below 800 amol, below 600 amol, below 400 amol, below 200 amol, below 100 amol, below 50 amol, below 40 amol, below 30 amol, below 20 amol, below 10 amol, or below 1 amol. In some embodiments, the amount of target nucleic acids detected by an inventive method of the present invention represents less than 1% (e.g., less than 0.5%, 0.1%, 0.01%, 0.001%, 0.0001%) of the total nucleic acids in a biological sample. In some embodiments, the amount of target nucleic acids detected by an inventive method of the present invention represents less than 1% (e.g., less than 0.5%, 0.1%, 0.01%, 0.001%, 0.0001%) of the total nucleic acids in a biological sample. In some embodiments, the amount of target nucleic acids detected by an inventive method of the present invention represents less than 1 out of a million of the total nucleic acids in a biological sample. In some embodiments, the amount of target nucleic acids detected by an inventive method of the present invention represents less than 1 out of 10 million of the total nucleic acids in a biological sample. The target nucleic acids may be detected in crude sample or may be detected as isolated or purified sample.

Scanning and Quantification

Substrates or objects described herein may be characterized using various methods. In particular, various methods involving flow-through scanning and/or static imaging can be used to detect substrates bound with target nucleic acids and/or to determine amount of the target nucleic acids. Typically, target nucleic acids attached to substrates are determined based on detection of signals. According to the present invention, signals "indicative of" a target nucleic acid are typically associated with the identity of substrates or locations on substrates to which the target nucleic acid is attached. For example, signals emanate from one or more detectably labeled probes or targets that becomes associated with signals indicative of one or more encoding regions of the substrates bearing the probes or targets.

Figure 5:
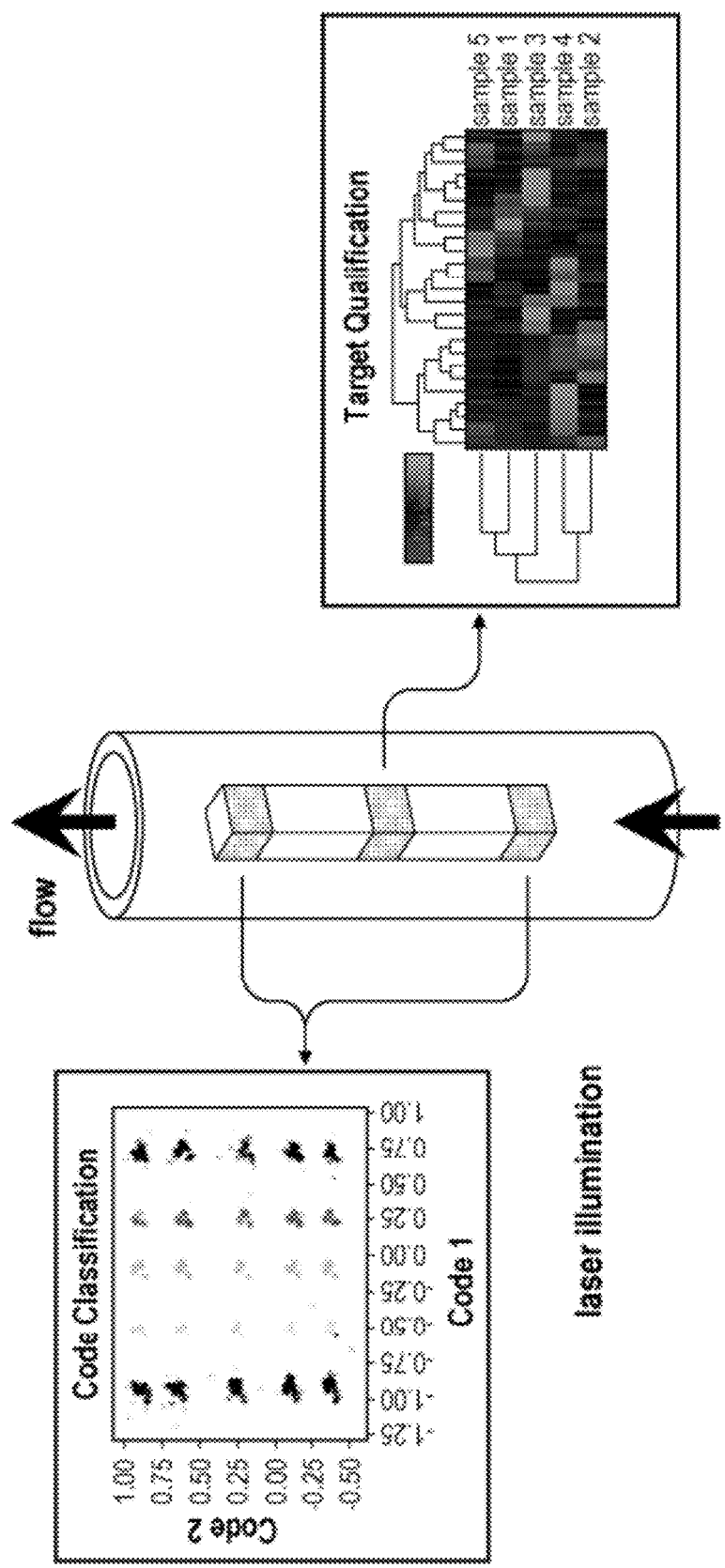
FIG. 5 illustrates an exemplary schematic of multi-color scanning with a flow cytometer.

In some embodiments, signals indicative of target nucleic acids are generally distinguishable from signals indicative of identity of substrates. In some embodiments, probes or universal adapters specific for a target nucleic acid and encoding adapters for coding regions are labeled with distinctively detectable signals. For example, probes or universal adapters specific for the target nucleic acid may be labeled with fluorescent moieties that have a different emission spectrum (i.e., color and wavelength) than that of the fluorescent moieties with which the coding regions are labeled. Thus, in some embodiments, substrates (e.g., particles) of the present invention can be scanned using a multi-scanning system involving more than one excitation sources and detectors (see FIG. 5).

Figure 6:
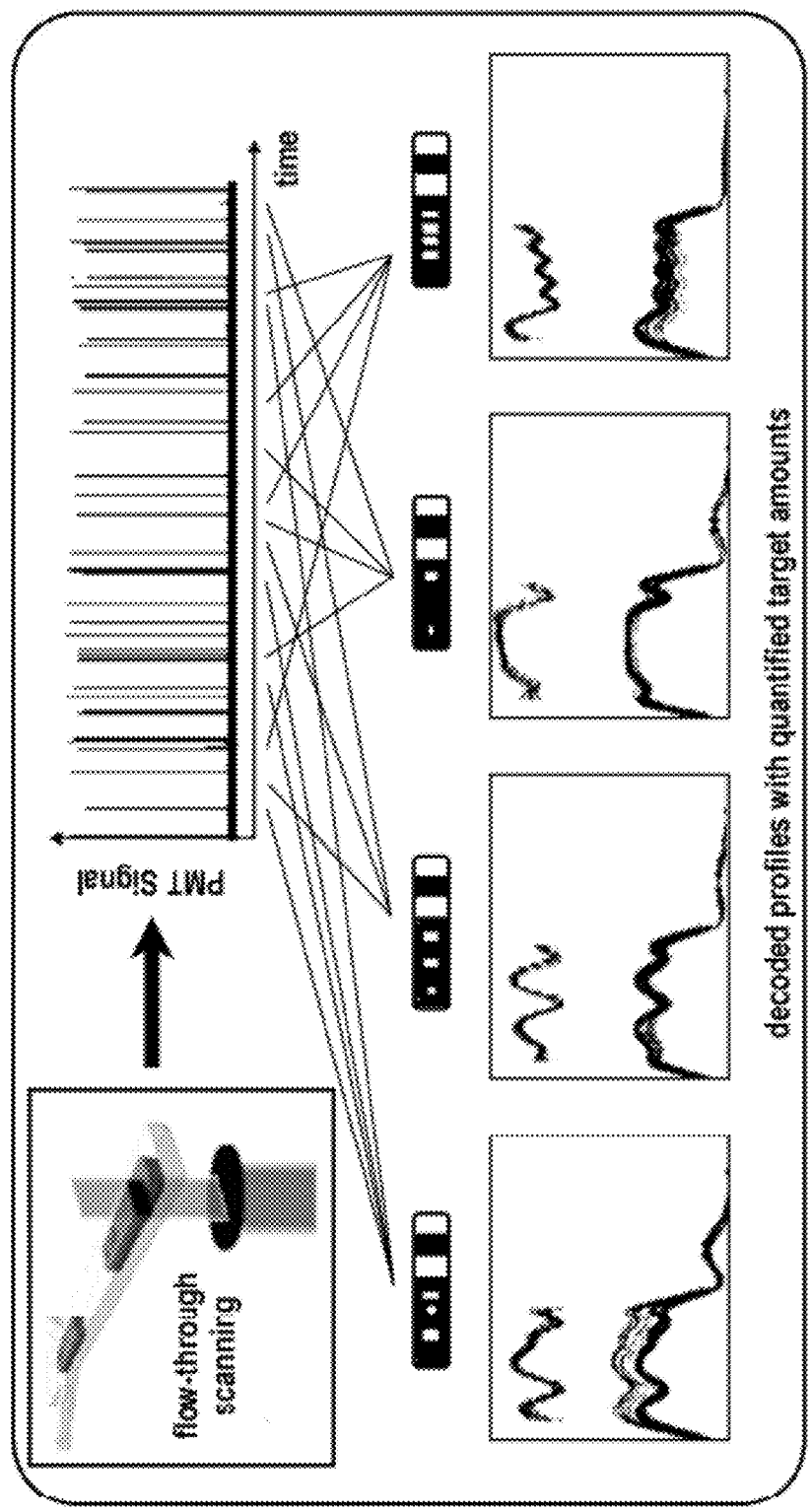
FIG. 6 illustrates an exemplary schematic of single-color scanning with a flow-through device.

In some embodiments, single-color scanning is used. Signals indicative of separate "code" and "probe" regions are used to identify substrates (e.g., particles) and capture targets, respectively. Using particles as examples, as described in detail below, signal patterns from the code regions (e.g., bearing holes, stripes, encoding adapters and/or combination thereof) of a particle serve as the basis for a graphical multiplexing barcode to identify the probe(s) in a particular particle. In some embodiments, unlike traditional bead-based systems that use optical encoding of spheres, an arrangement in which particles have multiple distinct regions makes single-color scanning possible, with only one excitation source and one detector required. In some embodiments, particles can bear graphical features (e.g., stripes, holes, or the like) with variable fluorescent intensities (of one or multiple wavelengths), optical properties, dimensions, etc (see FIG. 6).

Particles are used as examples to illustrate the scanning and quantification process in more detail below. However, methods described herein may be used with various other types of substrates or objects.

Interrogating Particles

In some embodiments, the present invention provides a method for characterizing multifunctional objects (e.g., particles) including one or more steps of (a) interrogating a plurality of objects (e.g., particles), wherein each individual object (e.g., particle) containing one or more interrogation regions detectable as a sequence of events; (b) recording multiple events, wherein each individual event corresponds to each individual interrogation region detectable above a predetermined triggering threshold; (c) grouping the recorded multiple events, and (d) characterizing the plurality of objects based on the grouped events.

In some embodiments, particles are interrogated using image analysis in either static or flow-through settings. For high-throughput applications, it is desirable to scan the particles rapidly, preferably using existing commercial equipment. For example, flow cytometers are particularly useful for flow-through analysis of fluorescently labeled beads and particles, providing means for particle alignment, precise illumination, and accurate quantification of fluorescence emission. In some embodiments, encoded multifunctional particles are designed such that they can be scanned using commercially-available or custom designed flow-through device, such as, flow cytometers.

In some embodiments, particles suitable for flow-through scanning are engineered to mimic a series of cells (e.g., 2, 3, 4, 5, or more) that flow past an interrogation zone. In particular embodiments, outer regions (e.g., both end regions) of suitable particles are coding regions while one or more inner regions contain probes where the target is captured. Each coding region and probe region can be interrogated separately (e.g., sequentially or non-contemporaneously) and each region is also referred to as an interrogation region. In particular embodiments, rod-shaped particles that bear multiple interrogation regions are recorded as "events" using standard cytometery signal processing. By analyzing the sequence and time-proximity of such events, one can infer which ones belong in the same particle. These events can then be analyzed to decode the particle and quantify target bound to the probe region. Signal quantification can be achieved using fluorescence, light scattering, luminescence, etc.

Typically, raw signal is obtained from the cytometer detectors (or signal processing boards) using standard cytometery software. The signal can then be processed using custom software to import standard flow cytometery (FCS) files and reconstruct the events into particles and corresponding probe and coding regions.

Various flow-cytometry and other flow-through reading devices may be used in accordance with the present invention, including various commercially available flow-cytometers and customly designed devices. Exemplary suitable flow cytometers include, but are not limited to, Millipore Guava 8HT, Guava 5HT, Accuri C6, BD FACSCalibur, and among other cytometers.

Multiple-Event Particles

As a non-limiting example, when a particle travels through a cytometer's flow cell, it is excited with an illumination spot while detectors are used to monitor several parameters including forward scatter and side scatter of the illumination, and various wavelengths of emitted light. By setting a threshold on one of these parameters in a triggering channel, a user can define the instances that the cytometer software will record as events. If the signal from the detector in the triggering channel increases beyond the threshold level set by the user, the cytometery hardware and software will start to record an event—measuring the maximum signal height and integrated area from each detector while the triggering signal remains above the threshold. Events are typically reported with the height and area observed in each channel, along with the event width and a time-stamp of when the event occurred.

Typically, a single particle or bead is recorded as a single event. However, in many embodiments, particles according to the invention (e.g., rod-shaped particles) with multiple functional regions can be read as a sequence of distinct events. This is accomplished by using particles that have functional regions (for example: fluorescent) separated by inert regions (for example: non fluorescent). By incorporating threshold-triggering entities in the functional regions of the particles, but not in the inert regions, typical cytometry signal processing software records the functional regions as discrete events. This can be accomplished using entities that cause scatter or fluorescence. Such entities could include microparticles, nanoparticles, reflective monomers, metallic materials, fluorescently-labeled monomers, quantum dots, fluorescent dyes, carbon nanotubes, liquid crystals, and various detectable entities described herein.

An example is provided in the Examples section to illustrate how this approach works and the distinction from standard cytometry (Example 9). A example of particle scanning using a particular flow cytometery is provided in Example 10.

Data Analysis

For data analysis, an algorithm can be written to group events into particles, orients the particles, normalizes fluorescence against a standard if desired, and quantifies the fluorescence, scatter, or event width in each code and probe region. The corresponding code for each particle can then be given a confidence level, and those that were not called with a pre-defined level of confidence can be excluded from the analysis. The fluorescence in the probe region can then be used to determine the amount of target present in the sample analyzed. This system can be easily automated using software that performed analysis during or after scanning.

Grouping of Events

In some embodiments, events are grouped based on spatial and temporal-proximity. In some embodiments, events are grouped based on patterns of measured properties for each event.

Typically, each event recorded by the cytometer is given a timestamp with a pre-determined resolution of, e.g., 1 ms, based on the flow rate in each cytometery. For example, as particles typically move at rates of ~1 m/s through the flow cell, the interrogation of a particle that is 200 μm long is expected to last ~0.2 ms. As such, it can be expected that the two events recorded from a single multifunctional particle would appear in the same timestamp.

In some embodiments, calibration beads are scanned fairly randomly throughout the course of data acquisition. Typically, at least one event is recorded for calibration beads. The multifunctional particles, on the other hand, typically show clustering of 2 or 4 events per timestamp, which lends very well to the theory that each particle is being read as two events. In addition, it can be clearly seen from the plots of event vs. time that during each timestamp, there is a high- and low-level fluorescence reading. The particles were designed to have one bright and one dim region of fluorescence in the FL-2 channel, which also gives support to the theory that each particle is being read as two discrete events. This approach can be applied to three or more events per particle as well. Each region/event can vary in terms of fluorescence level, forward or side scatter, and width.

It is possible to incorporate distinct levels of multiple fluorophores into each code region of the multifunctional particles. As a proof-of-concept, we used rod-shaped particles, 200×35×30 μm, with a single 60 μm code region on one end.

The code region was labeled using four distinct levels of Cy3 and Cy5 fluorescent dyes. Particles were analyzed using the Accuri C6 cytometer with a flow rate of 100 μl/min, a core size of 40 μm, and a threshold of 5000 on FL4. The results are shown in FIG. 7.

Figure 7:
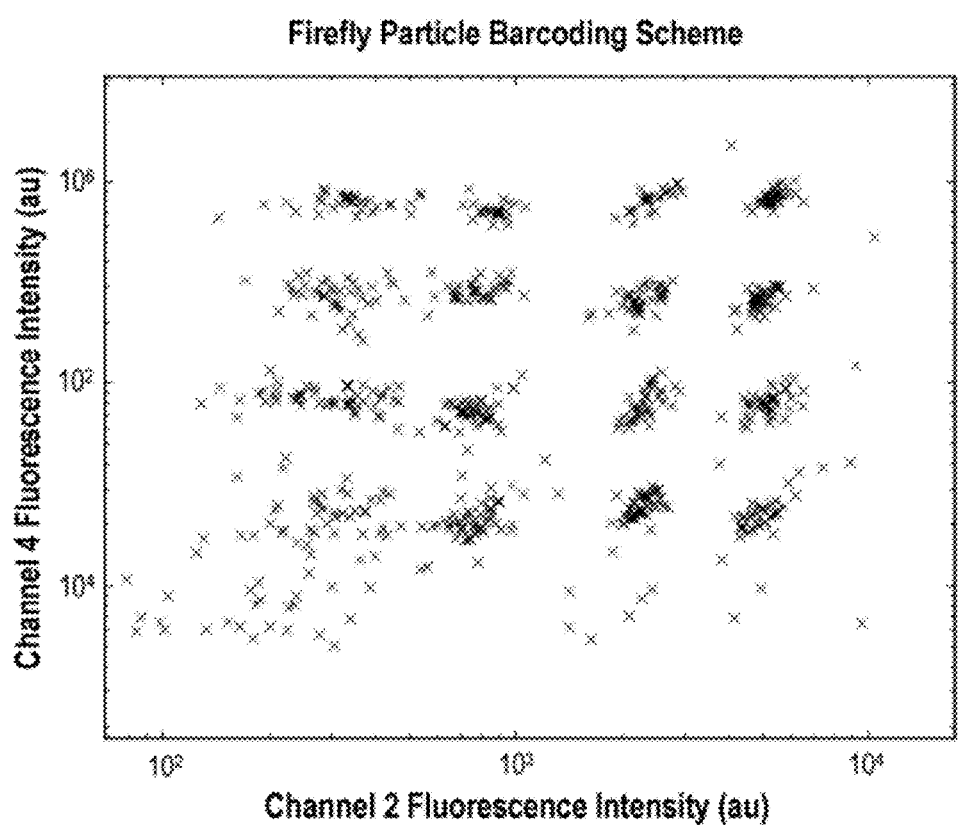
FIG. 7 illustrates an exemplary fluorescence scatter plot for multifunctional particles with a single code region functionalized with four distinct levels of Cy3 (shows in Channel 2) and Cy5 (Channel 4).

The plot in FIG. 7 shows that it is possible to create a distinct fluorescent fingerprint in each code region of multifunctional particles. Each cluster of data points represents a distinct code.

Reading of Raw Signal

In some embodiments, interrogating multifunctional particles in standard flow cytometers is to acquire signal from the cytometer detectors before it is processed into events by the machine's firmware and use custom software to identify, orient, and analyze particles scans.

In some embodiments, raw data files (e.g., 20 million points/scan) produced by the scanning process are analyzed with a custom written MATLAB algorithm designed to isolate individual particle signatures, identify the code displayed by each particle, and quantify the amount of target bound. The algorithm processed scans of 50-μl samples in under 5 s, making the approach suitable for high-throughput applications. In the initial filter step, the algorithm excised portions of the scan that exceeded a threshold voltage and then interrogated each removed segment for characteristics that identified it as a particle signature. Using specific properties of the fluorescent code region as reference points, a high-confidence estimate of the velocity of each particle was determined and utilized to pinpoint trough locations for the five coding holes. The orientation of the particle (i.e., probe- or code-first) was established using the fixed-value "3" hole that bordered the inert buffer region. After an initial code identity was calculated from the trough depths, a secondary review was conducted by measuring the standard deviation in trough depths of holes designated to be of the same level and corrective action was taken if necessary. In the final decoding step, a confidence score was calculated for the particle by computing the linearity of the correlation between trough depth and assigned level. A particle decoding event was rejected if its Pearson coefficient fell below 0.97.

In order to calculate the amount of target bound, the measured particle velocity was used to infer the location of the center of the probe region. Briefly, a search window was used to investigate the scan in this region, seeking to identify a local maximum that could be correlated to a target-binding event. If a maximum was found, the position of the search window along the scan profile was adjusted until the two endpoints were sufficiently close in signal amplitude, thereby selecting a nearly symmetrical portion of the maximum over which to average for quantification purposes. In the cases in which a maximum was not found, the original estimate of probe center was used to calculate a mean signal without a search window. To calculate the background for a given probe sequence and incubation condition, particles from the same synthesis batch were incubated in the presence of, e.g., only 100 amol of miSpike target according to the procedure described above. This method provided a measure of the probe-dependent background that arose from the PEG scaffold and the universal adapter used in the labeling process. Also, upon calculation of all code identities and target levels, a particle would be rejected from consideration if its target level was more than one inter-quartile range above the third quartile or below the first quartile of the data set consisting of target levels associated with the probe in question.

Various examples of particle scanning and quantification are provided in the Examples section. Additional scanning and quantification methods are described in International application entitled "Scanning Multifunctional Particles," filed on even date, the disclosure of which is incorporated herewith in its entirety.

Other Embodiments

There are several variations and alternate approaches to the embodiments described above. Although rod-shaped particles are used as examples described here, the present invention may be used to scan objects or particles with many other morphologies as well. For instance, particles may be anisotropic, have a head on one side, include rounded shapes, have holes in them, etc. In some embodiments, the present invention may be used to scan a variety of multifunctional entities including long nucleic acids, DNA origami, self-assembled structures, biological organisms, string-like objects, ribbon-like objects, etc. Furthermore, any combination of information recorded by the cytometer for each event, including height, area, width, or any combination thereof can be used for encoding or target quantification.

Other commercially-available instruments are capable of reading particles with multiple functional regions and can be used to practice the present invention. One example is an instrument capable of measuring changes in electrical conductance, or electrical resistance of a fluidic channel such as a Coulter Counter. The resulting current or voltage generated by a particle by a detector in such systems can be used to characterize particle size, shape, chemical composition, or surface properties. Additionally, laser-scanning cytometry (LSC), which allows high resolution visualization of particles in flow, may be used to identify the identifier regions and probe regions on particles with several functionalized regions. Such LSC systems are commercially available from companies such as CompuCyte. There also exist commercial cytometers that image cells/particles as they pass (eg. Amnis ImageStream). These can be used with suitable image-processing software to decode particles and quantify target. In addition, it may be possible to use non-fluorescent means of quantification such as surface-plasmon resonance or radiation.

Applications

The present invention has many applications, including, but not limited to, diagnosis and prognosis of diseases, disorders or conditions based on detection or quantification of a target nucleic acid (e.g., microRNA, DNA or mRNA) in a biological sample.

Those of ordinary skill reading the present disclosure, will appreciate its broad applicability. For example, the present invention can be used to diagnose or prognose a variety of diseases including, but not limited to, cancer (e.g., lung cancer, breast cancer, stomach cancer, pancreatic cancer, lymphoma, leukemia, colon cancer, liver cancer, etc.), diabetes, neurodegenerative diseases (e.g., Alzheimer's), infectious diseases, genetic diseases.

Representative bacterial infectious agents which can be detected and/or determined by the present invention include, but are not limited to, *Escherichia coli, Salmonella, Shigella, Klebsiella, Pseudomonas, Listeria monocytogenes, Mycobacterium tuberculosis, Mycobacterium aviumintracellulare, Yersinia, Francisella, Pasteurella, Brucella, Clostridia, Bordetella pertussis, Bacteroides, Staphylococcus aureus, Streptococcus pneumonia,* B-Hemolytic strep., *Corynebacteria, Legionella, Mycoplasma, Ureaplasma, Chlamydia, Neisseria gonorrhea, Neisseria meningitides, Hemophilus influenza, Enterococcus faecalis, Proteus vulgaris, Proteus mirabilis, Helicobacter pylori, Treponema palladium, Borrelia burgdorferi, Borrelia recurrentis, Rickettsial pathogens, Nocardia,* and *Acitnomycetes.*

Representative fungal infectious agents which can be detected and/or determined by the present invention include, but are not limited to, *Cryptococcus neoformans, Blastomyces dermatitidis, Histoplasma capsulatum, Coccidioides immitis, Paracoccidioides brasiliensis, Candida albicans, Aspergillus fumigautus, Phycomycetes (Rhizopus), Sporothrix schenckii, Chromomycosis,* and *Maduromycosis.*

Representative viral infectious agents which can be detected and/or determined by the present invention include, but are not limited to, human immunodeficiency virus, human T-cell lymphocytotrophic virus, hepatitis viruses (e.g., Hepatitis B Virus and Hepatitis C Virus), Epstein-Barr Virus, cytomegalovirus, human papillomaviruses, orthomyxo viruses, paramyxo viruses, adenoviruses, corona viruses, rhabdo viruses, polio viruses, toga viruses, bunya viruses, arena viruses, rubella viruses, and reo viruses.

Representative parasitic agents which can be detected and/or determined by the present invention include, but are not limited to, *Plasmodium falciparum, Plasmodium malaria, Plasmodium vivax, Plasmodium ovale, Onchoverva volvulus, Leishmania, Trypanosoma* spp., *Schistosoma* spp., *Entamoeba histolytica, Cryptosporidium, Giardia* spp., *Trichimonas* spp., *Balatidium coli, Wuchereria bancrofti, Toxoplasma* spp., *Enterobius vermicularis, Ascaris lumbricoides, Trichuris trichiura, Dracunculus medinesis,* trematodes, *Diphyllobothrium latum, Taenia* spp., *Pneumocystis carinii,* and *Necator americanis.*

The present invention can also be useful for detection and/or determination of drug resistance by infectious agents. For example, vancomycin-resistant *Enterococcus faecium,* methicillin-resistant *Staphylococcus aureus,* penicillin-resistant *Streptococcus pneumoniae,* multi-drug resistant *Mycobacterium tuberculosis,* and AZT-resistant human immunodeficiency virus can be identified with the present invention.

Genetic diseases can also be detected and/or determined by the process of the present invention. This can be carried out by prenatal or post-natal screening for chromosomal and genetic aberrations or for genetic diseases. Examples of detectable genetic diseases include, but are not limited to: 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia, Tay-Sachs Disease, thalassemia, Klinefelter Syndrome, Huntington Disease, autoimmune diseases, lipidosis, obesity defects, hemophilia, inborn errors of metabolism, and diabetes.

Cancers which can be detected and/or determined by the process of the present invention generally involve oncogenes, tumor suppressor genes, or genes involved in DNA amplification, replication, recombination, or repair. Examples of these include, but are not limited to: BRCA1 gene, p53 gene, APC gene, Her2/Neu amplification, Bcr/Ab1, K-ras gene, and human papillomavirus Types 16 and 18. Various aspects of the present invention can be used to identify amplifications, large deletions as well as point mutations and small deletions/insertions of the above genes in the following common human cancers: leukemia, colon cancer, breast cancer, lung cancer, prostate cancer, brain tumors, central nervous system tumors, bladder tumors, melanomas, liver cancer, osteosarcoma and other bone cancers, testicular and ovarian carcinomas, head and neck tumors, and cervical neoplasms.

In the area of environmental monitoring, the present invention can be used, for example, for detection, identification, and monitoring of pathogenic and indigenous microorganisms in natural and engineered ecosystems and microcosms such as in municipal waste water purification systems and water reservoirs or in polluted areas undergoing bioremediation. It is also possible to detect plasmids containing genes that can metabolize xenobiotics, to monitor specific target microorganisms in population dynamic studies, or either to detect, identify, or monitor genetically modified microorganisms in the environment and in industrial plants.

The present invention can also be used in a variety of forensic areas, including, for example, for human identification for military personnel and criminal investigation, paternity testing and family relation analysis, HLA compatibility typing, and screening blood, sperm, or transplantation organs for contamination.

In the food and feed industry, the present invention has a wide variety of applications. For example, it can be used for identification and characterization of production organisms such as yeast for production of beer, wine, cheese, yoghurt, bread, etc. Another area of use is with regard to quality control and certification of products and processes (e.g., livestock, pasteurization, and meat processing) for contaminants. Other uses include the characterization of plants, bulbs, and seeds for breeding purposes, identification of the presence of plant-specific pathogens, and detection and identification of veterinary infections.

EXAMPLES

Example 1

Particles Synthesis

This example demonstrates that various particles can be synthesized for use according to the present invention. Exemplary methods are described in detail below.

Exemplary particle batches were synthesized in 38-μm tall polydimethylsiloxane (PDMS) microfluidic channels with the stop-flow lithography method. For the 12-plex study, code and inert buffer regions were polymerized from monomer solutions with 35% (v/v) poly(ethylene glycol) diacrylate (MW=700 g/mol) (PEG-DA 700), 20% poly(ethylene glycol) (MW=200 g/mol) (PEG 200), 40% 3× Tris-EDTA (TE) buffer (pH 8.0), and 5% Darocur 1173 photoinitiator. 1×TE and rhodamine-acrylate (1 mg/ml) were added to code monomer to give final concentrations of 9.4% and 0.6%, respectively. 1×TE and blue food coloring were added to buffer monomer to give final concentrations of 8.0% and 2.0%, respectively. Food coloring was used to visualize stream widths. Probe regions were polymerized from a different monomer solution that was added to acrydite-modified DNA probe sequences (Integrated DNA Technologies, IDT) suspended in 1×TE to give the desired final concentration of probe, 18% (v/v) PEG-DA 700, 36% PEG 200, and 4.5% Darocur; the remaining balance consisted of 3×TE.

In an effort to coarsely rate-match the binding of the targets used in this exemplary study, we incorporated the probe sequences at different concentrations in the particles (Table 1). As the characteristic time for target depletion scales with the inverse square root of probe concentration, a doubling of the binding rate for a given target will require a 4× increase in the amount of probe incorporated in a probe region of fixed size. In this exemplary study all rates were adjusted to match that of let-7a binding. Without being bound to any particular theory, it is contemplated that higher sensitivities and shorter assays could have been achieved by loading probe at maximum concentration. In this particular case, the goal was to develop a 12-plex assay with broad dynamic range and ~1 amol sensitivity for all targets.

TABLE 1

Exemplary particle codes and probe information for batches synthesized for 12-plex study. Final composition (v/v) of PEG-DA 700, PEG 200, and Darocur 1173 photoinitiator in prepolymer stream for probe were fixed at 18, 36, and 4.5%, respectively. Hairpin melting temperatures are listed in descending order, as calculated for the DNA-RNA duplex by IDT's OligoCalc application for the incubation conditions used in this exemplary study. For each miRNA, the relative binding rate was calculated using the average of target signals from 30- and 60-min incubations with 500 amol of target and ligation labeling. Short incubations were chosen to ensure the system had not reached equilibrium. Quoted probe concentrations refer to prepolymer stream composition. Approximately 11% of the probe in the prepolymer stream was covalently incorporated into the particles (Pregibon, D.C. et al., *Anal. Chem.* 81, 4873-4881 (2009)).

| Target | Probe Sequence | Hairpin Melting Temps (° C.) | Binding Rate Relative to let-7a for Probe Conc. of 50 μM | Adjusted Probe Concentration (μM) | Identifying Codes |
|---|---|---|---|---|---|
| let-7a | 5Acryd/GAT ATA TTT TAA ACT ATA CAA CCT ACT ACC TCA/3InvdT (SEQ ID NO: 1) | 38.0 | 1.00 | 50 | 31131, 32231, 31231, 32131, 31031 |
| miR-21 | 5Acryd/GAT ATA TTT TAT CAA CAT CAG TCT GAT AAG CTA/3InvdT (SEQ ID NO: 2) | 60.4, 52.9, 49.3, 46.6 | 0.45 | 247 | 31112, 32212, 31212, 32112, 31312 |
| miR-29b-2 | 5Acryd/GAT ATA TTT TAA ACA CTG ATT TCA AAT GGT GCT A/3InvdT (SEQ ID NO: 3) | 45.9, 44.7, 41.7 | 0.63 | 126 | 31132, 32232, 31232, 32132, 31032 |

TABLE 1-continued

Exemplary particle codes and probe information for batches synthesized for 12-plex study. Final composition (v/v) of PEG-DA 700, PEG 200, and Darocur 1173 photoinitiator in prepolymer stream for probe were fixed at 18, 36, and 4.5%, respectively. Hairpin melting temperatures are listed in descending order, as calculated for the DNA-RNA duplex by IDT's OligoCalc application for the incubation conditions used in this exemplary study. For each miRNA, the relative binding rate was calculated using the average of target signals from 30- and 60-min incubations with 500 amol of target and ligation labeling. Short incubations were chosen to ensure the system had not reached equilibrium. Quoted probe concentrations refer to prepolymer stream composition. Approximately 11% of the probe in the prepolymer stream was covalently incorporated into the particles (Pregibon, D.C. et al., Anal. Chem. 81, 4873-4881 (2009)).

| Target | Probe Sequence | Hairpin Melting Temps (° C.) | Binding Rate Relative to let-7a for Probe Conc. of 50 μM | Adjusted Probe Concentration (μM) | Identifying Codes |
|---|---|---|---|---|---|
| miR-181b-1 | 5Acryd/GAT ATA TTT TAA CCC ACC GAC AGC AAT GAA TGT T/3InvdT (SEQ ID NO: 4) | 58.4, 43.2, 38.6 | 0.89 | 63 | 32230, 31130, 31230 32130, 31030 |
| miR-143 | 5Acryd/GAT ATA TTT TAG AGC TAC AGT GCT TCA TCT CA/3InvdT (SEQ ID NO: 5) | 55.2, 51.1 | 1.04 | 50 | 31110, 32210, 31210 32110, 31310 |
| miR-145 | 5Acryd/GAT ATA TTT TAA GGG ATT CCT GGG AAA ACT GGA C/3InvdT (SEQ ID NO: 6) | 47.4, 43.0, 36.6 | 1.01 | 50 | 31121, 32221, 31221 32121, 31321 |
| miR-146a | 5Acryd/GAT ATA TTT TAA ACC CAT GGA ATT CAG TTC TCA/3InvdT (SEQ ID NO: 7) | 64.6, 49.4, 48.3, 43.4 | 0.67 | 111 | 30001, 31101, 32201 31201, 32101 |
| miR-210 | 5Acryd/GAT ATA TTT TAT CAG CCG CTG TCA CAC GCA CAG/3InvdT (SEQ ID NO: 8) | 68.4, 65.6, 59.7, 55.4 | 0.90 | 62 | 31122, 32222, 31222 32122, 31322 |
| miR-221 | 5Acryd/GAT ATA TTT TAG AAA CCC AGC AGA CAA TGT AGC T/3InvdT (SEQ ID NO: 9) | 49.8, 43.6 42.2, 41.0 | 0.82 | 62 | 31111, 32211, 31211 32111, 31311 |
| miR-222 | 5Acryd/GAT ATA TTT TAA CCC AGT AGC CAG ATG TAG CT/3InvdT (SEQ ID NO: 10) | 68.2, 68.1, 58.1, 47.5 | 0.62 | 130 | 31120, 32220, 31220 32120, 31320 |
| miSpike | 5Acryd/GAT ATA TTT TAA GAC CGC TCC GCC ATC CTG AG/3InvdT (SEQ ID NO: 11) | 66.5, 46.0 | 1.21 | 35 | 30002, 31102, 32202 31202, 32102 |
| RNU6B | 5Acryd/GAT ATA TTT TAA AAA ATA TGG AAC GCT TCA CGA ATT TGC GTG TCA TCC TTG CG/3InvdT (SEQ ID NO: 12) | 64.4, 58.4, 56.9, 56.1 | 0.95 | 55 | 30000, 31100, 32200 31200, 32100 |

Code, buffer, and probe prepolymer solutions were loaded into four-inlet microfluidic synthesis channels using modified pipette tips (Biosciences) as delivery chambers and forcing pressures of 4.5 psi. Hydrogel microparticles (250×70×35 μm) were simultaneously synthesized, encoded, and functionalized at rates up to 16,000 per hour with 100-ms UV exposures (Lumen 200 at 75% setting, Prior Scientific) controlled with a shutter system (Uniblitz, Vincent Associates) interfaced with a custom-written Python automation script. Stream widths were adjusted such that code and probe regions spanned 140 and 40 μm, respectively, of the length of the particles. Buffer regions accounted for the remaining 70 μm of the length. We also showed that the same particle dimensions can easily accommodate two probe strips, with no loss in performance upon incubation, labeling, and scanning.

Following polymerization, particles were flushed down the synthesis channel and collected in a 1.7-ml Eppendorf tube containing 950 µl of TET (1×TE with 0.05% (v/v) Tween-20 surfactant (Sigma Aldrich)). Tween was added to prevent particle aggregation. Particles were next suspended in 200 µl of PEG 200 for 5 min and then rinsed with 700 µl of TET. This washing sequence was used to rinse the particles of unreacted PEG-DA, probe, and rhodamine. The wash sequence was repeated two more times and involved manual aspiration of supernatant facilitated by centrifugal separation of the dense particles. Particles were stored in TET at final concentrations of ~12.5 particles/µl in a refrigerator (4° C.).

Example 2 miRNA Incubation Experiments

This Example demonstrates typical sample incubation steps suitable for use in the present invention.

For all exemplary incubations studied, particles synthesized, for example, by the methods described in Example 1, were brought to room temperature prior to use, and each incubation was carried out in a total volume of 50 µl in a 0.65-ml Eppendorf tube with a final salt concentration of 350 mM NaCl and all twelve types of particle present (~360 particles/incubation tube). For calibration and specificity studies, a hybridization buffer (TET with assay-specific NaCl molarity) was first added to the Eppendorf tube, followed by all relevant target sequences (IDT) diluted in a mixture of 1×TE with 500 mM NaCl. Tween was excluded from the dilution buffer to prevent inaccuracies in pipetting steps that can arise from surfactant-induced changes in wettability. Depending on the assay type, either 1 µl of TET or 1 µl of *E. coli* total RNA (200 ng/µl) was introduced. For tissue profiling studies, hybridization buffer was added directly to a tube containing either 2.5 or 1.0 µl of previously frozen extracted total RNA (one individual per tissue type; stored at 100 ng/µl). Primary pair samples consisted of total RNA isolated from primary tumor and its adjacent normal tissue. Total RNA for all tissues was isolated by TRIzol purification; integrity of isolation was confirmed by checking for intact 18S and 28S ribosomal RNA. Lung sample (BioChain) was obtained from 50-year-old male with poorly differentiated squamous cell carcinoma. Breast sample (BioChain) was obtained from 53-year-old female with moderately differentiated invasive lobular carcinoma. Stomach sample (BioChain) was obtained from 70-year-old female with poorly differentiated adenocarcinoma. Pancreas sample (BioServe) was obtained from 65-year-old female with well-differentiated acina cell carcinoma. For all exemplary assays, 1 µl of miSpike (IDT) appropriately diluted in 1×TE with 500 mM NaCl was also introduced to give a total amount of 100 amol of the synthetic sequence to measure consistency of scanning/labeling and for quantification purposes. Prior to the addition of particles, incubation mixtures were heated to 95° C. for 5 min in a Multi-therm shaker (Biomega) and then brought back to room temperature over a 7 min period. A previously prepared master mix of particles (18 per µl) was thoroughly vortexed for 1 min, and 20 µl (~30 particles of each probe type) was introduced to each incubation tube. Incubation with target was carried out at 55° C. for 90 min in a thermomixer (Quantifoil Rio) with a mixing speed of 1800 rpm.

Following hybridization with target, samples were rinsed three times with a solution of 500 µl TET containing 50 mM NaCl. Supernatant was manually aspirated from the tube following centrifugal separation of the particles. All but 50 µl of solution was aspirated after the third rinse. Next, 245 µl of a previously prepared ligation master mix (100 µl 10× NEB-uffer 2, 875 µl TET, 25 µl of XXXATPcarrier, 250 pmol of ATP, 40 pmol of universal adapter, and 800 U of T4 DNA ligase) was added to the tube. The mixture was placed in the Multi-therm shaker at 21.5° C. for 30 min with a mixing speed of 1500 rpm. Following ligation, an identical three-rinse cycle was performed. Streptavidin-r-phycoerythrin reporter (SA-PE, 1 mg/ml) was diluted 1:50 in TET and added to obtain a final dilution of 1:500. Samples were incubated in the Multi-therm unit at 21.5° C. for 45 min. After another three-rinse cycle, particles were additionally rinsed in 500 µl of PTET (5×TE with 25% (v/v) PEG 400 and 0.05% Tween-20), and then suspended in a final volume of 50 µl PTET for scanning Prior to use, all PTET was sonicated for 5 min to eliminate aggregations of polymer.

Example 3

Detection Using Multifunctional Particles

In this Example, hydrogel particles were use. The synthesis of chemically geometrically complex hydrogel microparticles can be carried out using the flow lithography technique explained in detail in U.S. Pat. No. 7,709,544.

Figure 8A:
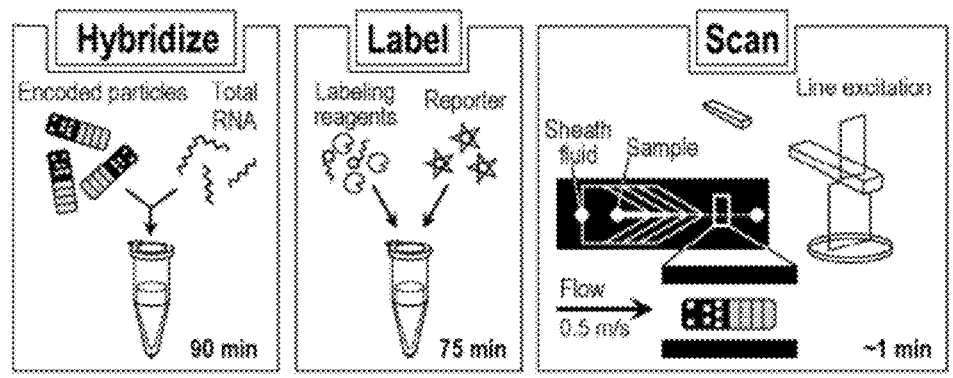
FIG. 8 shows an exemplary encoded gel particle assay system. (a) workflow of platform includes (i) hybridization of particles with target, (ii) incubation of particles with universal labeling adapter, ligation enzyme, and fluorescent reporter, and (iii) scanning of particles to determine code identity and amount of target bound. A typical particle includes a fluorescent barcoded region and a probe-laden region flanked by two inert sections. The central-most hole has a fixed value to indicate particle orientation. (b) Actual PMT fluorescence signatures of 75 flow-aligned particles from a 3-s scan segments. (c) Magnified signatures of individual particles from (b). Overlaid scans were acquired on different days and demonstrate reproducibility of analysis procedure. Scale bar below image is 50 μm.

By polymerizing across laminar co-flowing streams of monomer, multifunctional particles with distinct chemical regions can be rapidly (>$10^4$/hr) produced with high degrees of reproducibility. Separate "code" and "probe" regions are used to identify particles and capture targets, respectively. The bulk-immobilization of probe molecules in the bio-inert, PEG-based gel scaffolds provides solution-like capture kinetics and high degrees of both specificity and sensitivity, leading to significant advantages over surface-based immobilization strategies employed in microarrays and existing particle systems. Patterns of unpolymerized holes in the code portion of the particle serve as the basis for a graphical multiplexing barcode to identify the probe(s) in a particular particle. Unlike bead-based systems that use optical encoding of spheres, an arrangement in which particles have multiple distinct regions makes single-color scanning possible, with only one excitation source and one detector required (FIG. 8a). Furthermore, the coding library can easily be expanded to accommodate high levels of multiplexing or parallel processing of samples. Other methods for encoding these particles can also be implemented as discussed above; for instance, the particles can bear stripes with variable fluorescent intensities (of one or multiple wavelengths), optical properties, dimensions, etc.

In addition to bearing a code, particles also bear a probe region where targets are captured for quantification. The probes typically consist of species of biomolecules that bind specifically to a target of interest. For nucleic acid detection, probes typically consist of DNA oligonucleoties. A suitable DNA probe design and labeling methodology can be employed for a post-hybridization labeling method that accommodates operation of a gel particle scanning system for high-throughput multiplexed miRNA quantification. In the discussion below, particle synthesis, incubation, and scanning steps are described in detail for miRNA quantification, but this is provided as one example only, and it is to be recognized that such techniques are applicable to nucleic acids in general and are herein contemplated.

Figure 8B:
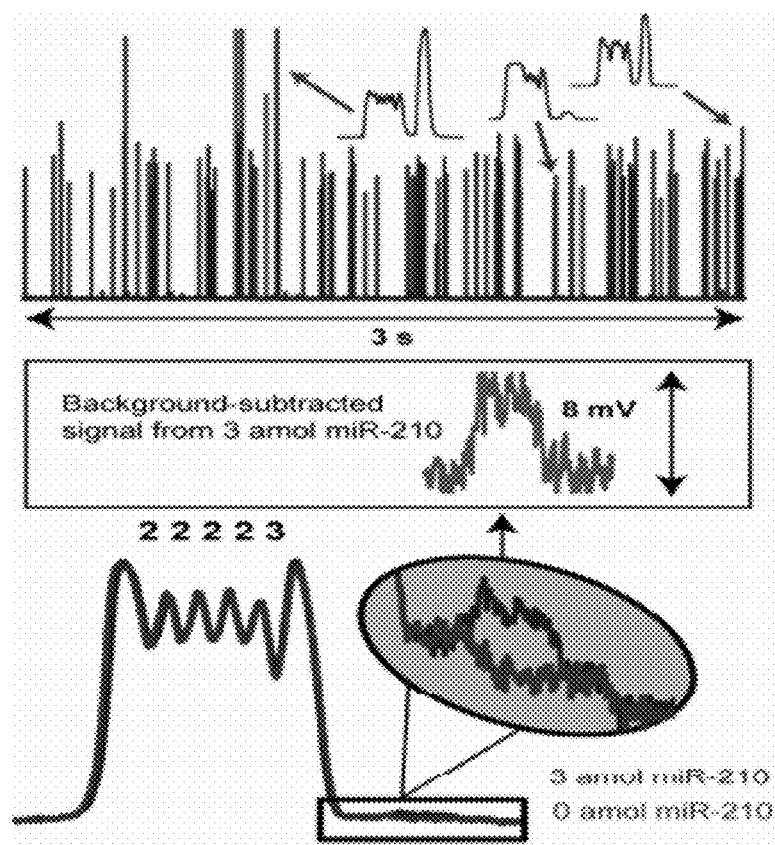

It is possible to use encoded particles with a post-hybridization labeling scheme and a suitable scanner, e.g., a slit-scan system, to perform rapid, multiplexed analysis of nucleic acids (FIGS. 8b and c).

Figure 8C:
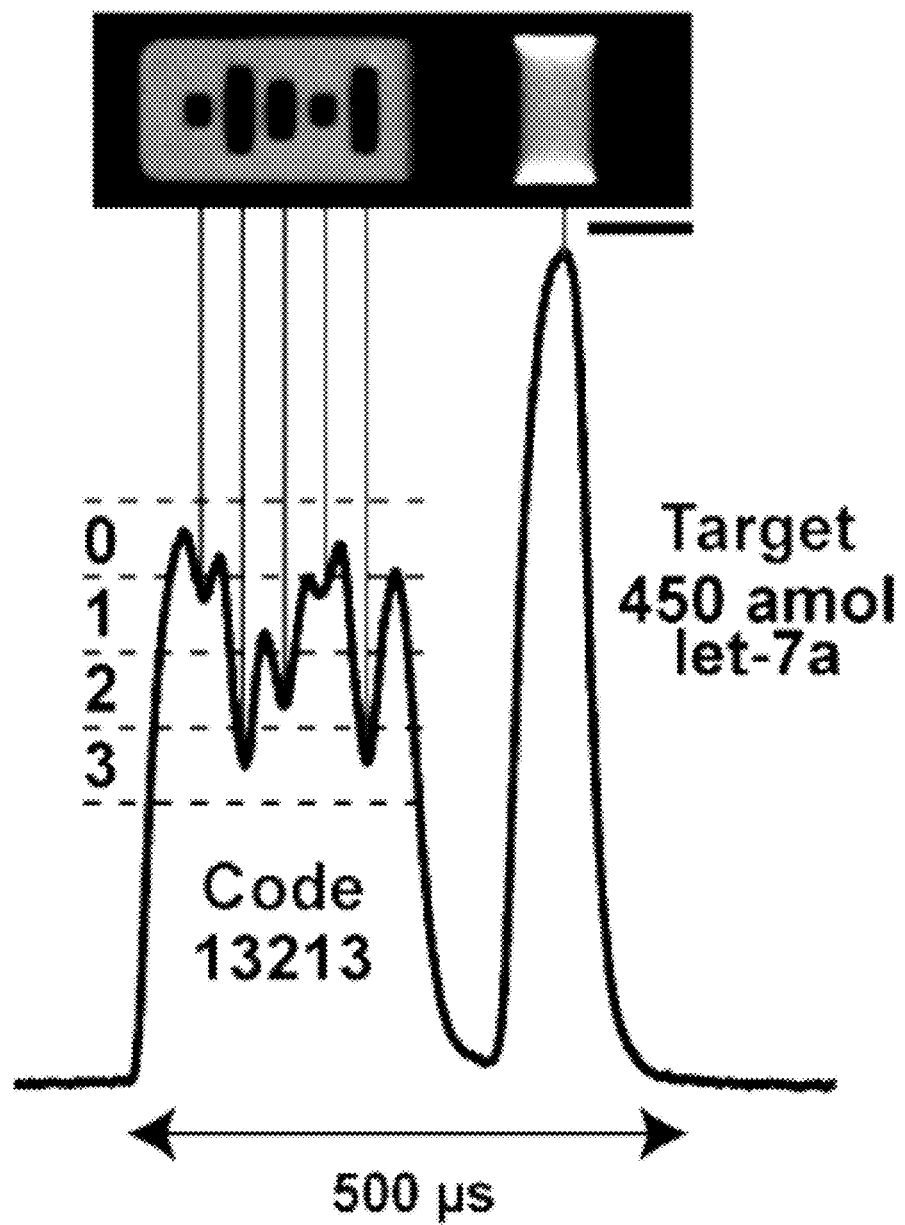
Figure 9A:
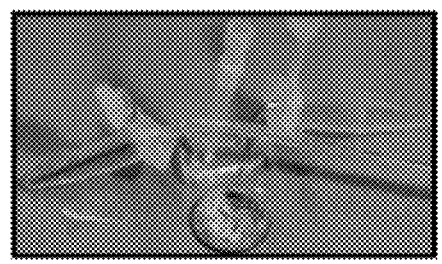
FIG. 9 illustrates an exemplary high-throughput flow alignment device and code design. (a) Image of PDMS focusing chamber attached to glass slide, with inlets and outlet attached. Reservoir inlet on the left delivers sheath fluid, while central pipette tip delivers the particle-bearing fluid. Reservoir outlet on the right serves as a collection point for particles that have been scanned. The chamber is mounted on a standard inverted fluorescence microscope for scanning runs. (b) Images of particles used to optimize scanner performance. Simple plug particles were scanned to maximize signal-to-noise ratio (SNR) and frequency response of detection circuit. Particles with holes of various areas were used to determine the minimum differences in size required to distinguish between coding levels. Scale bars are 50 μm. (c) In the final particle design, coding holes were separated by 8 μm, and the lengths of the holes were 15, 27.5, and 40 μm for levels 1, 2, and 3, respectively. All holes had a width of 12 μm.

In some embodiments, particles are designed to be scanned rapidly in a flow-through system such that the fluorescent signal obtained along each particle is integrated across the particle width by the detector. The particles each have a fluorescent code-region, bearing a series of holes that are used to identify the particle, negative control regions, and at least one probe region where targets are captured and labeled. The sizes of the holes in the code region determine the depths of the fluorescence troughs in the signature and thus indicate the particle identity. We optimized the particle architecture and hole design (FIG. 9) to find that four distinguishable coding levels (0-3) could be obtained for 70-μm wide particles, leading to 192 possible codes for a five-bar particle (FIG. 8c). Multiplexing capacity could easily be augmented to >$10^5$ by adding more bars, using multiple fluorescent levels for the code region, or incorporating multiple probes on each particle. We developed and trained a decoding algorithm written in MATLAB to accurately decode particles and quantify targets. Any suitable decoding technique can be employed. In the example algorithm, particle orientation (code- or probe-first) and velocity are determined to analyze the coding holes and establish a first estimate of code identity. A revised assignment is calculated by checking the consistency among holes identified as the same level, and a decoding confidence score is then computed and used to accept or reject particles. This method typically provides a decoding accuracy of ~98%, with only ~10% score-based rejection at throughputs up to 20 particles/s.

Example 4

Post-Hybridization Labeling

To generate a detectable signal indicating the presence and capture of nucleic acid targets, an exemplary post-hybridization ligation-based methodology is provided and demonstrated in this Example and Example 5 for labeling.

Such a post-hybridization method can be used to fluorescently label bound selected targets, e.g., miRNA targets. Existing approaches rely on the bulk-labeling of RNA using chemical or enzymatic means. These methods may suffer from high cost, the need for small-RNA purification and clean-up, sequence bias due to secondary structure, or complicated, time-consuming protocols. Here, we provide, for example, a two-step method to efficiently label targets after hybridization in about one hour.

Experimentally, we used T4 DNA ligase to link a universal oligonucleotide adapter to the 3' end of targets captured on gel-embedded DNA probes that act as a ligation templates (FIG. 10). As such, we can use a common, universal adapter to label multiple targets in a single reaction. The labeling process requires only a few simple steps. First, particles are hybridized with the sample, in this case total RNA, to capture appropriate targets in the particle probe regions. After excess sample is rinsed away, a ligation mix is added that includes the appropriate enzymes, all important co-factors (such as ATP), and a common biotinylated adapter. After a short reaction (typically 5-60 min) at room temperature, a low-salt buffer is used to rinse away any unreacted adapter. After rinsing away unreacted adapter, the particles are incubated with phycoerythrin-conjugated streptavidin reporter (SA-PE) to provide fluorescence. After another rinse, the particles can then be analyzed. More importantly, this labeling method was very efficient, had no minimal input RNA requirement, and showed no sequence bias for the targets used in this exemplary study (Examples 4 and 5). For each new miRNA target species, we incorporated a target-specific sequence into the universal probe template; complex modification and customization were not necessary.

In this arrangement, the adapter sequence was designed to minimize probe hairpin formation, which could retard target hybridization, and provide an adapter-probe melting temperature $T_m$ that was ~10-20° C. in ligation buffer. Although we used a reduced salt buffer during the rinse, the dehybridization of unreacted adapter can be accomplished using any condition that destabilizes nucleic acid interactions (low salt, high temperature, additives such as DMSO, PEG, or glycerol, etc.). Typically, we use SA-PE reporter to achieve maximum fluorescent signal. In addition or alternatively, a ligation-based labeling can be performed with adapters that are directly labeled with fluorophores or other reporting entities. Without being bound to any particular theory, it would be appreciated that this reduces the time and complexity of the assay. The process can be used, with appropriate probe and adapter design, to ligate adapters to the 3' end of DNA or RNA species containing a 3' OH, or at the 5' end of these species containing a 5' phosphorylation.

Example 5

Optimization and Variations of Ligation-based Labeling

In various embodiments, several aspects of the labeling technique described in the present invention were optimized, including probe/adapter design, reagent concentrations, rinse buffer salt content, ligation time, and ligation temperature. We show here the effects of ligation time and adapter tail length on labeling efficiency. The nucleic acid probes, targets, and adapters (all received from Integrated DNA Technologies, IDT) are given in the table below.

TABLE 2

Nucleic acid probes and targets used in optimization studies. Sequence in bold represents universal adapter-specific sequences, sequence in regular represents target-specific sequences, and sequence underlined represents poly(A) tails.

| Oligo Name: | Sequence/Modifications: |
|---|---|
| let-7a probe, DNA | /5Acryd/GATATATTTTAAACTATACAACCTACTACCTCA/3InvdT/ (SEQ ID NO: 13) |
| let-7a target, RNA | 5'-UGAGGUAGUAGGUUGUAUAGUU-3' (SEQ ID NO: 14) |

TABLE 2-continued

Nucleic acid probes and targets used in optimization studies. Sequence in bold represents universal adapter-specific sequences, sequence in regular represents target-specific sequences, and sequence underlined represents poly(A) tails.

| Oligo Name: | Sequence/Modifications: |
|---|---|
| UA10-Cy3, DNA | /5Phos/TAAAATATAT/3Cy3/ (SEQ ID NO: 15) |
| UA10-bio, DNA | /5Phos/TAAAATATAT/3Bio/ [poly(A) = 0] (SEQ ID NO: 16) |
| | /5Phos/TAAAATATAT<u>AAA</u>/3Bio/ [poly(A) = 3] (SEQ ID NO: 17) |
| | /5Phos/TAAAATATAT<u>AAAAAA</u>/3Bio/ [poly(A) = 6] (SEQ ID NO: 18) |
| | /5Phos/TAAAATATAT<u>AAAAAAAAAAAA</u>/3Bio/ [poly(A) = 12] (SEQ ID NO: 19) |

Adapter/Probe Design

Exemplary probes described above were designed to include a miRNA-specific region and an adapter-specific region, such that when bound, the 3' end of the miRNA target would abut the 5' end of the adapter. We chose to label the 3' end of miRNA targets because it has been demonstrated that when using a DNA template, the action of T4 DNA ligase in joining DNA to RNA molecules proceeds several orders of magnitude more rapidly at the 3' end of RNA versus the 5' end (Bullard, D. R. et al., *Biochem J* 398, 135-144 (2006)). The adapter sequence and length were chosen such that (1) the melting temperature was between 10-20 C in ligation buffer, (2) the sequence was not significantly self-complementary in order to avoid adapter hairpin or homodimer formation, and (3) complete DNA probes (with adapter and miRNA sequences) did not show appreciable hairpins for the miRNAs investigated.

Ligation Time

Figure 11:
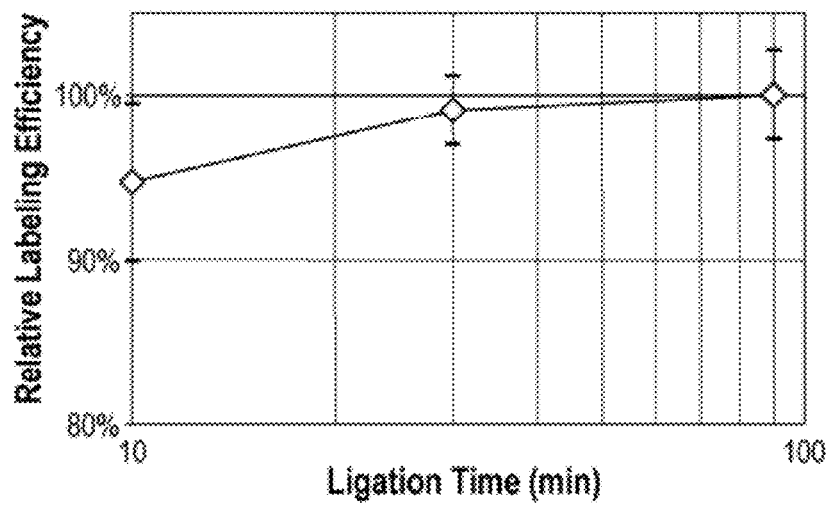
FIG. 11 illustrates an exemplary result showing relative ligation efficiency over time. Error bars represent the standard deviation taken over measurements from five particles.

We performed studies to determine the minimum ligation time needed for our labeling assay, using let-7a as a model system. Particles bearing a let-7a DNA probe region were incubated with 5 fmol synthetic let-7a RNA at 55 C for 110 min. Particles were rinsed three times with phosphate buffered saline containing 0.05% Tween-20 (PBST, pH 7.4, Fluka) and incubated with 250 l of a ligation mix containing 200 U T4 DNA ligase, 40 nM Cy3-modified adapter (UA10-Cy3), and 0.05% Tween-20 in T4 DNA ligation buffer (NEB) for 10, 30, or 90 min at 16 C. After ligation, particles were rinsed three times in TE containing 0.025 M NaCl, deposited on a glass slide, and imaged using a CMOS camera (Imaging Source). We measured the fluorescence intensity in the probe region of each particle, subtracting the background fluorescence to get a target signal, which indicated ligation efficiency. The results are shown in FIG. 11.

We calculated the relative efficiency by normalizing each signal by that obtained for the 90 min sample. As can be seen in FIG. 11, ligation is >95% complete even after a short 10-min reaction. For the experiments described in this work, we chose to use a ligation time of 30 min to ensure nearly complete ligation.

Tail Length for Biotinylated Adapters

The reporter streptavidin-phycoerythrin (SA-PE) is a large protein structure that has a radius of gyration on the order of ~10-15 nm. As such, when using biotinylated adapters with the SA-PE reporter, we found that it was beneficial to extend the biotin group away from the polymer backbone of the gel matrix. To do this, we used a poly(A) tail at the 3' end of the adapter and investigated the effect of tail length on target signal.

In this experiment, we used the same let-7a particles as in the previous section. We incubated with 50 amol let-7a miRNA for 60 min at 50 C. The particles were rinsed three times in PBST, and divided into four separate tubes. Particles in each tube were incubated for 30 min at room temperature with ligation mix containing 200 U T4 DNA ligase, and 40 nM UA10-bio (with either a 0, 3, 6, or 12 bp poly(A) tail), in 1× T4 DNA ligation buffer (NEB) with 0.05% Tween-20. After ligation, particles were rinsed three times in TE containing 0.05 M NaCl and 0.05% Tween-20. Particles were deposited on a glass slide and imaged using an EB-CCD camera. The target signals were compared to determine the effect of poly(A) tail length, as shown in FIG. 12.

Figure 12:
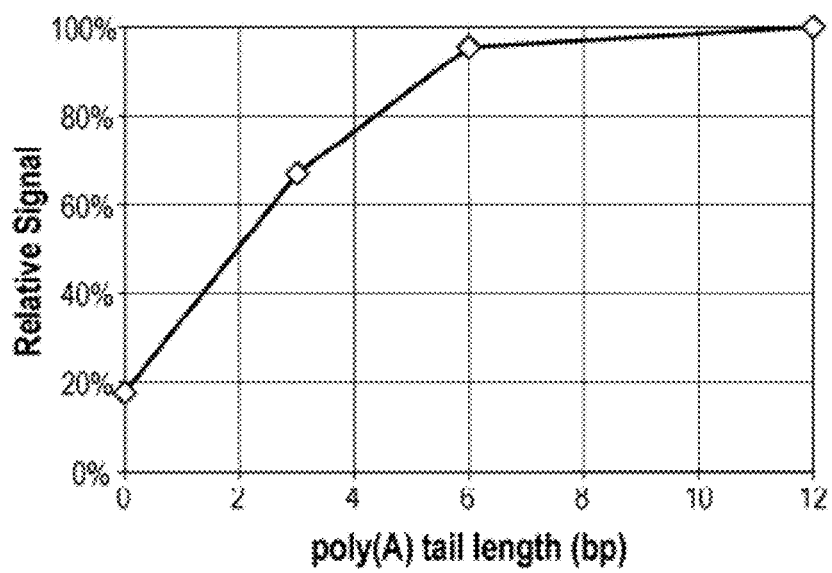
FIG. 12 illustrates an exemplary result showing effect of universal adapter poly(A) tail length on fluorescence signal when using biotinylated adapters with a streptavidin-phycoerythrin reporter. Signals are relative to that measured for a tail length of 12 bp.
Figure 13A:
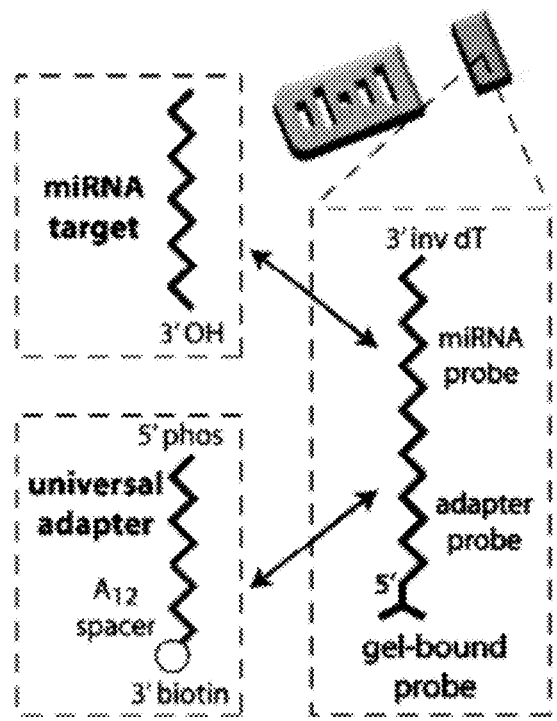
FIG. 13 illustrates an exemplary direct labeling with fluorophore-conjugated adapters, which are ligated to the end of captured targets. Non-ligated adapters can be rinsed away and the particles are imaged (or scanned in a flow through device). Fluorescence in the probe-region of the particles is indicative of the amount of target present.
Figure 13B:
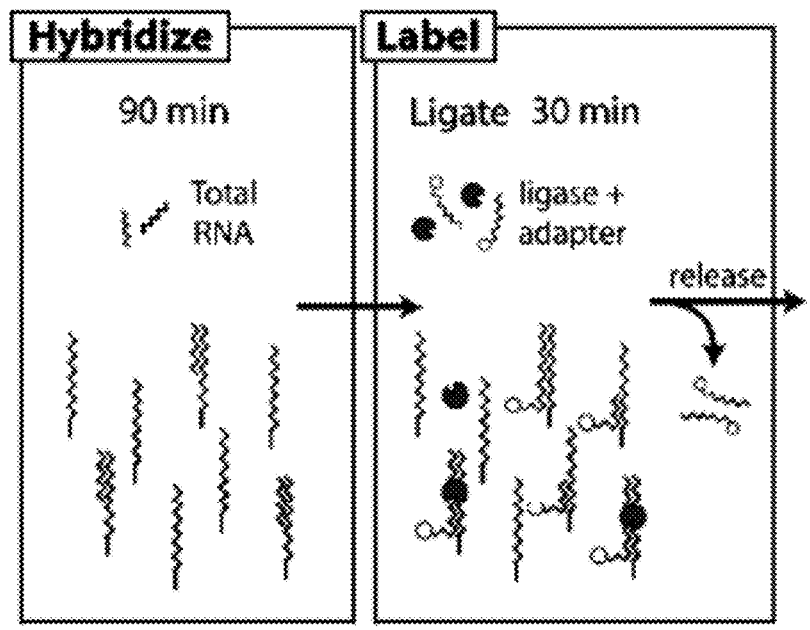
Figure 13C:
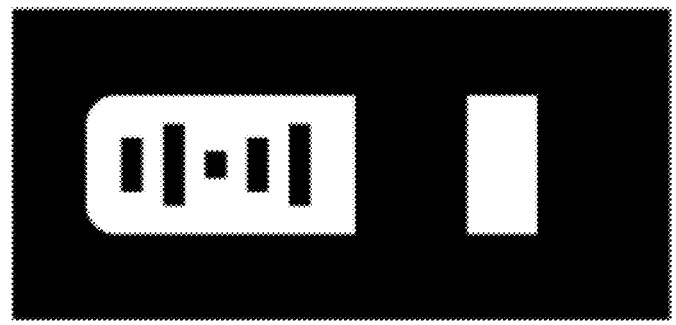

As can be seen in FIG. 12, the length of the poly(A) tail has a large effect on target signal obtained. From zero to 12 bp, the signal increases ~5× but seems to level off at that point. For the experiments described in some examples, we chose to use universal adapters with poly(A) tail lengths of 12 bp.

In various embodiments, a wide range of alternative techniques and systems to those described above can be successfully employed. Examples of such are provided here.

Direct Adapter-Based Labeling Using Fluorophore-Conjugated Adapters

Instead of using a technique in which biotinylated adapters are ligated and later reported with streptavidin-conjugated fluorophores, fluorophores can be used directly. When ligating to the 3' end of hybridized targets, the universal adapters will have desired a fluorophore incorporated, preferably at the 3' end or on one of the internal nucleotides. As illustrated in Example 13, this method eliminates one step in the process, making it more simple and rapid.

Multiplexed Detection Using Adapters with Different Fluorophores

Figure 14:
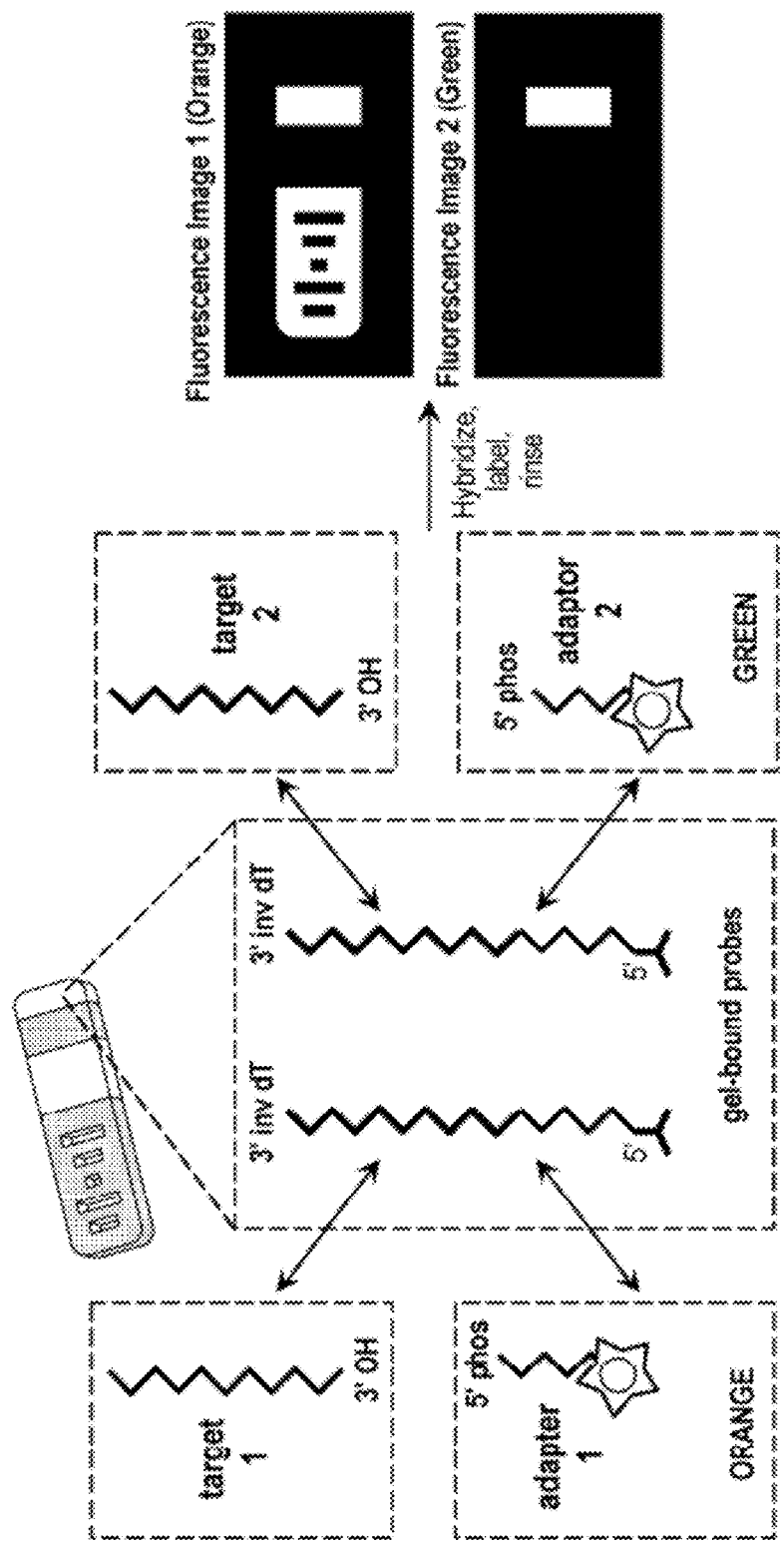
FIG. 14 illustrates an exemplary multiplexed detection using multiple adapters with different fluorescent colors. A given probe region of a particle may contain several unique probes, with common or differing adapters sequences. Adapters bearing fluorophores with unique emission spectra (fluorescent or other) can be ligated to indicate the capture of multiple targets within a given probe region. The amount of fluorescence from each fluorophore may be quantified independently to determine the amount of each target present.

For some applications, it can be important to detect multiple nucleic acid species in a common region. When the probes are not separated in distinct regions of a particle or substrate, it is possible to perform multiplexed detection using adapters modified with fluorophores that have unique emission spectra. For example, three probes that each have a unique adapter probe sequence can be used in one region with adapters modified with 3 unique fluorophores. An example of this is shown in FIG. 14.

Alternately, for some applications it can be important to detect variability at the end of a target (e.g., targets with nucleotides cropped from one end). In this case, a similar probe can be used, but multiple adapters (preferably with different fluorophores) are used that extended a different number of nucleotides into the target probe region. Ligation would only occur if the target/adapter ends perfectly abut, thus the target end sequence(s) can be determined by measuring the levels of each fluorophore used for the various adapters. Alternately, adapters bearing the same fluorophore may be used with two separate quantification steps run in parallel (with two samples) or series (same sample but two ligation steps).

In the case of both labeling and universal encoding, ligation can be achieved at the 5' or 3' end of the adapters, especially when all species involved are DNA. When using DNA Ligase, it is known that ligation is much more efficient at the 3' end of RNA targets (i.e., the 5' end of the DNA adapter). Adapters may be DNA, RNA, or any type of nucleic acid analog. The nucleotides in the adapters or probes may be modified as locked nucleic acids, or otherwise.

Use of Other Functional Adapters

Fluorophores were employed for encoding and labeling in the experiments described above, but it is understood that other types of functional species can also be used, including but not limited to: chromophores, radioactive species, magnetic materials, quantum dots, etc. It is also understood that universal encoding can be achieved using an adapter bearing an intermediary species (eg. biotin), and functionalization (eg. fluorescence) can be added in an additional step. Adapters can have fluorophores at the end of their structure or along their backbone (eg. fluorescent nucleotides). Another approach is to use intercalating DNA/RNA dyes (like PicoGreen, YOYO-1, etc) to introduce fluorescence in universal encoding or labeling. These may be used in conjunction with enzymes like exonuclease that will selectively degrade nucleic acid species that are not protected from digestion. In this scenario, adapters with longer sequences or more secondary structure will lead to brighter signals from the intercalating dyes. In a different scenario, adapters may also bear specific nucleic acid sequences (tags) that can be targeted in subsequent processing to add fluorescence (e.g., using fluorophore-conjugated complementary oligonucleotides).

Rinse-free Labeling

It is possible to use the ligation-based labeling technique for analysis of particles without rinsing. In one example, ligation is carried out at a lower temperature (e.g., below the melting temperature, Tm, of the adapter) than scanning/analysis (which can be done above the Tm of the adapter). The melting temperature of the adapter can be adjusted via sequence, salt concentration, locked nucleic acids, etc to denature from the probe template at temperatures below, near, or above the temperature used when analyzing particles. Ligation and scanning can be performed right at or slightly above the Tm of the adapter—this still allows ligation (likely with decreased efficiency) with minimal residual adapter bound to the probes during analysis.

Example 6

Particle Scanning

Typical scanning methods suitable for use in the present invention are described in this Example.

Focusing devices (35 μm in height) with two inlets, one outlet, four side streams, and a 125-μm wide detection region were mounted on a Zeiss Axio Observer microscope equipped with a Zeiss Plan Neofluar 20× objective (NA 0.50) (FIG. 9a) (Chapin, S. C., et al., *Lab Chip* 9, 3100-3109 (2009)). A chrome-coated soda-lime glass mask (Advance Reproductions) was fitted into an iris slider bar and inserted into the field stop of the microscope to limit the beam spot of a 100-mW, 532-nm laser (Dragon Lasers) to a thin excitation window of 4×90 μm in the scanning plane. Prior to each scanning session, laser alignment was calibrated with a power meter (Newport, Model 1815-C). Using images captured from a Clara Interline CCD camera (Andor Technology), the excitation window was oriented such that its long dimension was aligned perpendicular to the flow direction approximately 750 μm from the exit port of the device. A switching box on the side port of the microscope was used to alternate between the CCD and a photomultiplier tube (PMT, Hamamatsu H7422-40) used to record fluorescence signatures of passing particles.

PTET was injected from a reservoir input to serve as a focusing sheath stream. For each trial, particle-bearing fluid was aspirated into a modified pipette tip using a syringe connected to the tip via Tygon tubing. The tip was inserted into the appropriate PDMS inlet port and a pressure of 8 psi was used to drive the flow of both fluids. A typical scan of 50 μl of particle-bearing fluid lasted ~30 s and used less than 25 μl of sheath fluid. Particle throughputs ranged from 5-25 per second, depending on the number of particles used in the assay. Devices were able to be used more than 50 times without degradation. Following each scan, a rinse solution of 30 μl 1×TE was flowed through the particle inlet to flush out stranded particles and thereby reduce inter-run contamination. Additionally, the loading tip was rinsed in ethanol and water so that it could be reused. With manual loading from Eppendorf tubes, eight samples could be scanned and analyzed in 30 min, leading to a projected throughput of ~125 samples per 8-h workday. In future applications of this technology, automation of the particle-loading and rinsing processes using well-plates and a computerized liquid handling system will greatly augment efficiency (>500 samples/day).

Figure 9B:
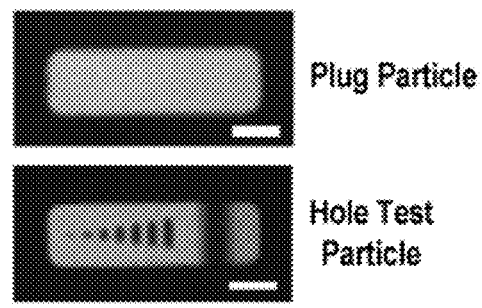
Figure 9C:
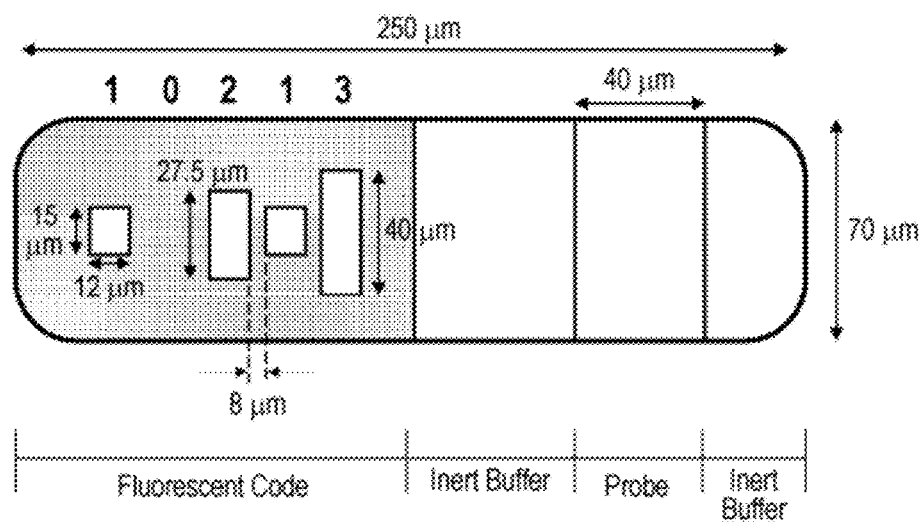
Figure 10A:
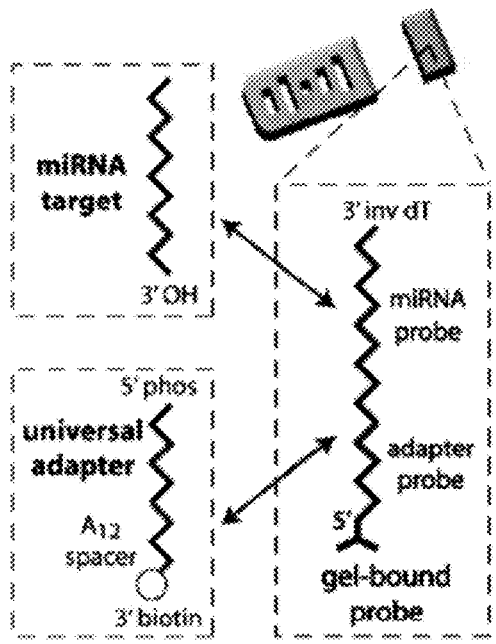
FIG. 10 illustrates exemplary post-hybridization miRNA labeling via ligation to a universal adapter. (a) DNA probes, lined at their 5' end throughout the probe region of encoded hydrogel particles, contain a miRNA specific sequence adjacent to a universal adapter sequence such that the 3' end of a captured target would abut the 5' end of a captured adapter oligonucleotide. The probe is capped with an inverted dT to mitigate incidental ligation and the adapter has a poly(a) spacer to extend its biotinylated 3' end away from the hydrogel backbone for efficient reporting. (b) After particles are hybridized with total RNA, T4 DNA streptavidin-phycoerythrin (SA-PE) is used as a fluorescent reporter. (c) the assay provides about atomole detection limits, defined at signal-to-noise=3. (d) single-nucleotide specificity is provided when synthetic let-7a RNA is spiked at 500 amol with particles bearing probes for let-7a, b, c, and d.
Figure 10B:
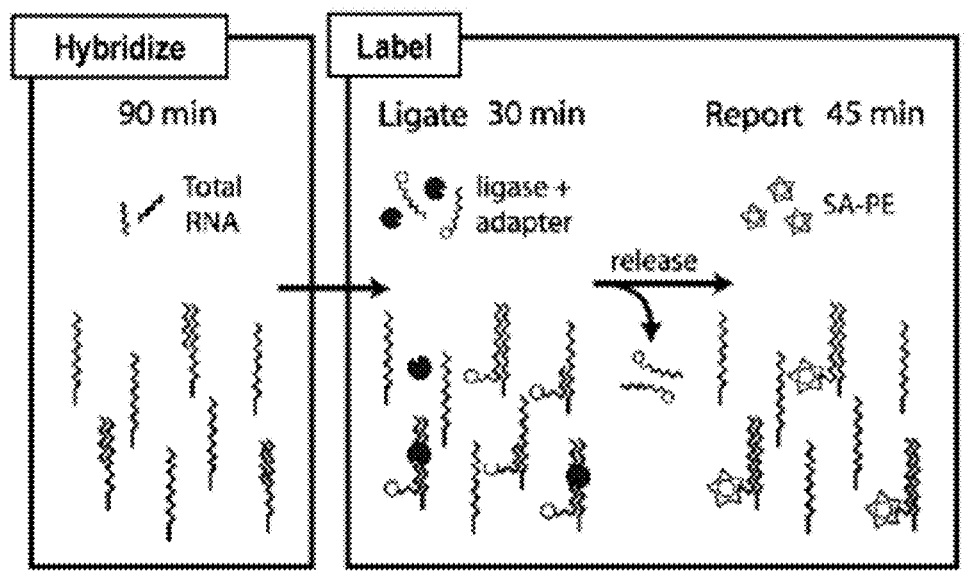
Figure 10C:
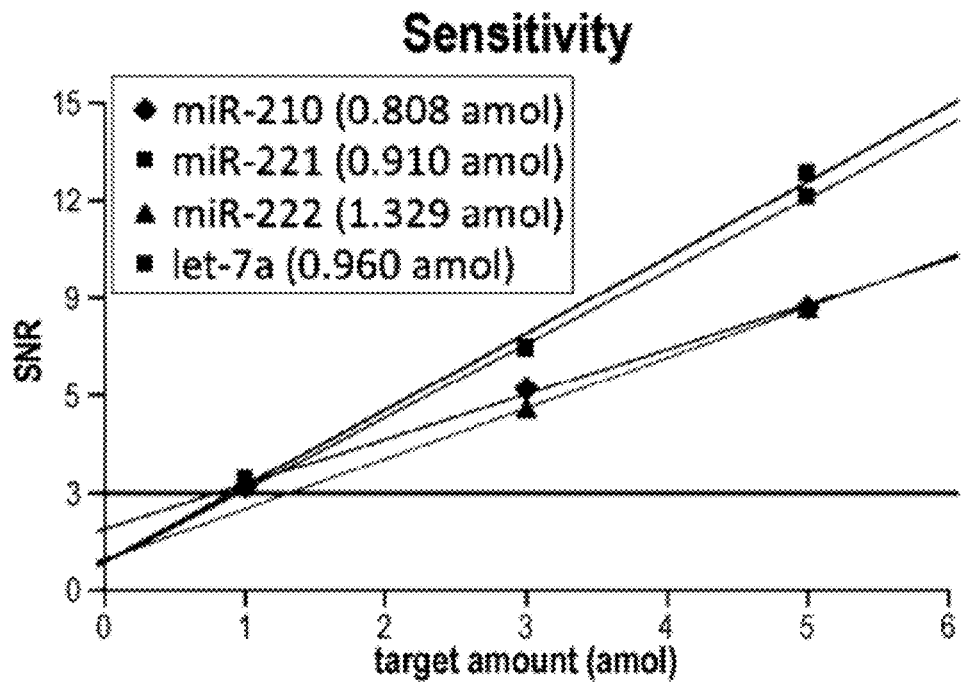
Figure 10D:
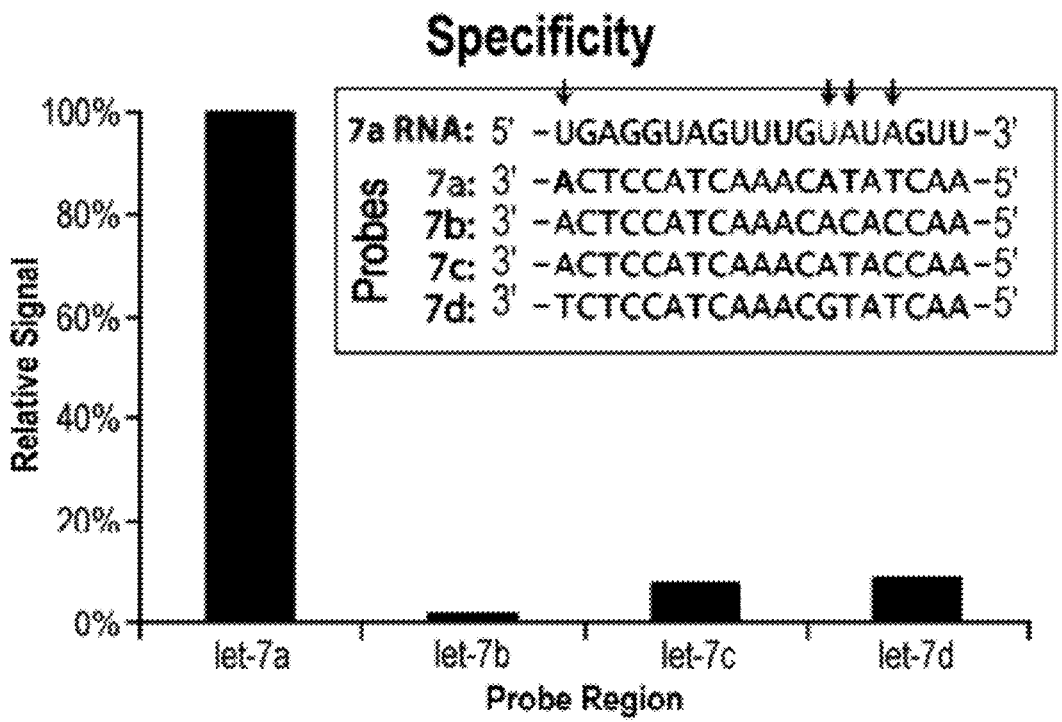

The output current of the PMT was conditioned using a homemade amplifier with a low-pass filter, and the resulting voltage signal was captured at a rate of 600 kHz by a digital acquisition (DAQ) board (USB-6251, National Instruments). A Python script was written to convert each scan to a binary text file for off-line analysis. Single-chemistry particles with fluorescent rhodamine incorporated throughout were scanned to optimize the performance of the scanning system, leading to a combination of amplifier gain (22), cutoff frequency (100 kHz), slit width (4 μm), and PMT control voltage (0.300 V) that produced the highest signal-to-noise ratio (SNR) and frequency response possible. Furthermore, by scanning particles with various barcode designs, it was observed that a minimum spacing of 8 μm was required between holes to prevent mechanical deformations of the soft hydrogels during flow alignment. The four-level code design was employed based on studies that systematically varied the size of the holes to determine effects on trough depth in scan profiles (FIGS. 9b and c).

Example 7

Data Analysis

Typical data analysis in accordance with the present invention are described in this Example.

Raw data files (20 million points/scan) produced by the scanning process were analyzed with a custom written MAT- LAB algorithm designed to isolate individual particle signatures, identify the code displayed by each particle, and quantify the amount of target bound. The algorithm processed scans of 50-μl samples in under 5 s, making the approach suitable for high-throughput applications. In the initial filter step, the algorithm excised portions of the scan that exceeded a threshold voltage and then interrogated each removed segment for characteristics that identified it as a particle signature. Using specific properties of the fluorescent code region as reference points, a high-confidence estimate of the velocity of each particle was determined and utilized to pinpoint trough locations for the five coding holes. The orientation of the particle (i.e., probe- or code-first) was established using the fixed-value "3" hole that bordered the inert buffer region. After an initial code identity was calculated from the trough depths, a secondary review was conducted by measuring the standard deviation in trough depths of holes designated to be of the same level and corrective action was taken if necessary. In the final decoding step, a confidence score was calculated for the particle by computing the linearity of the correlation between trough depth and assigned level. A particle decoding event was rejected if its Pearson coefficient fell below 0.97.

In order to calculate the amount of target bound, the measured particle velocity was used to infer the location of the center of the probe region. Briefly, a search window was used to investigate the scan in this region, seeking to identify a local maximum that could be correlated to a target-binding event. If a maximum was found, the position of the search window along the scan profile was adjusted until the two endpoints were sufficiently close in signal amplitude, thereby selecting a nearly symmetrical portion of the maximum over which to average for quantification purposes. In the cases in which a maximum was not found, the original estimate of probe center was used to calculate a mean signal without a search window. To calculate the background for a given probe sequence and incubation condition, particles from the same synthesis batch were incubated in the presence of only 100 amol of miSpike target according to the procedure described above. This method provided a measure of the probe-dependent background that arose from the PEG scaffold and the universal adapter used in the labeling process. Also, upon calculation of all code identities and target levels, a particle would be rejected from consideration if its target level was more than one inter-quartile range above the third quartile or below the first quartile of the data set consisting of target levels associated with the probe in question. This measure was taken as further protection against incorrect code assignments and inter-run contamination.

For calibration and profiling studies, mean background-subtracted signals were computed for each target at each incubation condition. For inter-run comparisons of calibration data, signals were normalized by background-subtracted miSpike amplitude, with the null (0 amol) samples providing the reference 100-amol miSpike value for both neat and *E. coli* investigations. miSpike target values displayed on the calibration curves (FIG. 15 and FIG. 16) were not adjusted to this reference in order to demonstrate the repeatability of the labeling and scanning process. For profiling studies, the background-subtracted miSpike signal from the first scan of each healthy tissue type was used as the reference for analysis of that tissue. Signals from a given profiling scan were further normalized by the RNU6B amount in that scan to facilitate direct quantitative comparisons that were independent of total RNA amount. Repeat runs of tissue assays were conducted at least one day after the original. For each calculated expression ratio, the healthy and tumor samples were assayed and scanned in the same set of experiments for consistency. We required at least 2 amol of target to be detectable in a tissue of a given disease state in order to calculate an expression ratio. As we only used a single patient sample for each tissue type, we implemented a threshold approach to determine dysregulation. For each target in each tissue, the three log-transformed expression ratios from the three separate trials were used to calculate an SNR, by dividing the mean of the set by the standard deviation. Targets with SNRs above 3 were considered to be dysregulated. It should be noted that all 20 instances of dysregulation were able to be correlated to observations from the literature regarding the expression profiles of either mature miRNA (16 of 20) or miRNA precursors (4 of 20).

Example 8 miRNA Profiling

The experiment described in this example demonstrates that compositions and methods provided in the present invention may be use for various applications (e.g., miRNA profiling).

Experimentally, this technique was proven by an investigation into the dynamic range, sensitivity, and specificity of the platform in the context of a 12-plex assay featuring ten clinically relevant miRNA targets. Because of its relative invariance across tissue types and disease states, RNU6B was used as an internal control for normalization purposes. We also used 100 amol of miSpike (a synthetic 21-mer) as an external control to validate the consistency of the labeling and scanning processes. We synthesized twelve batches of single-probe particles for this study. To compensate for discrepancies in target hybridization rates, we implemented a coarse rate-matching by tuning the probe concentration for each target using previously determined scaling laws (Table 1). To fully demonstrate the versatility of the scanner, five separate codes were correlated to particles of each probe type, thereby simulating a 60-plex assay.

Figure 15A:
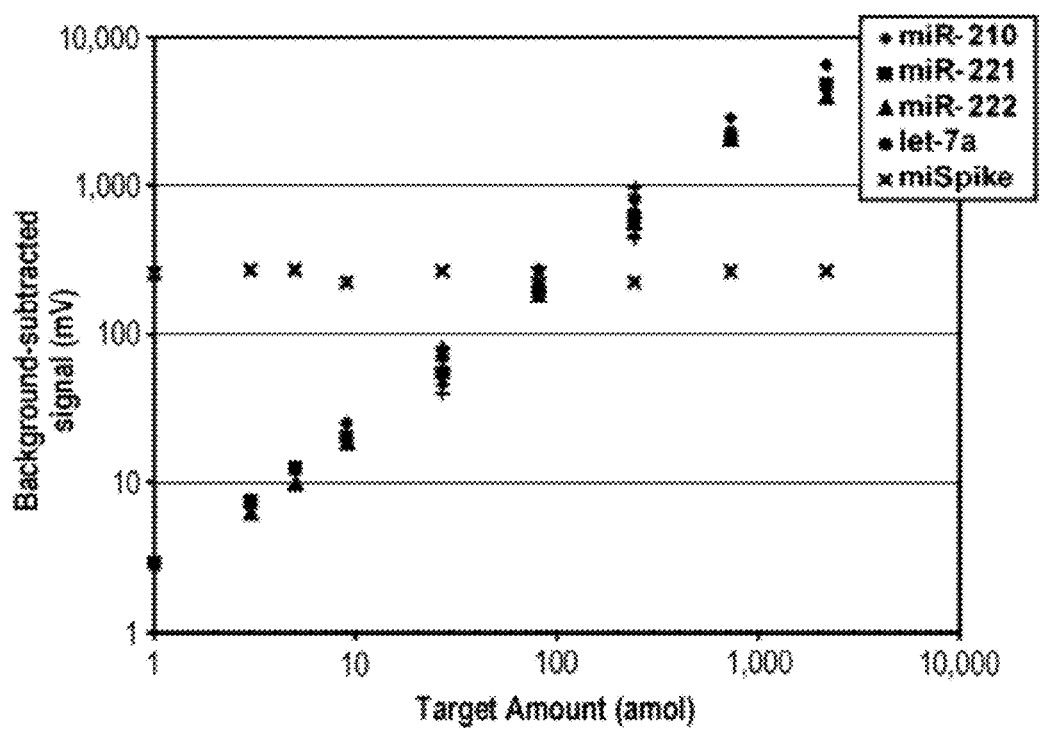
FIG. 15 illustrates an exemplary system performance in 12-plex assay. (a) Calibration curves for particle batches, with background-subtracted signal plotted against spiked target amount. miR-210, -221, -222 and let-7a were spiked into the same incubation mixes at the indicated amounts. the remaining seven naturally-occurring targets ('+' symbols) were spiked into the 27- and 243-amol trials to validate performance. For all trials, 200 ng of $E. coli$ total RNA was also spiked in for complexity. Mean COV of target level is 6.35% when considering target levels greater than 5 amol. Each point represents, on average, 19 particles from a single run. (b) Specificity of let-7a probe in the presence of sequences closely related to intended target (see inset box for target set). We observed a maximum cross-reactivity of only 27%. (c) Cancer profiling results for four types of human tissue. Error bars represent standard deviation in triplicate measurements on aliquots of the same single-patient sample. Amount of total RNA used in assays is 250 ng, unless otherwise noted.
Figure 15B:
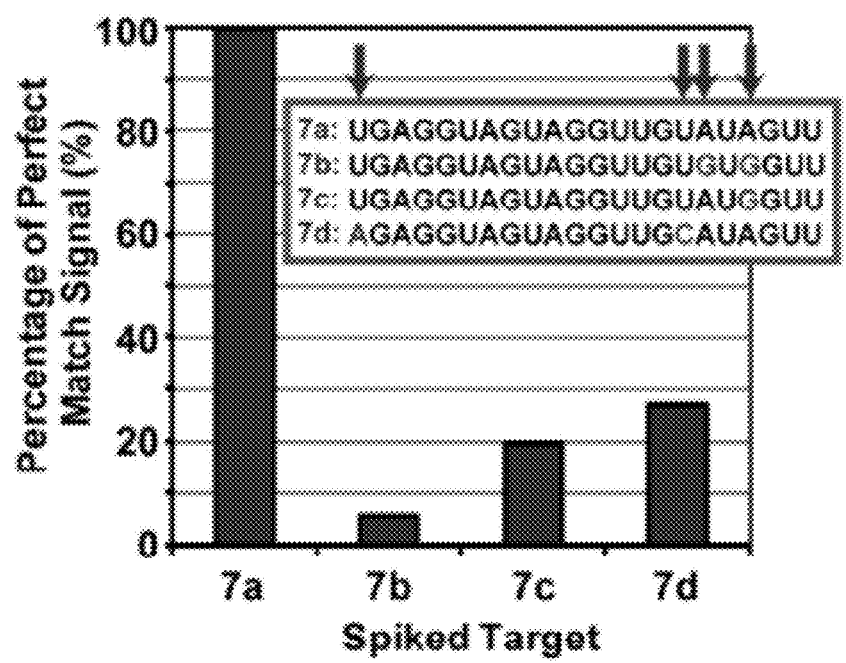
Figure 15C:
Figure 16A:
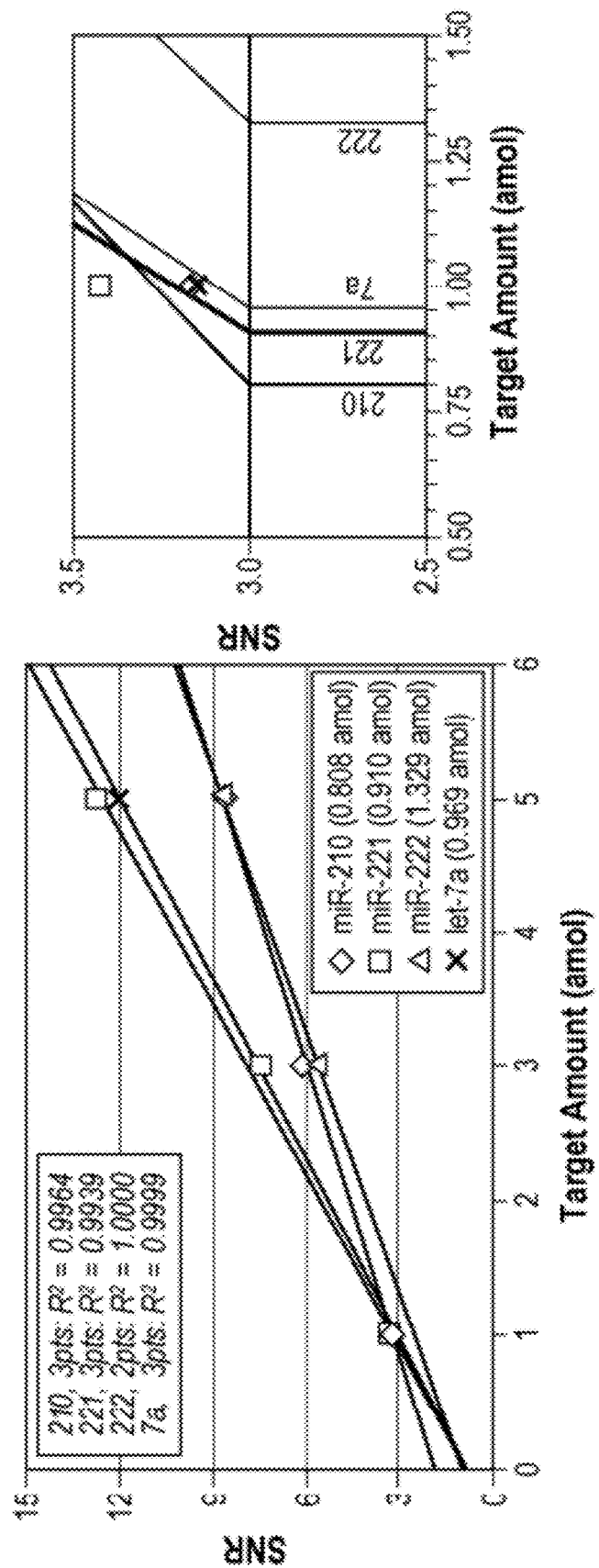
FIG. 16 illustrates exemplary results showing limit of detection calculations and calibration curves for neat samples. (a) Extrapolation of SNR for determination of limit of detection (LOD). The LODs of the four calibration targets (see legend) were calculated by finding the target amount at which the SNR was three. Regression lines with a mean Pearson coefficient of 0.9965 (excluding miR-222) were used to extrapolate LODs. (b) Calibration curves for particle batches incubated without spiked $E. coli$ total RNA. Except for the absence of $E. coli$ RNA, conditions are identical to those used to construct FIG. 3a. (c) Comparison of background-subtracted signals from neat and $E. coli$ calibration measurements. Clustering of points around the identity line (red) indicates highly specific detection with no noticeable decrease in binding rates in more complex samples. For all plots, all target levels (except miSpike) have been adjusted for comparison purposes by using the background-subtracted signal from the 100-amol miSpike profiles.
Figure 16B:
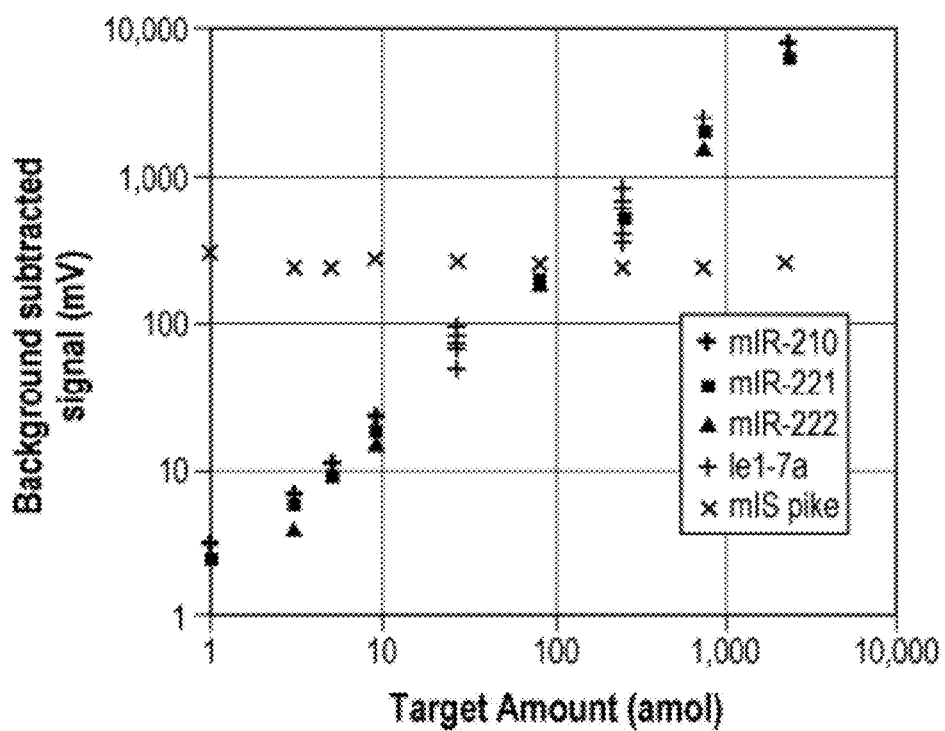
Figure 16C:
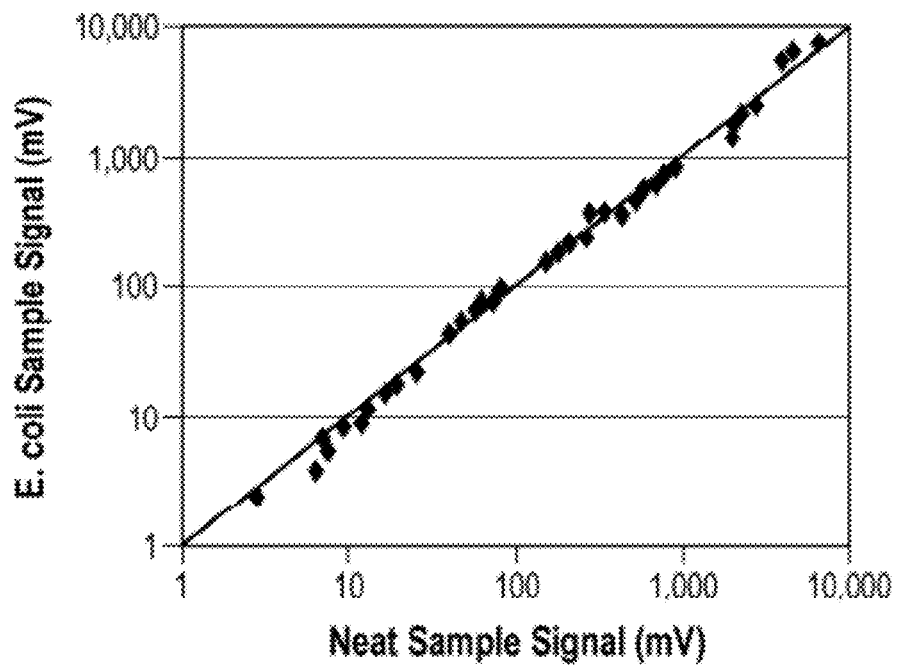
Figure 17:
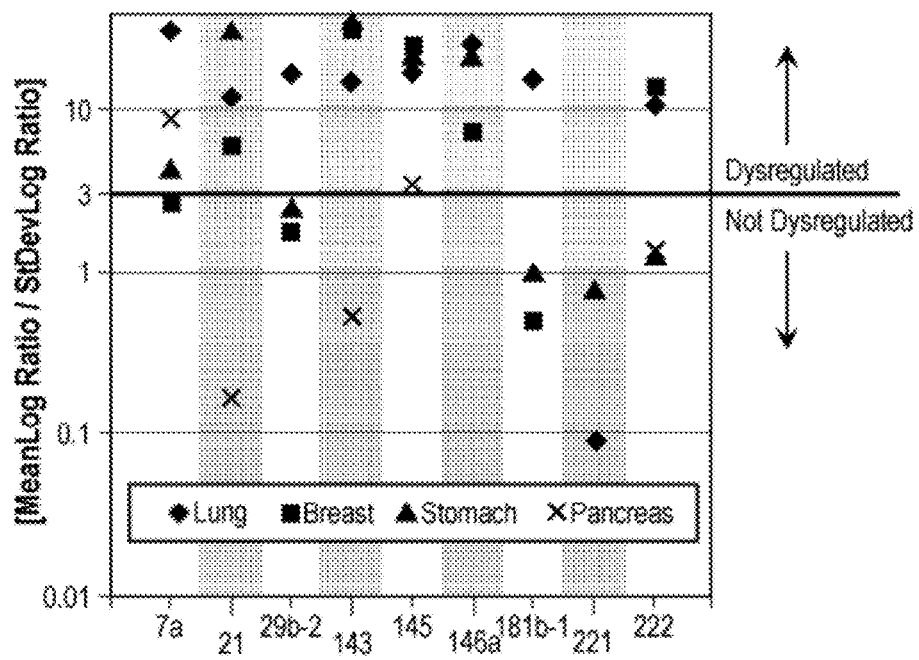
FIG. 17 illustrates an exemplary dysregulation classification. A SNR was used to distinguish dysregulated targets in tissue profiling. The mean and standard deviation of the log-transformed expression ratio were calculated for each target in each tissue for the triplicate assays. A SNR of three was chosen as the threshold for dysregulation. All 20 instances of dysregulation matched observations in the literature
Figure 18:
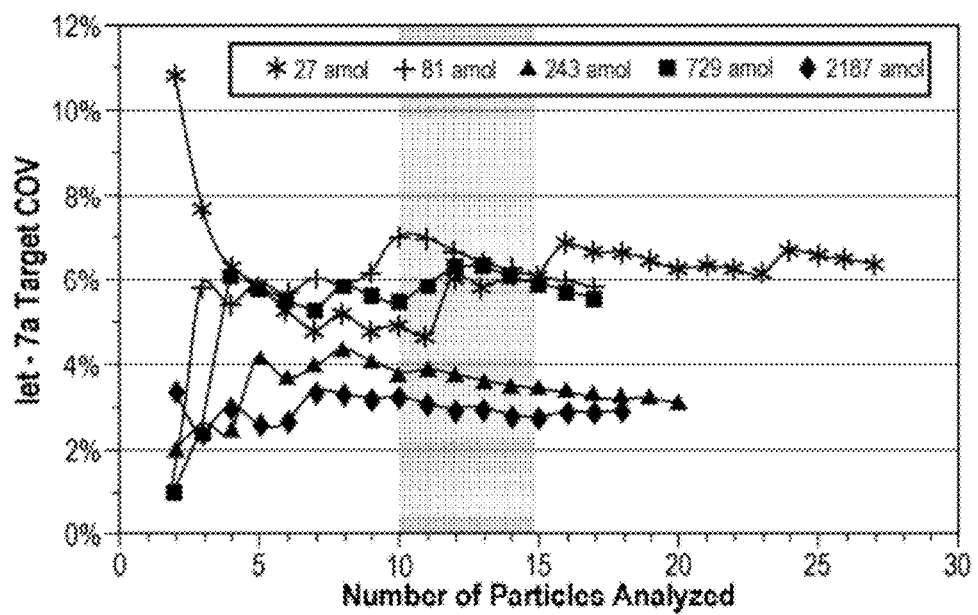
FIG. 18 illustrates exemplary results showing coefficient of variation (COV) of target level as a function of number of particles analyzed. The COV of the target level for let-7a in the $E. coli$ calibration scans was seen to stabilize to a nearly constant value in the 10-15 particle window for the five spike-in amounts presented above.

To further assess the sensitivity and dynamic range of our system, we simultaneously spiked four of the twelve targets into 50-μl incubation mixes at amounts ranging from 1 to 2187 amol. We observed a linear detector response over four logs, with sub-attomole sensitivity achieved for three of the four targets and strong agreement between neat samples and those spiked with 200 ng of *E. coli* total RNA to add complexity (FIG. 15 and FIG. 16). By comparison, existing bead-based approaches have a 200-amol limit of detection and only one log of range. To assess specificity, we performed assays with let-7a particles and four members of the let-7 family spiked separately at 200 amol into samples containing 200 ng *E. coli* total RNA. Scans revealed a maximum cross-reactivity of 27% (FIG. 15*b*), which is lower than other systems (microarray ~50%) and can be dramatically improved with lower hybridization salt concentrations (FIG. 17) These assays were very reproducible, with intra- and inter-run COV's of 2-7% (Table 3). Due to limitations in detection and particle preparation, it is common for users of current bead-based systems to employ 4,500 copies of each type of bead in an assay for high-confidence estimates of target level. By contrast, we found it sufficient to analyze only 10-15 hydrogel particles for each probe type (FIG. 18).

TABLE 3

Intra-run COVs in target level for *E. coli* calibration curve. All entries are percentages with each statistic calculated using 19 particles on average. miR-222 exhibited a limit of detection over 1 amol. Inter-run COV in background-subtracted miSpike signal (100 amol) for the nine represented scan sets was 6.84%.

| Target | 1 amol | 3 amol | 5 amol | 9 amol | 27 amol | 81 amol | 243 amol | 729 amol | 2187 amol |
|---|---|---|---|---|---|---|---|---|---|
| miR-210 | 59.45 | 29.22 | 10.88 | 10.93 | 1.81 | 5.91 | 1.39 | 5.85 | 1.93 |
| miR-221 | 36.71 | 9.95 | 21.80 | 18.41 | 4.11 | 7.20 | 2.79 | 6.81 | 2.01 |
| miR-222 | — | 5.96 | 16.10 | 15.62 | 4.85 | 5.25 | 3.26 | 5.93 | 3.27 |
| let-7a | 87.99 | 19.18 | 26.77 | 18.83 | 5.20 | 5.83 | 3.13 | 5.53 | 2.93 |

As a further validation of the platform, we performed expression profiling across tumor and adjacent normal tissue for several cancer types. As anticipated, we observed the dysregulation of several miRNA targets in all of the diseases investigated (FIG. 15c, Table 4, and Table 5). Although we used 250 ng of total RNA for these samples, similar results were obtained for lung samples using only 100 ng, suggesting that less input RNA would be sufficient. With a total assay time of only 3 h, the profiling is more efficient than microarray approaches (~24 h) and exhibits sensitivity and reproducibility far superior to that of existing bead-based methods.

TABLE 4

Mean target amounts and inter-run COVs in target amount for 250-ng tissue profiling replicates. Top number in each entry is mean amount for replicate trials (amol); bottom number in parentheses is the inter-run COV (%). Amounts were determined by comparison to the background-subtracted 100-amol miSpike signal from each run. Replicate assays were conducted on different days to rigorously test reproducibility. Each statistic was calculated using 16 particles on average. Entry spots lacking data indicate that target was not present above the 2 amol cutoff.

| | let-7a | miR-21 | miR-29b-2 | miR-181b-1 | miR-143 | miR-145 | miR-146a | miR-210 | miR-221 | miR-222 | RNU6B |
|---|---|---|---|---|---|---|---|---|---|---|---|
| Lung Tumor | 594.81 (3.18) | 1498.85 (10.57) | 68.36 (10.52) | 7.02 (21.45) | 85.61 (10.55) | 162.88 (6.05) | 77.02 (8.28) | — | 7.21 (8.09) | 8.13 (8.22) | 57.16 (7.46) |
| Lung Healthy | 368.08 (13.97) | 141.70 (12.10) | 31.80 (8.43) | 2.69 (18.61) | 59.79 (10.54) | 189.07 (8.98) | 6.95 (12.61) | — | — | 6.45 (12.33) | 10.84 (10.65) |
| Breast Tumor | 1094.19 (6.82) | 808.08 (9.96) | 65.88 (9.99) | 3.71 (5.01) | 32.48 (7.48) | 73.53 (11.20) | 9.26 (4.75) | — | — | 2.29 (16.14) | 116.88 (0.19) |
| Breast Healthy | 912.95 (6.30) | 302.39 (5.81) | 32.87 (25.08) | 2.65 (6.96) | 59.01 (8.52) | 149.06 (9.57) | 12.90 (5.89) | — | — | 10.20 (2.59) | 78.55 (3.05) |
| Stomach Tumor | 270.64 (8.96) | 561.87 (13.76) | 68.78 (19.21) | 2.28 (11.03) | 169.45 (3.99) | 388.39 (9.16) | 29.66 (2.89) | — | 2.93 (22.98) | 14.15 (8.16) | 175.69 (8.52) |
| Stomach Healthy | 258.28 (4.62) | 204.24 (24.90) | 73.44 (1.78) | — | 186.39 (16.68) | 597.31 (17.91) | 3.33 (10.20) | — | — | 7.83 (5.76) | 78.45 (9.26) |
| Pancreas Tumor | 44.96 (2.62) | 14.96 (12.21) | 9.95 (17.82) | — | 5.43 (58.64) | 22.63 (11.60) | — | — | — | — | 9.49 (8.23) |
| Pancreas Healthy | 98.10 (2.64) | 18.21 (48.23) | 14.85 (11.77) | — | 6.79 (27.57) | 10.88 (7.42) | — | — | — | — | 10.33 (7.81) |

TABLE 5

Log-transformed expression ratios for 250-ng assays. Top number in each entry is the mean of the log-transformed ratios of tumor amount-to-healthy amount of the indicated target in the specified tissue over three trials; bottom number in parentheses is the standard deviation. Entry spots in red indicate dysregulation. Entry spots lacking data indicate that the ratio was not calculated.

| | let-7a | miR-21 | miR-29b-2 | miR-143 | miR-145 | miR-146a | miR-181b-1 | miR-222 |
|---|---|---|---|---|---|---|---|---|
| Lung | −0.5119 (0.0161) | 0.3020 (0.0245) | −0.3911 (0.0225) | −0.5670 (0.0364) | −0.7870 (0.0450) | 0.3232 (0.0127) | −0.3066 (0.0194) | −0.6210 (0.0364) |
| Breast | −0.0942 (0.0349) | 0.2532 (0.0416) | 0.1378 (0.0777) | −0.4318 (0.0137) | −0.4801 (0.0194) | −0.3168 (0.0433) | −0.0266 (0.0529) | −0.8253 (0.0591) |
| Stomach | −0.3310 (0.0747) | 0.0966 (0.0031) | −0.3844 (0.1547) | −0.3877 (0.0107) | −0.5336 (0.0252) | 0.6007 (0.0282) | 0.3294 (0.3374) | −0.0935 (0.0716) |
| Pancreas | −0.3023 (0.0345) | −0.0198 (0.1183) | −0.1402 (0.0778) | −0.1251 (0.2381) | 0.3534 (0.1019) | — | — | 0.1785 (0.1382) |

This high-performance nucleic acid profiling system and platform is therefore shown to employ a versatile scanning and labeling methodology that enables the use of graphically-encoded hydrogel microparticles. The system's unprecedented combination of sensitivity, flexibility, and throughput offer exciting possibilities for discovery and clinical applications, particularly in the quantification of low-abundance miRNA and other biomolecules in readily-accessible media like serum.

Example 9

Scanning of Multiple-Event Particles

Figure 19:
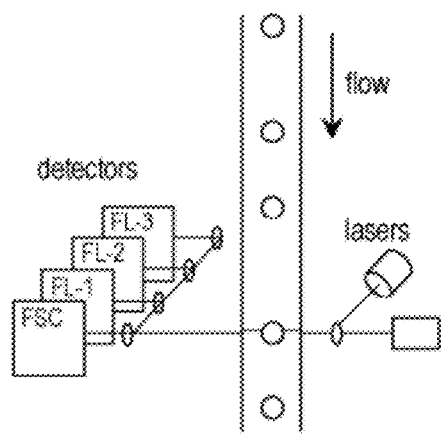
FIG. 19 illustrates a conceptual example of how scanning of multifunctional particles could be implemented. Standard cytometery records "events" as instances where the signal from a selected detector breaks a threshold, recording single beads as single events, and saving data for each channel. Multifunctional particles bear functional regions that can be doped with triggering entities (that cause scatter for instance) and single particles are recorded as multiple events. By analyzing the shape and time-sequence of these events, and by appropriately designing particles, one can reconstruct from this series of events, which ones belong in the same particle.
Figure 19:
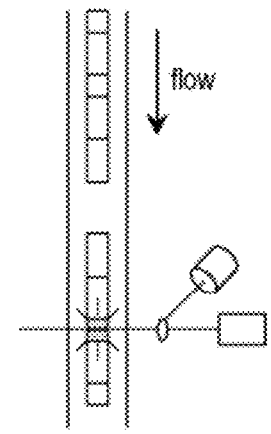
Figure 19:
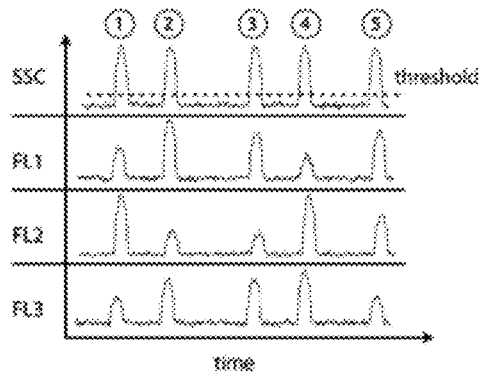
Figure 19:
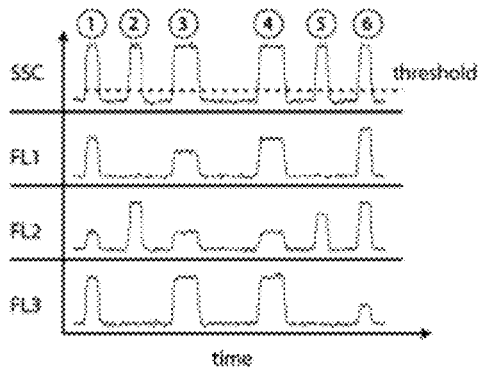

An example of how our approach is distinguished from standard cytometery is shown in FIG. 19 below. In this example, the functional regions of multifunctional particles can be loaded with entities that cause scatter of the illumination, which in turn triggers the cytometer to record an event.

We show a particle architecture that has two encoding regions and a single probe region where target is captured. The two code regions have varying levels of fluorophores embedded to give distinct signatures of fluorescence in the three fluorescence channels. One code regions is intentionally wider than the other in order to indicate particle orientation. The target could be labeled with a fluorophore that preferentially appears in a single fluorescence channel, as shown. In this example, each particle would be reported as 3 events. Of these three, the first and last would give code information while the second event would be used for target quantification. In this manner, the code and captured target are quantified non-contemporaneously.

We performed preliminary experiments to demonstrate the implementation of this methodology. We synthesized multifunctional particles that were ~200×35×30 μm with two fluorescent regions (30 μm and 60 μm, each dyed with Cy5 and Cy3 fluorescent dyes) flanking a broad inert region. The particles were run through an Accuri C6 cytometer with a flow rate of 100 μl/min and a core size of 40 μm. The threshold was set at 100,000 on FL4-H (which detects Cy5).

Figure 20:
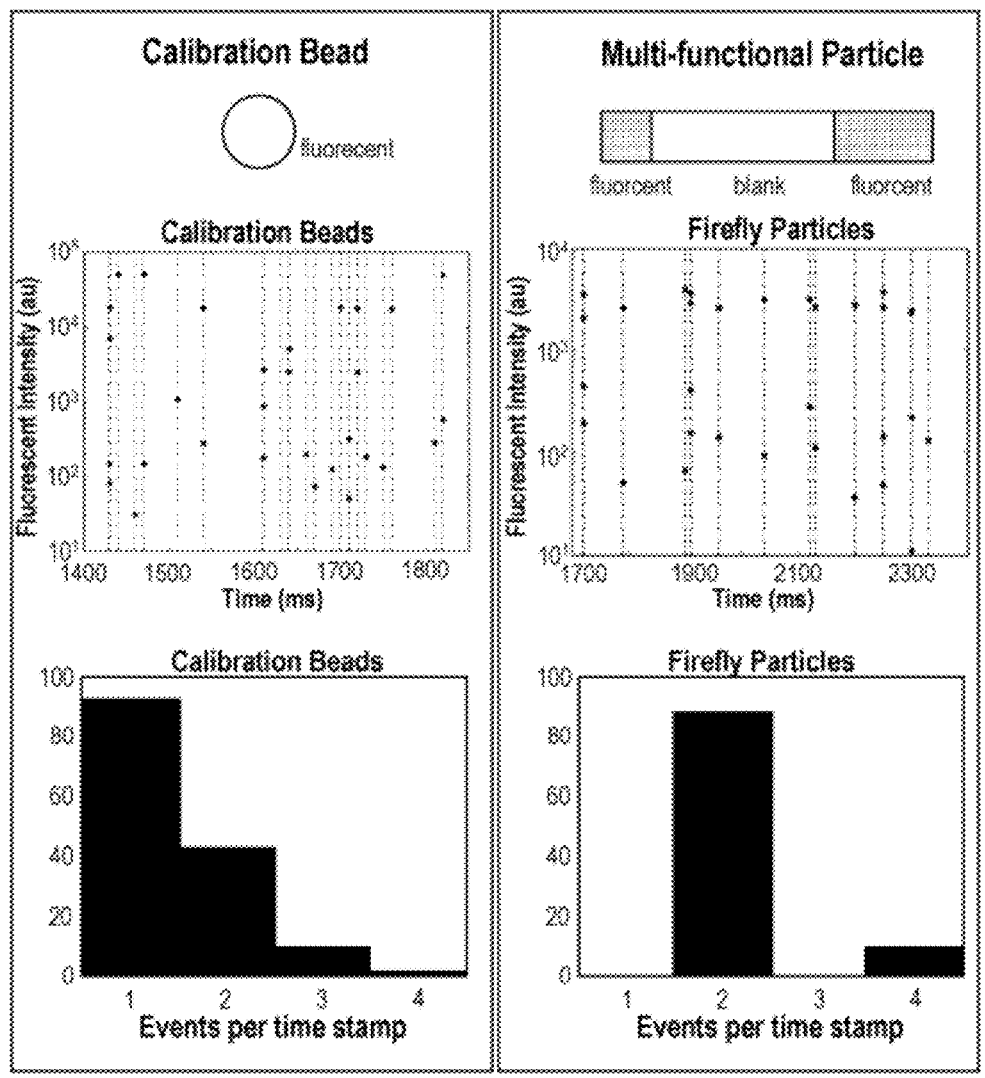
FIG. 20 illustrates exemplary comparison of scanning fluorescent calibration beads versus multifunctional particles. Shown is particle design (top), recorded events at each 1 ms timestamp (middle), and distribution of events per timestamp for timestamps where at least one event was recorded for calibration beads and multi-functional particles with two fluorescent regions (bottom).

Each event recorded by the cytometer is given a timestamp with a resolution of 1 ms. As particles typically move at rates of ~1 m/s through the flow cell, the interrogation of a particle that is 200 μm long is expected to last ~0.2 ms. As such, it can be expected that the two events recorded from a single multifunctional particle would appear in the same timestamp. To show that each particle was being read as two separate events, we plotted a histogram showing the count of timestamps that had a given number of events. We would expect the number of events per timestamp to be even for our particles (2 events for a single particle, 4 events for two particles, etc.), and both odd and even for regular particles. As a control, we also ran standard Accuri 8-peak calibration beads, with a typical spherical shape. The results are shown in FIG. 20.

As can be seen, the calibration beads are scanned fairly randomly throughout the course of data acquisition, giving a range from 1-4 beads/timestamp. The multifunctional particles, on the other hand, show clustering of 2 or 4 events per timestamp, which lends very well to the theory that each particle is being read as two events. In addition, it can be clearly seen from the plots of event vs. time that during each timestamp, there is a high- and low-level fluorescence reading. The particles were designed to have one bright and one dim region of fluorescence in the FL-2 channel, which also gives support to the theory that each particle is being read as two discrete events. This approach can be applied to three or more events per particle as well. Each region/event can vary in terms of fluorescence level, forward or side scatter, and width.

In some cases, it is useful to incorporate distinct levels of multiple fluorophores into each code region of the multifunctional particles. As a proof-of-concept, we used rod-shaped particles, 200×35×30 μm, with a single 60 μm code region on one end. The code region was labeled using four distinct levels of Cy3 and Cy5 fluorescent dyes. Particles were analyzed using the Accuri C6 cytometer with a flow rate of 100 μl/min, a core size of 40 μm, and a threshold of 5000 on FL4. The results are shown in FIG. 7 below.

The plot in FIG. 7 shows that it is possible to create a distinct fluorescent fingerprint in each code region of multifunctional particles. Each cluster of data points represents a distinct code.

For data analysis using this approach, an algorithm will be needed that groups events into particles, orients the particles, normalizes fluorescence against a standard if desired, and quantifies the fluorescence, scatter, or event width in each code and probe region. The corresponding code for each particle can then be given a confidence level, and those that were not called with a pre-defined level of confidence can be excluded from the analysis. The fluorescence in the probe region can then be used to determine the amount of target present in the sample analyzed. This system can be easily automated using software that performed analysis during or after scanning.

Example 10

Reading of Raw Signal

This Example demonstrates interrogating multifunctional particles in standard flow cytometers. In some embodiments, interrogation is performed to acquire signal from a cytometer detector before it is processed into events by the machine's firmware and use custom software to identify, orient, and analyze particles scans. We performed proof-of-concept scanning of particles in this manner, using three separate cytometers from Partec, Accuri (C6), and Millipore (Guava).

To gather raw data, we used the leads (Partec and Millipore) or QC pin (Accuri) from a single PMT in each cytometer, connected them through a simple circuit (often just a single resistor), and measured the voltage using a standard data acquisition (DAQ) board (National Instruments NIDAQ-USB6250). A custom script written in Python was used to communicate with the DAQ board, allowing the user to input how many samples to acquire and at what frequency. Samples were taken at rates ranging from 60 kHz to 1 MHz. After acquisition, the data were stored in a single file.

For analysis, we applied Fast-Fourier-Transform-based filtering to isolate the desired frequency response for each scan. Then, particles were identified in each sample by setting a threshold. If the signal was found to be above the threshold for a predefined number of samples, the region of interest and its flanking data points were stored as a single particle scan. Design features built in to each particle were used to identify code and probe regions. In addition, each signal could be normalized by a given feature on each particle. Our barcodes in this example consisted of series of stripes along the particle that had varying levels of fluorescence.

Figure 21:
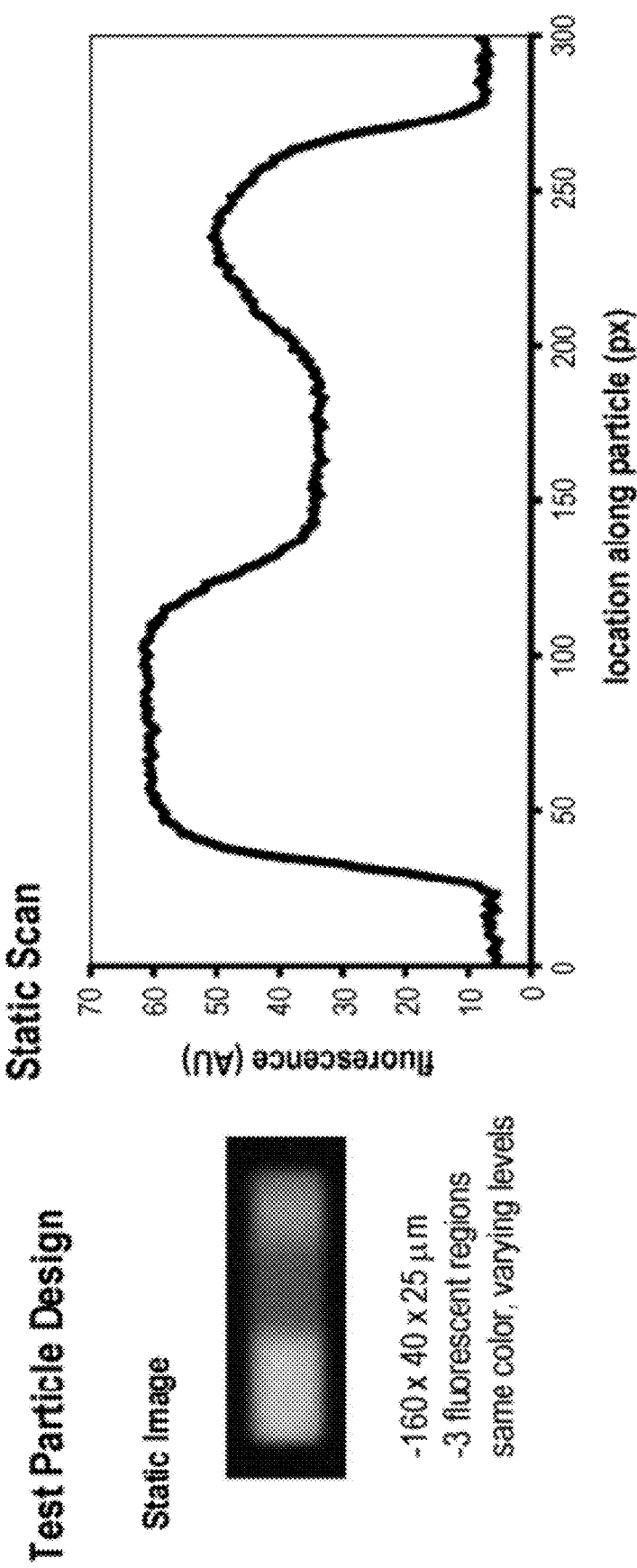
FIG. 21 illustrates exemplary design and use of a standard set of test particles to assess alignment and consistency of scan.
Figure 22:
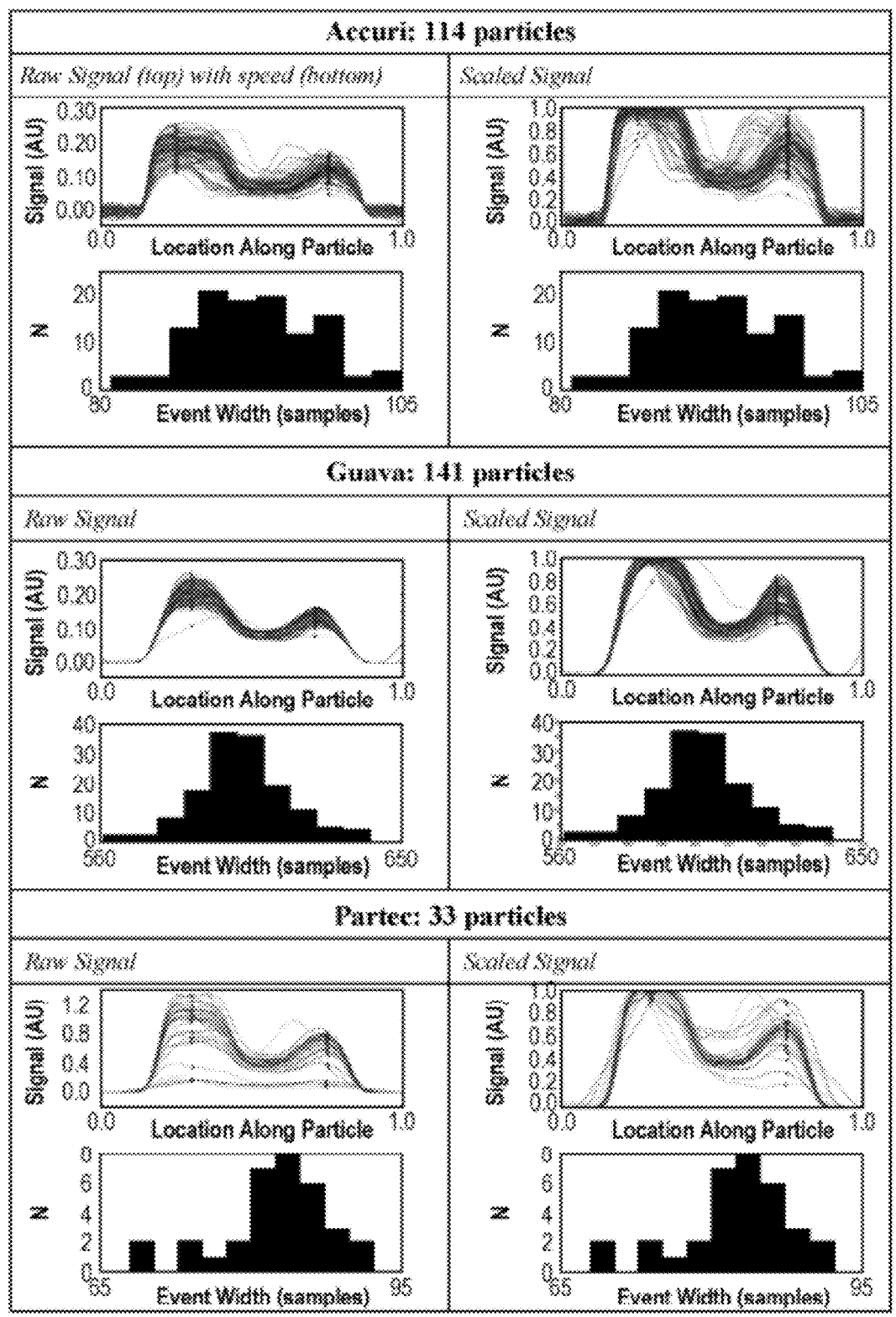
FIG. 22 illustrates exemplary results of a standard set of test particles to assess alignment and consistency of scan.

We used a standard set of test particles to assess alignment and consistency of particle-to-particle scan in three commercial cytometers. We synthesized rod-shaped fluorescent particles bearing three distinct regions. Static image scans from regular fluorescence microscopy were compared to those acquired from the raw scans obtained from a single PMT of each machine. After applying FFT-based filtering to isolate the desired frequency response for each machine, the signal from each particle identified was scaled (x-axis only) to compensate for variations in speed and plotted along a common x-axis. Typical results are shown in FIG. 21 and FIG. 22 with overlain particle scans and distribution of event width (which inversely correlates with particle speed).

As can be seen, all three cytometers were capable of scanning multifunctional particles with varying levels of accuracy compared to the static scans. Notably, the Guava instrument showed very good reproducibility, but had rounded features, most likely due to a large laser spot size (~25 µm) compared to the dimension of each feature. The Accuri showed fairly reproducible scanning but a significant amount of noise. The Partec showed considerable variability in scan intensity, likely due to a laser spot size that did not span the entire flow cell—most likely, particle brightness was dependent on where the particle was positioned in the flow cell cross-section.

Nucleic Acid Detection

Figure 23:
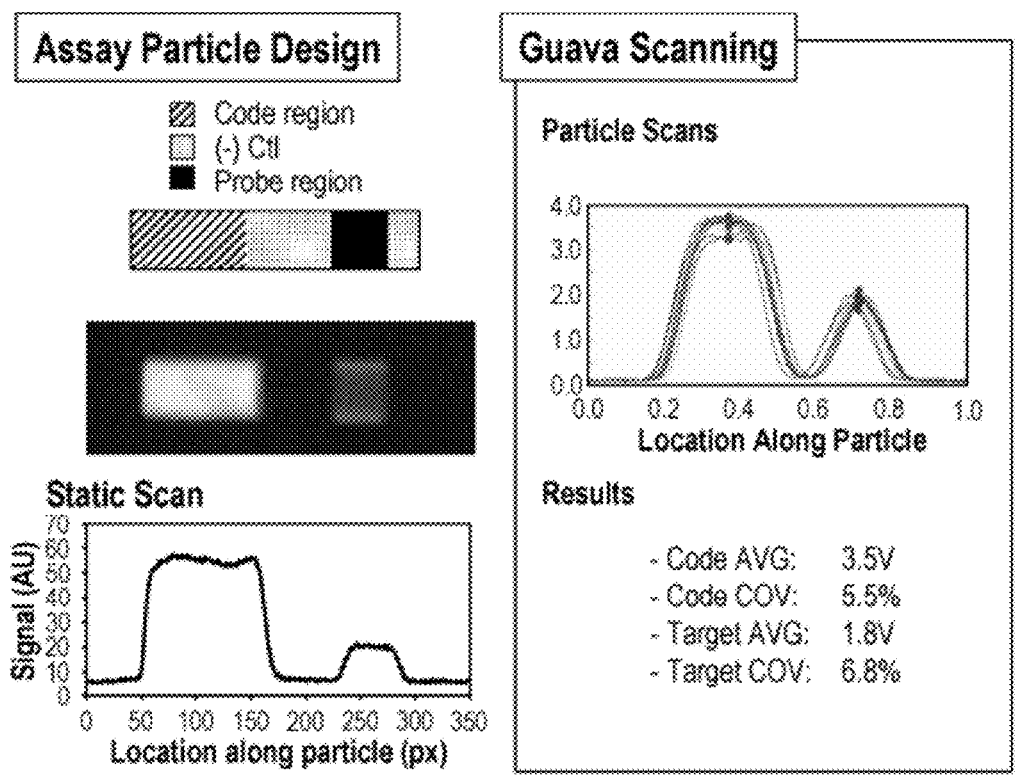
FIG. 23 illustrates exemplary results of nucleic acid detection using particles with a single, wide fluorescent region to represent a "barcode" and a narrow probe region.

We performed nucleic acid detection using particles with a single, wide fluorescent region to represent a "barcode" and a narrow probe region flanked by two inert regions. We detected microRNA let-7a spiked in at a level of 1 fmol into a 50 µl reaction with hybridization for 90 min at 55 C. Bound target was labeled with streptavidin-phycoerythrin and particles were scanned using the Millipore Guava. The level of fluorescence in the probe region of the particle indicated how much target was present in the assay. The results are shown in FIG. 23.

Again, the results were reproducible but showed rounding of signal at the interfaces between various particle regions. For the highest sensitivity, our assay would benefit from green (532 nm) laser excitation.

Example 11

Discrimination of Mature microRNA Targets from Precursors

According to the present invention, probes can be designed for labeling. This Example demonstrates detecting microRNAs using selective end-labeling to detect mature microRNA species without detection of precursor species.

We used a mature microRNA, the entire sequence of which is contained in one end of their precursor (3' or 5' depending on the exact microRNA species). If labeling is performed on the end common to both mature and precursor, both species are labeled and quantified. To selectively detect mature species, labeling can be accomplished on the opposite end of the mature species, the end sequence which is contained internally on the precursor. In the way, mature species can be detected without detection of the precursor.

To demonstrate the detection of only mature microRNA species, synthetic miR-143 mature and its precursor were used. The mature sequence for miR-143 appears on the 3' end of the precursor. The sequences for these species are given below in Table 6.

TABLE 6

Sequences for mature and precursor miR-143 species. The mature sequence is underlined in the precursor sequence.

| miR-143 Species | Sequence |
|---|---|
| Mature | 5'-UGAGAUGAAGCACUGUAGCUC-3' (SEQ ID NO: 20) |
| Precursor | 5'-GGUGCAGUGCUGCAUCUCUGGUCAGUUGGGAGUC<u>UGAGAUGAAGCACUGUAGCUC</u>-3' (SEQ ID NO: 21) |

Two batches of particles were used for this study—one contained miR-143 probe designed for labeling the 3' end of the target and the second contained a miR-143 probe designed for labeling the 5' end of the target. The probe and adapter sequences used in this study are shown in the tables below.

TABLE 7

Probe designs for labeling the 3' or 5' end of mature miR-143 species. The sequence for mature miR-143 is underlined in each probe sequence, and the remaining sequence is designed to capture the designated adapter for labeling.

| Probe (Target Label End) | Sequence |
|---|---|
| Probe 1 (3' End): | 5'acryl-GATATATTTT<u>AGAGCTACAGTGCTTCATCTCA</u>-3' (SEQ ID NO: 22) |
| Probe 2 (5' End): | 5'acryl-<u>GAGCTACAGTGCTTCATCTCA</u>ATTTATATTT-3' (SEQ ID NO: 23) |

TABLE 8

Adapter sequences for 3' and 5' labeling. Adapter 1 has a 5' phosphate group and 3' biotinylation, while Adapter 2 has a 5' biotinylation.

| Adapter (Target Label End) | Type | Sequence |
|---|---|---|
| Adapter 1 (3' End): | DNA | 5'phos-TAAAATATATAAAAAAAAAAA-3'bio (SEQ ID NO: 24) |
| Adapter 2 (5' End): | RNA | 5'biotin-AAAAAAAAAUAUAAU (SEQ ID NO: 25) |

Probes 1 and 2 were designed to label bound target on the 3' or 5' end of mature miR-143, respectively. For 3' labeling, a DNA adapter was used while for 5' labeling, an RNA adapter was used. These provided the most efficient ligation for the designated end of the RNA target.

Particles were incubated, in a buffer containing 0.5M NaCl in TE, for 90 minutes at 55 C with either 500 amols mature miR-143, 500 amols miR-143 precursor, or no miR-143 target. After hybridization, particles were washed in TE containing 0.05M NaCl. For particles bearing Probe #1, a ligation was performed with T4 DNA ligase at concentration of 0.8 U/ul and Adapter 1 at 40 nM. For particles bearing Probe #2, a ligation was performed with T4 RNA Ligase 2 at a concentration of 0.02 U/ul and Adapter 2 at 40 nM.

After 30 minute ligation at room temperature, particles were rinsed with TE containing 0.05M NaCl, and incubated with streptavidin-phycoerythrin reporter diluted to 2 ug/ml for 30 minutes at room temperature. After reporter conjugation, the particles were imaged using fluorescence microscopy. The signal-to-noise ratio, calculated as the average signal divided by the standard deviation of the signal from the negative control sample, was calculated for each miRNA species and labeling format. The results are shown in the table below:

TABLE 9

Typical results from labeling experiment using 3' and 5' labeling formats for mature and precursor miR-143 species. The signal-to-noise (SNR) represents the average fluorescence intensity signal divided by the standard deviation of the negative control signal.

| Labeling Format | miR-143 Species | SNR |
| --- | --- | --- |
| Probe/Adapter #1 (3') | mature | 75.9 |
|  | precursor | 33.9 |
| Probe/Adapter #2 (5') | mature | 21.6 |
|  | precursor | ND |

As can be seen, when Probe #1 is used with DNA ligase (Dnal) and Adapter #1, both mature and precursor miR-143 show detectable signal, although the precursor is at a much lower level. When using RNA ligase 2 (Rnal2) with Adapter #2, mature miR-143 is the only target that is effectively labeled, while the precursor species is not detected (ND) above SNR=3. This shows effective discrimination for the detection of mature miRNA detection over precursor species when labeling the 5' end of the target.

Example 12

Two-Strip Encoding with Probe Functionalization

This example demonstrated that compositions described herein may be synthesized and functionalized for encoding, in particular, universal encoding.

Figure 24:
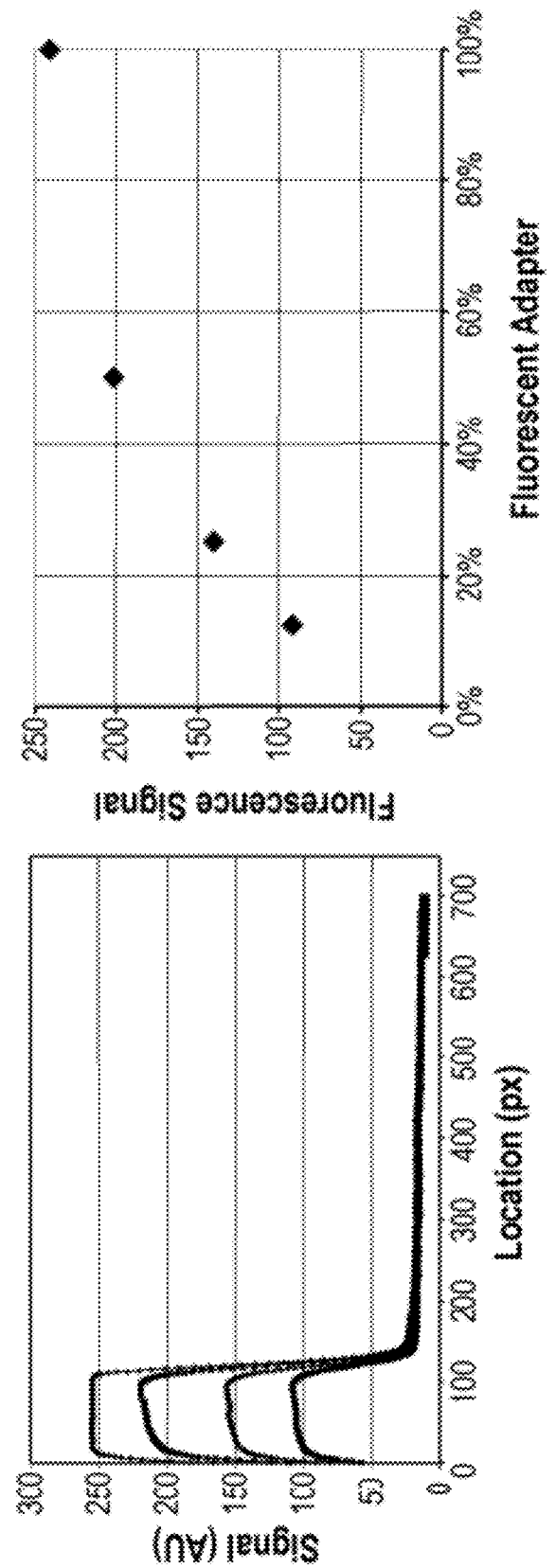
FIG. 24 illustrates exemplary results of average scans along the particle length (averaging over half of the width). The bottom signal, second lowest signal, second highest signal, and highest signal correspond to 12.5%, 25%, 50%, and 100% fluorescent ligation mix solutions, respectively.

Using stop-flow lithography as described in U.S. Pat. No. 7,709,554, the contents of which is incorporated herein by reference, we initially synthesized rectangular particles bearing a stem-loop encoding probe (SEQ ID NO:26) (/5Acryd/AATAAACACGGGAATAACCC, IDT, incorporated at 10 uM), negative control region, probe anchor (SEQ ID NO:27) (/5Acryd/GATATATTTT, IDT, incorporated at 50 uM), and a second negative control region. Particles were ~120×60×35 um and each of the 4 strips was ~30 um thick. Particles were incubated with varying ratios of fluorescently-labeled encoding adapter (SEQ ID NO:28) (5'-Phos-GTGTTTATAA-Cy3, IDT) to unlabeled adapter (SEQ ID NO:29) (5'-Phos-GTGTTTATAA-invdT, IDT). Each ligation mix contained NEBuffer #2 with 250 nM ATP, 200 U T4 DNA Ligase (all from New England Biosciences), and a total of 40 nM encoding adapters. Ligation was carried out for 30 min at room temperature, with mixing at 1500 rpm on a thermomixer. Afterward, particles were rinsed 3× with TE buffer containing 50 mM NaCl and 0.05% Tween-20. Particles were imaged on a Nikon Ti-S microscope using a 20× objective, NA=0.5, and a CCD Camera (Imaging Source). Scans of fluorescent intensity were plotted along the particle length and the fluorescent signals were measured and averaged for five particles in each sample. Typical results are shown in FIG. 24.

Data demonstrates that the labeling worked, but the relationship of fluorescence vs. adapter ratio was not linear. This implies a difference in hybridization or ligation rates between the fluorescent and non-fluorescent adapters used. Unfortunately, the images at the 100% level were saturated, so it is difficult to use all 4 data points for comparison. Raw and scaled data are shown in Table 10:

| RAW DATA | Sig | SD | COV | Normalized | Sig |
| --- | --- | --- | --- | --- | --- |
| 100% | 240.00 | 0.25 | 0.00 | 100% | 1.00 |
| 50% | 201.63 | 2.07 | 0.01 | 50% | 0.84 |
| 25% | 140.43 | 3.55 | 0.03 | 25% | 0.59 |
| 12.50% | 92.07 | 2.45 | 0.03 | 12.50% | 0.38 |

Furthermore, we used universal particles, synthesized using the stop-flow lithography process described above, bearing two encoding regions (with hairpin anchors) and a probe region (with linear anchor). Particles were ~180 um long, 35 um wide, and ~25 um thick with 4 regions—UCode1 (synthesized at ~10 uM), UCode2 (at ~10 uM), inert, and UAnchor (at ~50 uM). DNA sequences used in this study are as follows (as ordered from Integrated DNA Technologies, 5-'3'):

```
                                         (SEQ ID NO: 30)
UCode1 Probe = /5Acryd/AAT AAA CAC GGG AAT AAC CC (SEQ ID NO: 31)
UCode2 Probe = /5Acryd/AAT AAT GTG CCC AAT AAG GG (SEQ ID NO: 32)
UCode 1 Adapter Cy3 = /5Phos/GTG TTT ATT A/3Cy3Sp/

(SEQ ID NO: 33)
UCode 1 Adapter invdT = /5Phos/GTG TTT ATT A/
3InvdT/

(SEQ ID NO: 34)
UCode 2 Adapter Cy3 = /5Phos/CAC ATT ATT A/3Cy3Sp/

(SEQ ID NO: 35)
UCode 2 Adapter invdT = /5Phos/CAC ATT ATT A/
3InvdT/
```

After particles were synthesized and rinsed, we prepared Ligation Master Mixes, each with 250 nM ATP (NEB), 200 U T4 DNA Ligase (NEB), 0.05% Tween-20 (Sigma), and DNA Adapter (given below) in a total of 500 ul NEBuffer #2 (NEB):

F1: 80 nM UCode Adapter 1 Cy3

N1: 80 nM UCode Adapter 1 invdT

F2: 80 nM UCode Adapter 2 Cy3

N2: 80 nM UCode Adapter 2 invdT

In a 96-well, 1.2 um filter-bottom plate (Millipore), we added mixes of the ligation mixtures as listed in Table 11.

|        | F1 (ul) | N1 (ul) | F2 (ul) | N2 (ul) |
|--------|---------|---------|---------|---------|
| W1: 1, 1      | 100 | 0   | 100 | 0   |
| W2: 1, 0      | 100 | 0   | 0   | 100 |
| W3: 0, 1      | 0   | 100 | 100 | 0   |
| W4: 1, 0.25   | 100 | 0   | 25  | 75  |
| W5: 0.25, 1   | 25  | 75  | 100 | 0   |
| W6: 0.25, 0.25| 25  | 75  | 25  | 75  |
| W7: 0.25, 0   | 25  | 75  | 0   | 100 |
| W8: 0, 0.25   | 0   | 100 | 25  | 75  |

We then added 10 ul of particles to each well (~200 particles) and put the plate on mixer, and mixed at 1500 rpm for 30 min at room temp. We then used a filter unit to pull off excess buffer and rinse 2× with 200 ul TE buffer with 0.05% Tween-20 (TET). For imaging, we added 60 ul of TET to each well, mixed for 30 sec and then pipetted 35 ul from each well onto a glass slide. Each sample was sandwiched with an 18×18 mm coverslip. We image particles with Nikon Ti-U microscope with Imaging Source CCD camera with brightness=30, gain=600, exposure=0.412 sec, gamma=150. After imaging 5 particles per sample, we used ImageJ to orient and crop images, and plugged data into Excel for analysis. The raw data from the analysis are shown in Table 12 below, the ratios representing the amount of fluorescent adapter used (where 1=100%):

| ratio 1 | P1    | SD1  | COV  | ratio 2 | P2    | SD2  | COV  |
|---------|-------|------|------|---------|-------|------|------|
| 1.00    | 85.71 | 2.26 | 0.03 | 1.00    | 78.86 | 1.98 | 0.03 |
| 1.00    | 83.45 | 3.85 | 0.05 | 0.00    | 2.55  | 0.64 | 0.25 |
| 0.00    | 1.42  | 0.25 | 0.18 | 1.00    | 77.96 | 4.22 | 0.05 |
| 1.00    | 85.32 | 3.55 | 0.04 | 0.25    | 46.14 | 1.25 | 0.03 |
| 0.25    | 47.38 | 4.11 | 0.09 | 1.00    | 73.94 | 5.52 | 0.07 |
| 0.25    | 48.98 | 2.40 | 0.05 | 0.25    | 47.86 | 0.87 | 0.02 |
| 0.25    | 48.51 | 0.87 | 0.02 | 0.00    | 1.20  | 0.66 | 0.55 |
| 0.00    | 0.31  | 0.56 | 1.80 | 0.25    | 46.86 | 0.77 | 0.02 |

Figure 25:
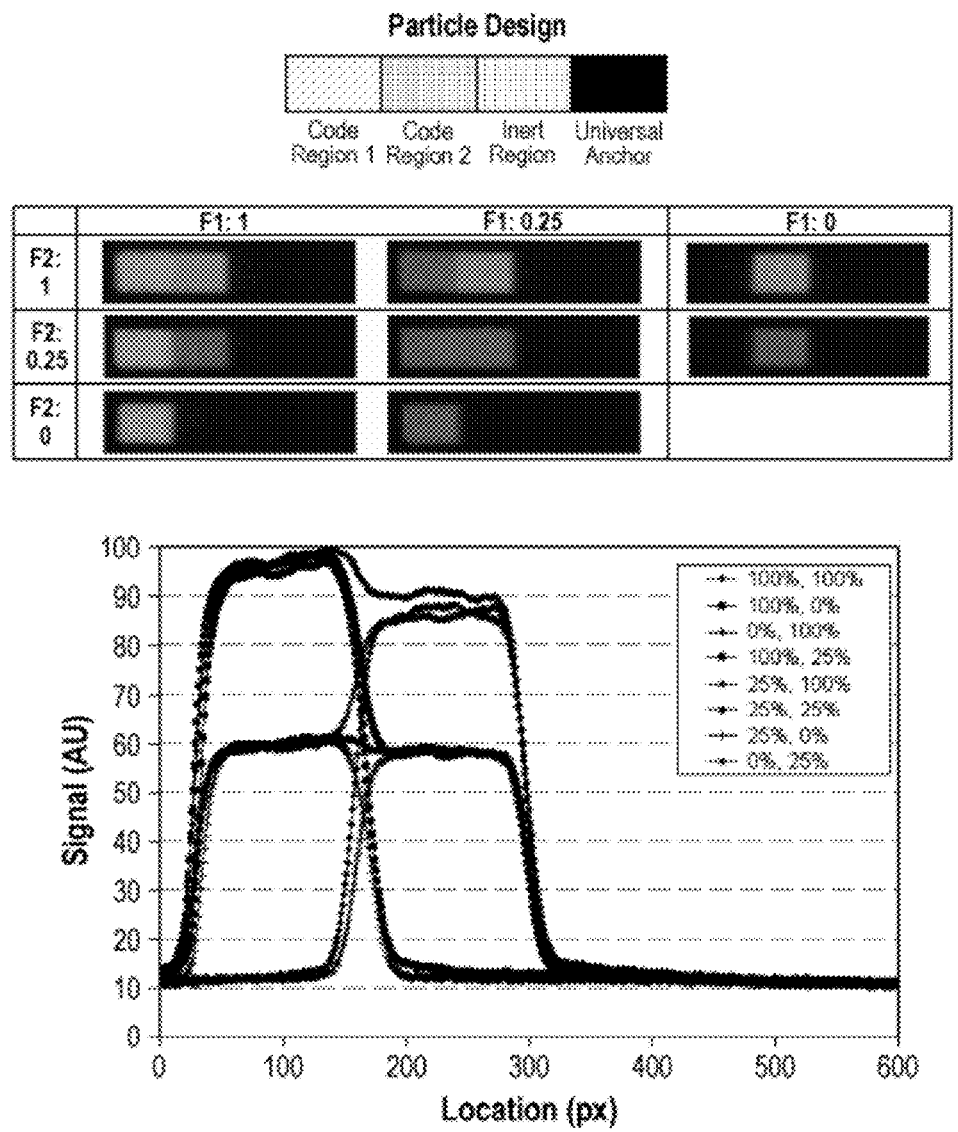
FIG. 25 illustrates examples of a) particle design and images for each mixture; and b) average scans over 5 particles for each mixture. (1 μm ~3.3 px, numbers in legend represent F1 and F2.)

Shown below (FIGS. 25 a and b) is a schematic of the particle design, sample fluorescent images from each ligation reaction, and average scans across particles.

Figure 26:
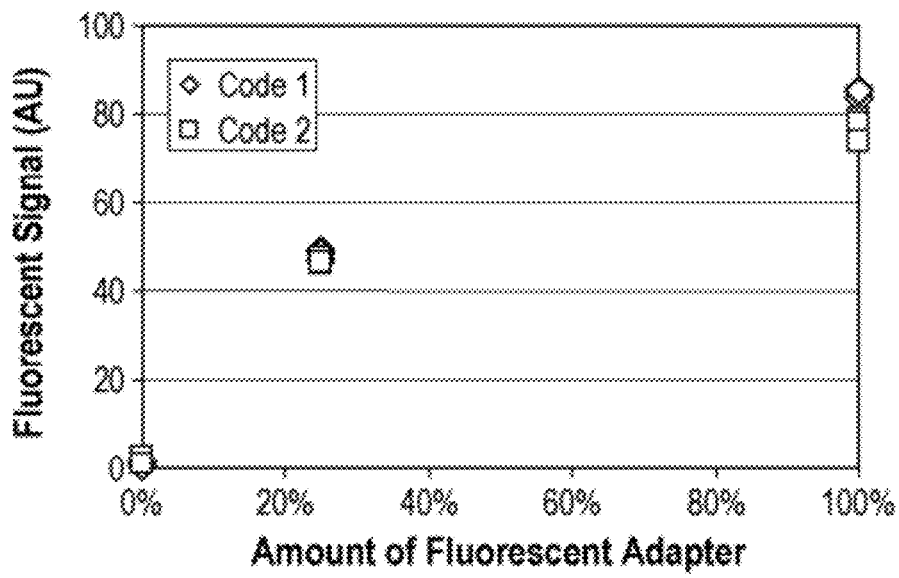
FIG. 26 illustrates exemplary results of measured fluorescence versus the adapter amount from each ligation mix.

A plot of the measured fluorescence versus the adapter amount from each ligation mix are shown in FIG. 26, where "Code 1" and "Code 2" represent the average signal in the first and second code region, respectively. The encoding worked well. More importantly, the encoding was specific; the signal for each code region seemed to be independent of the other. As observed in the above experiments, the fluorescent level of each code region was not linear with respect to the amount of fluorescent adapter. The signals were very reproducible, especially at the 25% fluorescent adapter levels.

Example 13

Universal Encoding Using Template Functionalization

In this example, universal particles were made, bearing several polynucleotide templates for encoding.

As an example, particles were designed such that there were three active regions separated by two inert regions, and they can be scanned by a commercial cytometer. The DNA templates with acrylate modification (denoted 5'acry) used for encoding are listed below in Table 13:

| Template name: | Sequence |
|----------------|----------|
| UC1 | 5'acry - AATAAACACGGGAATAACCC-3'<br>(SEQ ID NO: 36) |
| UC2 | 5'acry - AATAATGTGCCCAATAAGGG-3'<br>(SEQ ID NO: 37) |
| UC3 | 5'acry - AATAACTCTGGGAATAACCC-3'<br>(SEQ ID NO: 38) |

Figure 27:
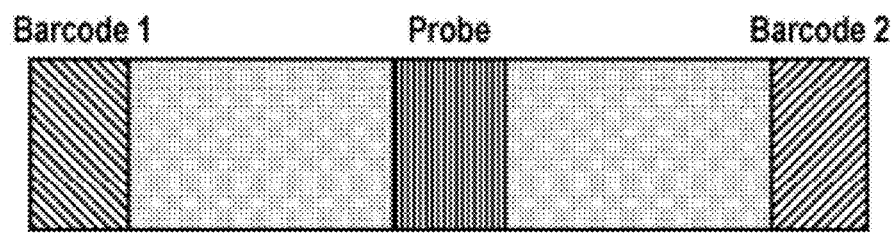
FIG. 27 illustrates exemplary general particle design for universal encoding.

These templates were used with particles of the design illustrated in FIG. 27. Hydrogel particles, consisting of poly (ethylene glycol), with this design were made using flow lithography as discussed above. The particles were made with monomers containing the following concentrations of polynucleotide templates as listed in Table 14.

|     | Barcode 1 | Inert | Probe   | Inert | Barcode 2 |
|-----|-----------|-------|---------|-------|-----------|
| UC1 | 50 uM     | NA    | NA      | NA    | NA        |
| UC2 | 2.5 uM    | NA    | 0.5 uM  | NA    | 2.5 uM    |
| UC3 | NA        | NA    | NA      | NA    | 50 uM     |

For use in a flow cytometer, the UC2 template is functionalized with a Cy5 modified adapter in order to trigger events in the RED2 channel. For barcoding, the UC1 and UC3 templates are functionalized with blends of adapters (Cy3 modified, FAM-6 modified, or non-fluorescent) in order to achieve distinct levels of fluorescence in the YEL channel of the cytometer for barcoding and distinct levels of fluorescence in the GRN channel for orientation. The sequences of the adapters used are given in Table 15 below:

| Adapter Name | Sequence (5'-3') |
|--------------|------------------|
| UC1-A-Cy3  | 5'phos - GTGTTTATTA - Cy3<br>(SEQ ID NO: 39) |
| UC1-A-NF   | 5'phos - GTGTTTATTA<br>(SEQ ID NO: 40) |
| UC1-A-FAM6 | 5'phos - GTGTTTATTA - FAM6<br>(SEQ ID NO: 41) |
| UC2-Cy5    | 5'phos - CACATTATTA - Cy5<br>(SEQ ID NO: 42) |
| UC3-A-Cy3  | 5'phos - AGAGTTATTA - Cy3<br>(SEQ ID NO: 43) |
| UC3-A-NF   | 5'phos - AGAGTTATTA<br>(SEQ ID NO: 44) |

| Adapter Name | Sequence (5'-3') |
|---|---|
| UC3-A-FAM6 | 5'phos - AGAGTTATTA - FAM6 (SEQ ID NO: 45) |

Figure 28:
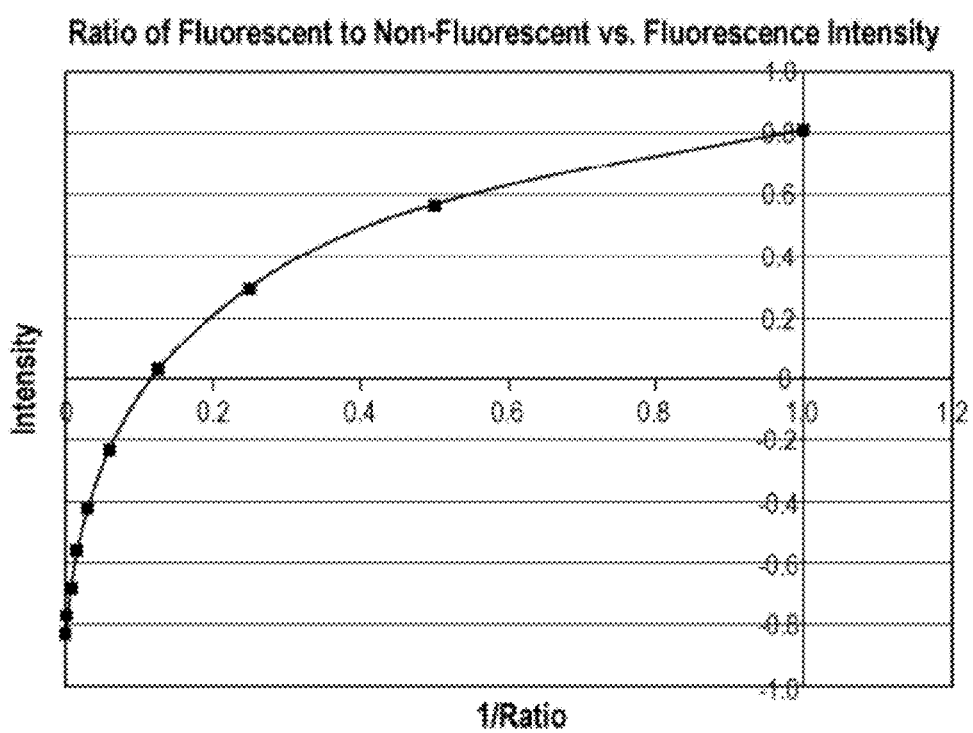
FIG. 28 illustrates exemplary fluorescent signal obtained in Barcode 1 region with varying ratios of fluorescent (Cy3) to non-fluorescent adapter.

The number of distinguishable fluorescence levels in each barcode region depends on the accuracy of encoding, and performance characteristics of the cytometer being used. To determine the proper code dilutions to maximize multiplexing on a given flow cytometer, several blends of fluorescent and non-fluorescent adapters may be tested for a given encoding template. Several ratios of fluorescent to non-fluorescent adapters were explored by logarithmically varying the ratio between fluorescent and non-fluorescent and ligating multiple batches of particles a curve was generated as seen in FIG. 28. Template functionalization via ligation with adapters was carried out simultaneously for all templates for one hour at room temperature using 0.8 U T4 DNA ligase per ul, 40 nM total adapter for each encoding template (fluorescent or non-fluorescent).

Several dilutions of UC1-A-Cy3 in UC1-A-NF were used to functionalize universal particles in order to develop a titration curve for the fluorescence obtained. The curve in FIG. 28 shows the log(fluorescence) obtained using ratios of Cy3:NF adapter ranging from 0:1 to 1:1. This curve was obtained using YEL fluorescence measurements from a Guava easyCyte 6HT.

Using this methodology, titration curves were made for the UC1 and UC3 templates with Cy3 modified and non-fluorescent adapters. Typical results, showing log(fluorescence), are given in Table 16 below.

| Barcode 1 | | | | Barcode 2 | | | |
|---|---|---|---|---|---|---|---|
| Ratio | 1/Ratio | Corrected Intensity | COV | Ratio | 1/Ratio | Corrected Intensity | COV |
| 0 | 0 | -0.79 | 17.40% | 0 | 0 | -0.8 | 10.80% |
| 256 | 0.0039063 | -0.78 | 17.00% | 256 | 0.00390625 | -0.81 | 8.70% |
| 128 | 0.0078125 | -0.74 | 20.40% | 128 | 0.0078125 | -0.78 | 11.60% |
| 64 | 0.015625 | -0.63 | 13.30% | 64 | 0.015625 | -0.74 | 10.20% |
| 32 | 0.03125 | -0.52 | 12.60% | 32 | 0.03125 | -0.69 | 11.70% |
| 16 | 0.0625 | -0.33 | 10.80% | 16 | 0.0625 | -0.6 | 10.00% |
| 8 | 0.125 | -0.1 | 10.00% | 8 | 0.125 | -0.44 | 9.00% |
| 4 | 0.25 | 0.15 | 10.90% | 4 | 0.25 | -0.25 | 9.20% |
| 2 | 0.5 | 0.43 | 10.90% | 2 | 0.5 | 0.01 | 9.20% |
| 1 | 1 | 0.69 | 12.90% | 1 | 1 | 0.28 | 11.40% |

Dilutions used for encoding were selected such that the expected fluorescence levels had very little chance of overlap with an adjacent dilution, given the expected coefficient of variation (COV) in the signals measured here. In order to obtain 5 levels for each barcode regions, the following dilutions of non-fluorescent to Cy3-modified adapters in Table 17 were used:

| Log (intensity) | Adapter NF:Cy3 |
|---|---|
| Barcode 1 | |
| -0.79 | 0 |
| -0.42 | 21 |
| -0.05 | 6.7 |
| 0.32 | 2.5 |
| 0.69 | 1 |
| Barcode 2 | |
| -0.80 | 0 |
| -0.53 | 17.7 |
| -0.26 | 4.1 |
| 0.01 | 2 |
| 0.28 | 1 |

With the possibility of generating 5 distinct levels of fluorescence in each Barcode 1 and Barcode 2, a total of 25 unique combinations can be obtained. These dilutions were tested with the universal particles synthesized in this Example. To differentiate the two coding regions, a higher level of green (FAM-6) was added to the dilution series for Barcode 2. The fluorescent adapter for UC2 was also included in the functionalization to generate signal in RED2 which was used to trigger events on the cytometer. Particles were functionalized via simultaneous ligation with blends of adapters for UC1, UC2, and UC3 such that the total concentration of adapter for a given adapter was 40 nM. Reactions were carried out at room temperature for 1 hour with 0.8 U/ul of T4 DNA ligase present. Particles were rinsed in TE buffer and scanned using a Guava 6HT.

Example 14

Scanning Multi-Event Particles with Commercial Cytometers

In this example, universal particles made in Example 12 was used for scanning using commercial cytometers. A Millipore Guave easyCyte 6HT-2L as an exemplary cytometer can be used for scanning.

Here, particles were scanned on a cytometer using RED fluorescence to trigger events, yellow fluorescence to encode particles, and green fluorescence to orient particles. As discussed, particles represented in FIG. 27 are comprised of three active regions (denoted Barcode 1, Probe and Barcode 2), separated by two inert regions. All three active regions contain a Cy5-modified nucleic acid to trigger events in the RED2 channel of a Guava easyCyte cytometer. The level of Cy5 in the probe region was intentionally made to be approximately one half that in the barcoding regions. The two barcode regions contain varying levels of Cy3-modified oligonucleotides. The levels of Cy3 in each barcode region, detected in the YEL channel of the Guava cytometer, are used to give the particle a unique encoding signature. In addition, a FAME-modified oligonucleotide is incorporated in the barcoding regions, with a higher level in Barocde 1, in order to provide a means of orientation. A mixture containing 25 different particle barcodes, with 5 unique levels of Cy3 fluorescence in Barcode 1 and 5 unique levels in Barocde 2, were used to demonstrate proof-of-concept.

Figure 29:
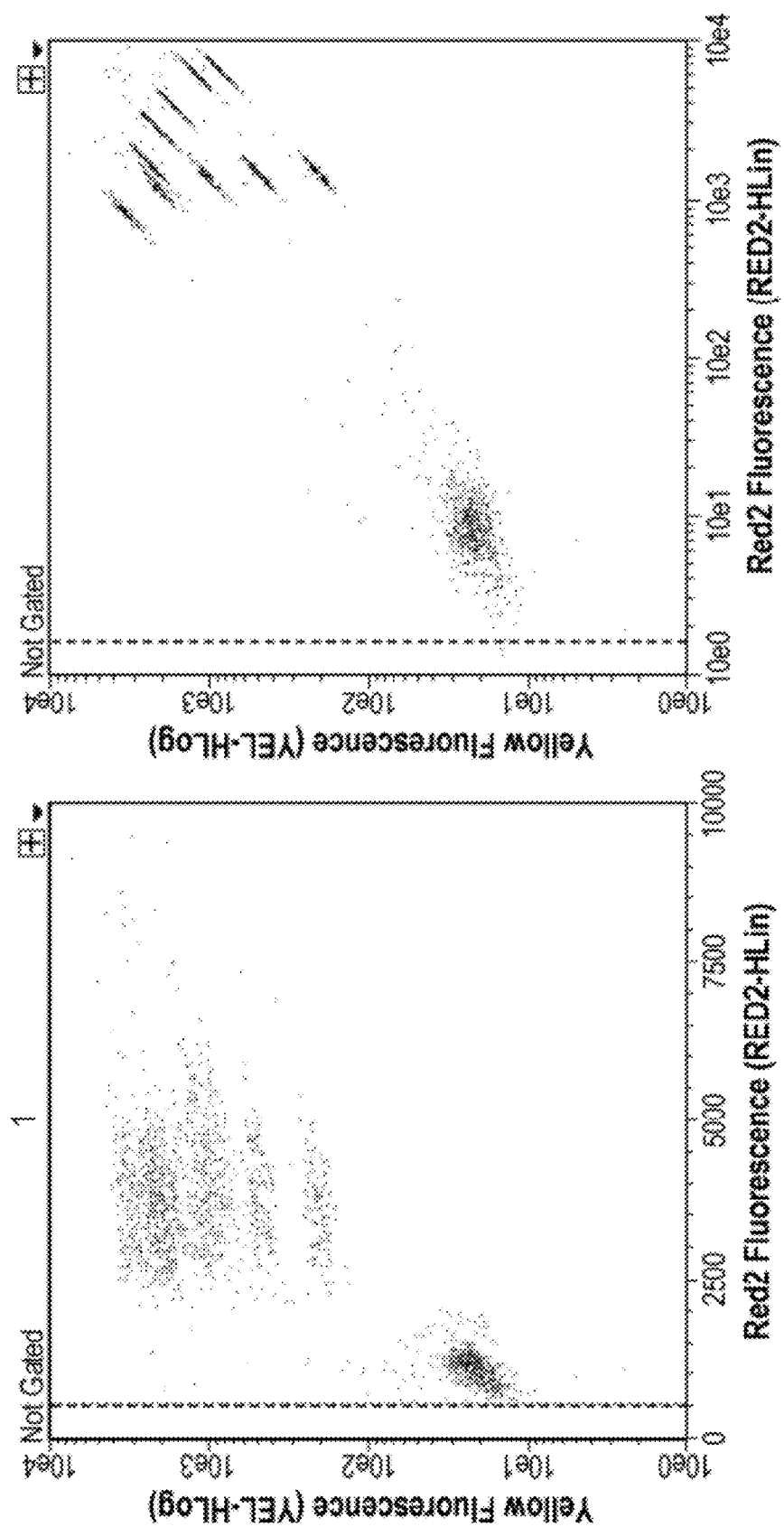
FIG. 29 illustrates exemplary plot of events associated with barcoded gel particles. Shown on the left is a plot of YEL fluorescence (used for barcoding) versus RED2 fluorescence (used for triggering) and on the right YEL fluorescence (used for barcoding) versus GRN fluorescence (used for orientation).

A threshold of 500 set on the RED2 channel with the Guava 6HT was sufficient to allow identification of all three regions of the particle. Hundreds of particles, at a concentration of approximately 20 per microliter in TE buffer, were scanned at 0.6 microliters per second. The events associated with the particles, plotted on YEL (barcoding color) versus RED2 (trigger color) are shown in FIG. 29, along with YEL versus GRN (for orientation). The probe region of the particle appears in the lower left hand side of the plot, with lower levels of green (FAM-6™) and yellow (Cy3™). The two coding regions of the particles show up as bands on the upper right hand corner of the plot. A total of ten bands can be discerned on the plot, comprising of five codes on the Barcode 1 region of the particle and five codes on the Barcode 2 region. The raw values represented on these plots are then exported into a FCS file for further analysis. All events exported in the CSV are store in temporal sequence.

Figure 30:
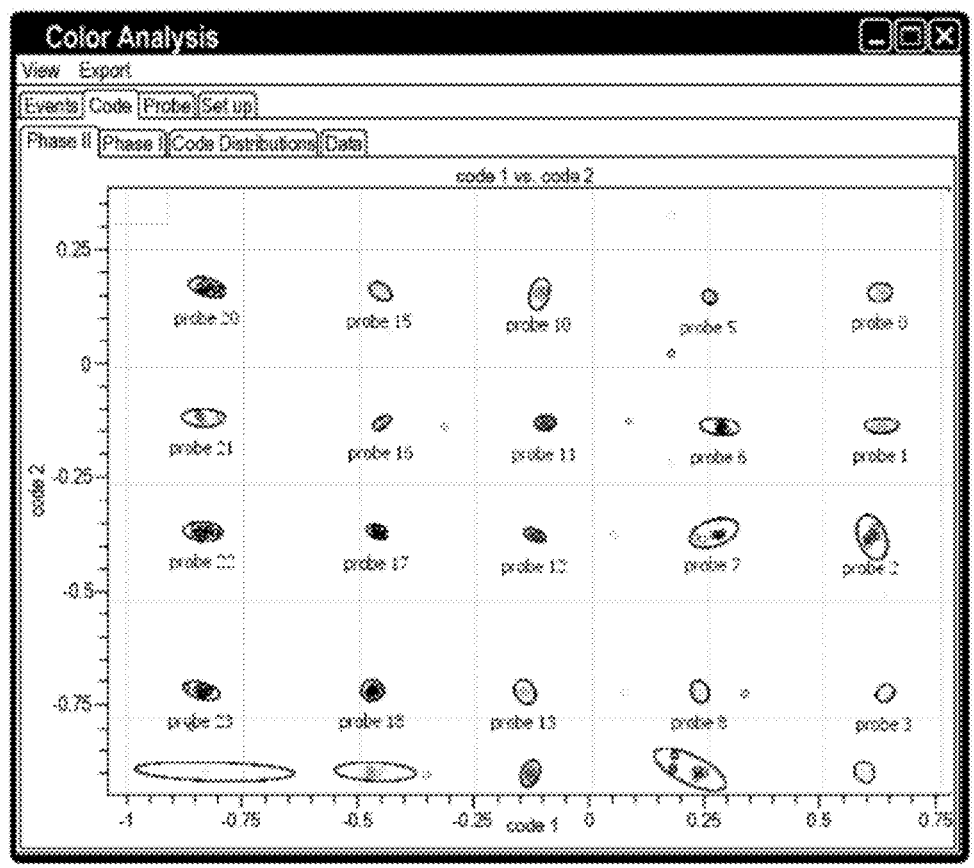
FIG. 30 illustrates exemplary demonstration of 25-plex encoding using 5 unique levels of YEL fluorescence on both Barocode 1 and Barcode 2 regions of encoded particles. These data have been reconstructed from raw events saved in a FCS file from the Guava software.

Custom software was used to analyze the events exported from the Guava software and reconstruct them, based on patterns in the RED2 and GRN fluorescence. The software sorts through the sequence of events to assess whether three subsequent events fit the expected patterns for RED2 and GRN fluorescence. If the pattern is fit, the events are grouped as a particle and can be analyzed for barcode in YEL fluorescence and oriented by GRN fluorescence. After reconstruction, a more coherent plot can be composed using the level of yellow intensity (Cy3™) on Barcode 1 vs. that of Barcode 2 (designated code 1 and code 2, respectively). This plot is shown in FIG. 30. Ellipses are used to identify clusters of particles that are associated with each of the 25 barcodes present. As can be seen, the five levels of fluorescence in Barcode 1 (code 1) and Barcode 2 (code 2) can be readily distinguished.

In addition to determining the barcode, the custom software also quantifies the fluorescence associated with captured target in the probe region of the particle, the information of which is stored as the second of the three events associated with a particle. When using a reporting fluorophore that can be detected in the YEL channel, the level of YEL fluorescence in this region indicates the quantity of target present.

Example 15

Development of One-Spot Isothermal Nucleic Acid Amplification Assays

Figure 31:
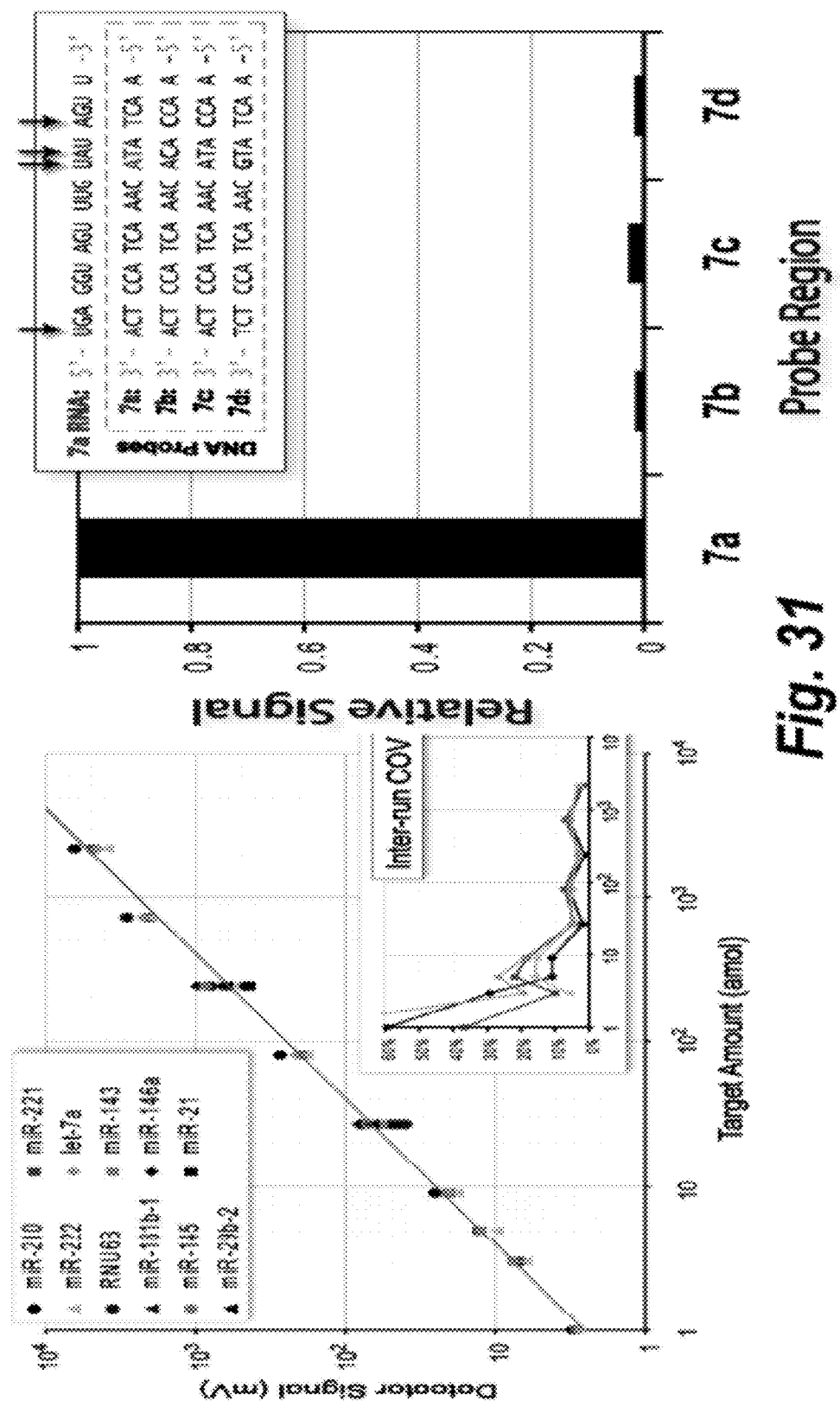
FIG. 31 illustrates exemplary demonstration of attomole sensitivity (left), >3 log dynamic range (left), and single-nucleotide specificity (right) using Firefly BioWorks' custom assay for microRNA targets. We used Firefly's 3-hour assay (total RNA to results) to detect dilutions of eleven microRNA targets spiked into 250 ng of E. coli total RNA, reporting the average detector signal versus spike-in amount with inter-run COV (inset). Specificity was assessed by spiking let-7a RNA target samples containing particles bearing probes for let-7a, 7b, 7c, and 7d—each which varied by only one or two nucleotides (right).

This example further illustrates using encoded particles in accordance with the present invention in various applications, such as nucleic acid amplification assays. As previously demonstrated, we has developed various compositions and methods, providing (1) sub-attomole sensitivity, (2) single-nucleotide specificity, (3) rapid scanning, (4) a virtually unlimited encoding density, and (5) low cost. For example, the high performance of our assay is shown for microRNA targets in above Examples, and FIG. 31. The simplicity of our particle synthesis, one-pot assay, and single-color detection described herein enables a new class of low-cost diagnostic tools.

Figure 32:
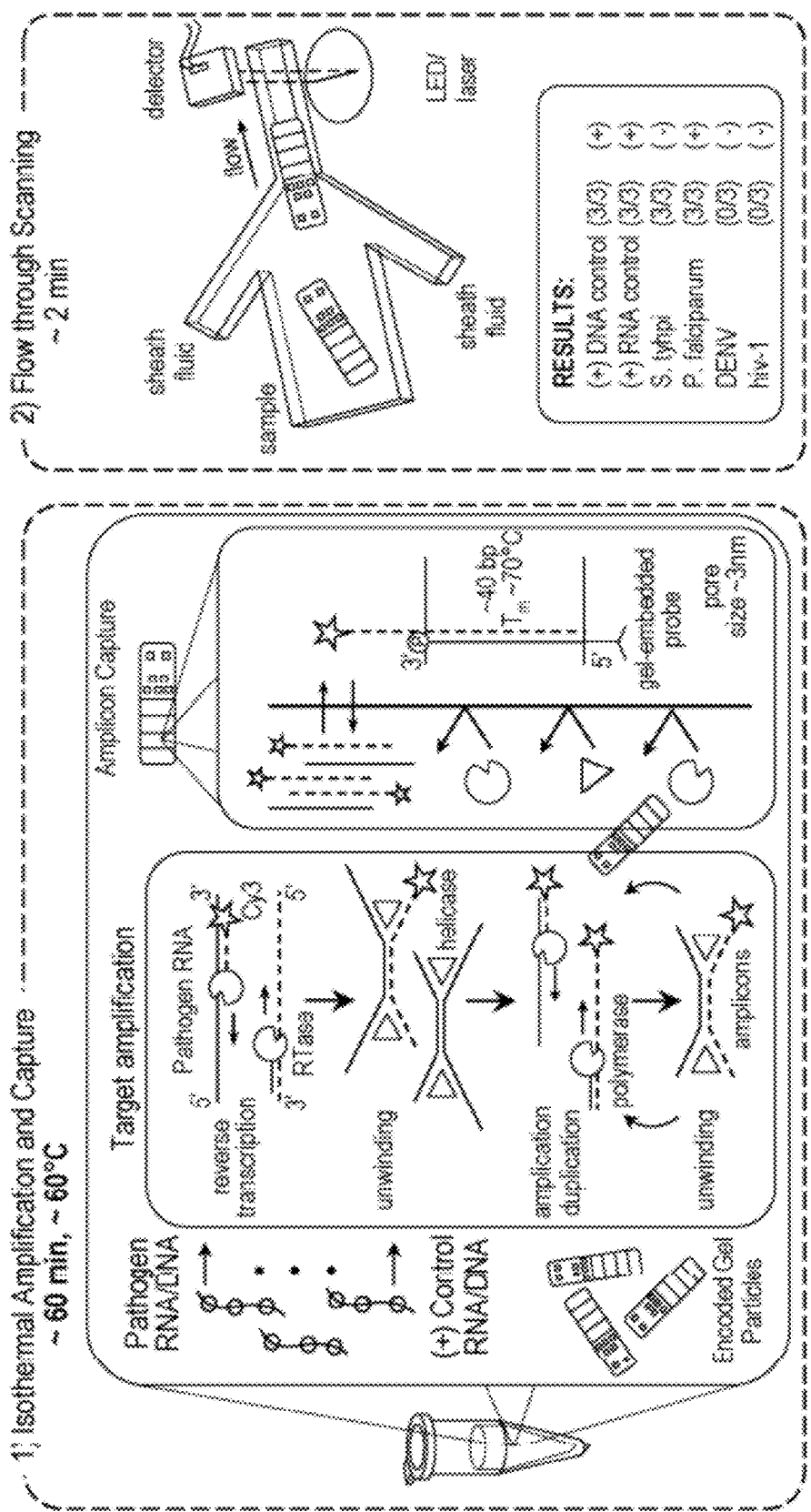
FIG. 32 illustrates exemplary multiplexed isothermal amplification and capture assay for panel-based pathogen detection. Fluorescent amplicons generated using reverse transcription helicase-dependent amplification (RT-HDA) will be captured on encoded hydrogel particles in a single step. Each particle, bearing probe regions for three signatures of a given species and porosity-tuned to exclude helicase penetration, will immediately be scanned in a microdevice without the need for rinsing. The high sensitivity of encoded gel particles and two-levels of specificity (amplification and hybridization) will mitigate false-positive or negative reads.

In this project, we will use encoded hydrogel particle assay to develop a point-of-care system that (1) can perform accurate panel-based tests on DNA or RNA from >10 pathogens at once, (2) uses a one-pot, isothermal assay that is rapid and easy to use, and (3) utilizes low-cost disposable cartridges in a hand-held device. We are developing one-pot assays in which we amplify specific genomic targets of pathogens, hybridize the amplicons to barcoded gel particles, and quantify the bound amplicons in a single closed tube, with a single user intervention (sample loading). Multiple species-specific targets will be amplified using isothermal, helicase-dependent amplification (HDA). Fluorescently-labeled amplicons will be free to diffuse into the encoded hydrogel particles and hybridize to their complementary nucleic acid probes embedded throughout (FIG. 32). The flexibility of our innovative microfabrication process allows us to precisely tune the pore size or particles to exclude helicase enzymes (~4.5 nm), which would unwind bound targets. Due to this advantage, the whole process can be carried out without user intervention. After <1 hour, particles will be scanned rapidly in a flow-through channel using fluorescence to read the barcode of each particle and quantify the corresponding targets. It is our intention to make the system cartridge-based with disposable units that can be interfaced with a portable analysis unit.

Figure 33:
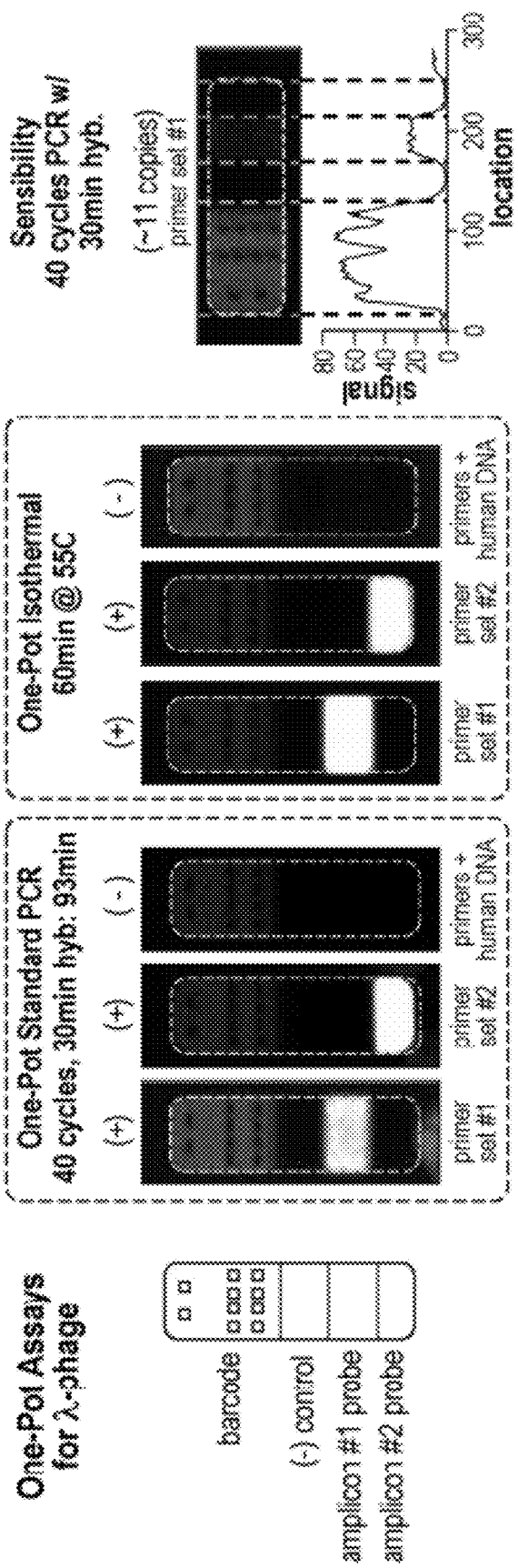
FIG. 33 illustrates exemplary proof-of-concept one-pot assays using standard PCR and isothermal amplification, demonstrating specificity of amplification and sensitive detection of ~11 template copies. We assessed the specificity of amplification for two targeted regions of λ-phage DNA, using a one-pot reaction with probes designed against the amplicons generated by two separate primer sets. Template λ-phage was spiked into (+) samples at ~11,000 copies for specificity tests, though we were also able to detect amplified product with only ~11 copies present (right). For specificity against human genomic DNA, we spiked ~11,000 copies of human genomic DNA into the reaction with no λ-phage present.

We further developed one-pot assays as described in various embodiments above, using standard PCR and has recently begun to investigate isothermal assays for the purpose of this project. We used λ-phage DNA as a model system for assay development. First, we designed Tm-matched primers against 2 target regions of lambda with a cross-check against human genomic DNA to avoid non-specific amplification. The amplicons were designed to be ~60 bp in length. Probes were designed to target each amplicon, containing the complementary sequence excluding the binding site for the forward primer. We performed one-pot assays using both standard PCR and isothermal amplification (FIG. 33).

For each assay, we prepared PCR mixes containing a single primer set (forward primer labeled with Cy3), ~50 encoded gel particles with two spatially-separated probes regions for the amplicons, and either λ-phage DNA or human genomic DNA. Using both standard PCR and isothermal amplification, we were able to show specific amplification and hybridization for each amplicon generated and no non-specific amplification of human genomic DNA. We performed a serial dilution of λ-phage from 11,000-11 copies per reaction. Using primer set #1, we were able to detect ~11 copies of template in our preliminary studies using a one-pot assay with standard PCR. Although sensitivity has not been assessed for the isothermal reaction, the signals observed on particles after 60-min reaction were stronger than those obtained from standard PCR after 40 cycles.

Design of Amplification Primers and DNA Detection Probes

For any pathogen, it is necessary to identify genomic targets that are both specific to the pathogen, and conserved over strains. We will build on the work of others developing PCR-based assays for the four pathogens of interest. Targets for genomic HIV RNA include: the pol-integrase region and the env and gag genes. Targets used for PCR-based identification of for typhoid bacterium genome include the tyv, flag, viaB, and ratA genes. Conserved regions for the malarial parasite genome include the 18s rRNA gene and the circumsporozoite (CS) gene. For dengue virus, Gurukumar et al. targeted a conserved region in the 3'UTR of the viral genome. Initially, our experiments are designed to target similar regions for these pathogens.

For multiplexed isothermal amplification, it is necessary to design compatible primer sets that (1) have similar melting temperatures, (2) do not form hetero-dimers, and (3) specifically and efficiently amplify the targets identified for each pathogen species. Because we are developing a "one-pot" assay where the particles are present in the amplification reaction, we have additional considerations including (1) avoiding 3'-extension of the DNA probes embedded in the particle probe-regions, and (2) keeping amplicons small (<100 bp) for rapid diffusion into our particles where they will hybridize. In approaching this challenge, we will learn from an extensive body of literature for primer design in multiplexed amplification.

Figure 34:
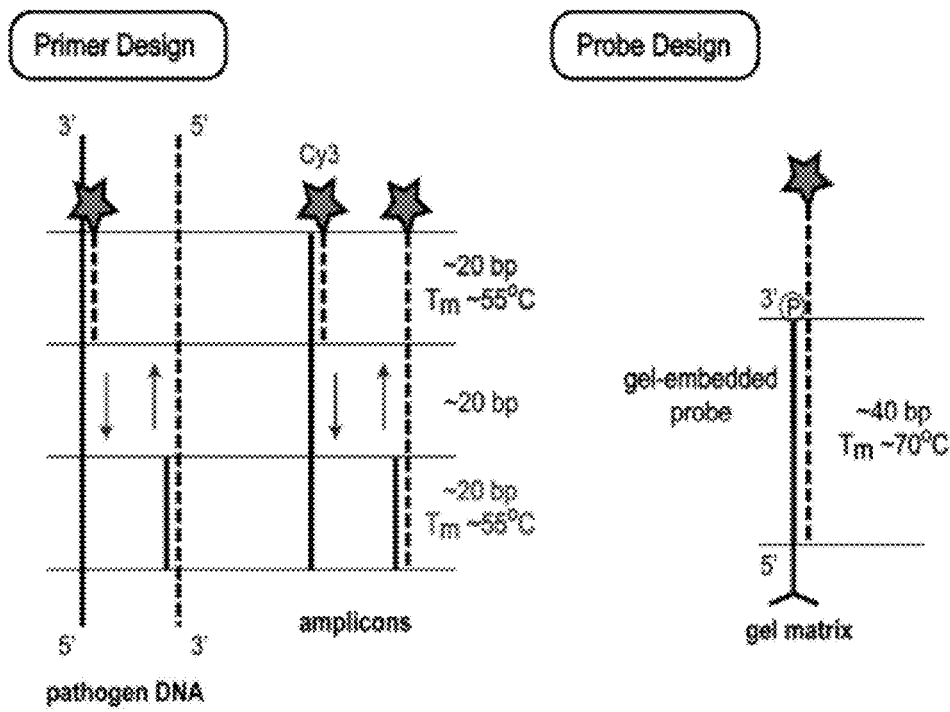
FIG. 34 illustrates exemplary amplification primer (left) and amplicon probe (right) design for multiplexed detection assays. Forward primers will have a single Cy3 fluorophore. Probes will be designed to have a T$_m$ than primers and will be 3' phosphorylated to avoid incidental 3'-extension.

As shown in FIG. 34, primers will be designed to have melting temperatures near 55° C., be ~20 bp in length, and provide amplicons ~60 bp in size. The forward primers will contain a single Cy3 label for fluorescence detection. For each of the pathogen species, we will design several sets of primers that meet the aforementioned requirements. Primer design will be accomplished as follows:

First, potential primers sets will be identified for the species of interest (dengue, typhoid, malaria, and HIV as well as λ-phage and MS2 controls) for commonly-targeted, conserved genomic regions using a primer-design program like Primer3.

Second, each potential primer identified will be assessed for species-specificity via BLAST search.

Third, a script will be written in MATLAB to assess dimer-formation with all other primers (using nearest neighbor calculations), and to identify a total of 30 primer sets (5 for each of the four pathogens and two controls) that meet all requirements.

Optimization of Helicase-Dependent Amplification (HDA) for DNA Detection.

To maximize the probability of success in developing a working isothermal amplification technique, we will begin with commercially available kits and standard protocols, using λ-phage as a model system. We will use the IsoAmp® kit (New England Biosciences) to perform isothermal amplification on ~5000 copies of λ-phage spiked into human genomic DNA as a model system. We will optimize several parameters including (1) primer concentrations (from 0.1 μM-10 μM), (2) primer length (from 20-26 bp), (3) amplification temperature (from 50-65 C), and (4) reaction time (from 10-120 min). The efficiency and yield of the isothermal reaction will be assessed and compared to the yield of a standard 30-cycle PCR reaction that utilizes the same primers and target regions. Polyacrylamide Gel Electrophoresis (PAGE) will be used to make this qualitative comparison, with target band intensity as the standardized metric.

After optimizing reaction conditions, the primer sets for the other DNA species (*P. falciparum*, and *S. tyhpi*) will be interrogated for efficiency and specificity. Again, we will assess amplification efficiency for each primer set by quantifying the amount of target produced in 10, 30, and 90 min isothermal amplification (via PAGE). Specificity will be assessed by performing PCR with a primer set for a given species using human genomic DNA spiked with 5000 copies of genomic species for all other species. Specific robust reactions will show amplification of only the target sequence. Of the 5 primer sets designed for each species, we will use the three most efficient sets that show good specificity.

Figure 35:
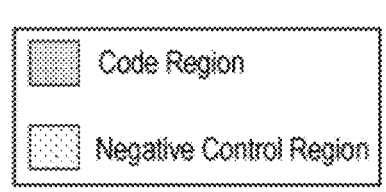
FIG. 35 illustrates exemplary design of barcoded gel particles for species-specific amplicon quantification.
Figure 35:
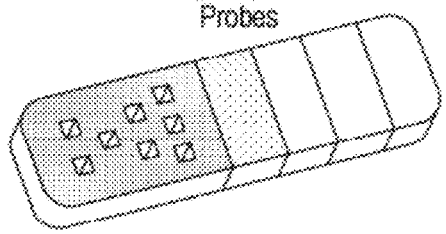
Figure 35:
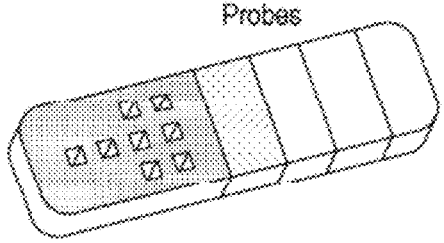
Figure 35:
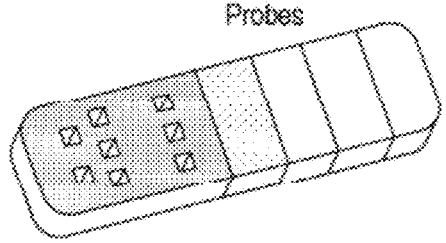

The three primer sets for each species will be used in a multiplexed amplification assay with one target present at a time. For multiplexed reactions, target amplification will be accomplished using a fluorescent forward primer, as shown in FIG. 34. For each reaction, the amplification product will be quantified using a 30 min incubation with barcoded gel particles bearing probes for each amplicon (FIG. 35). The DNA probes for each particle will be designed to span the reverse primer and internal region, and will be 3' capped to avoid extension as shown in FIG. 35. This design will allow for one-pot amplification/capture in subsequent studies.

Ideally, the fluorescent signals observed on the particles would be consistent over the 3 amplicons generated for each species. If significant differences in amplification/capture efficiency are observed for the multiplexed amplification, several reaction conditions will be varied in order to normalize the amount of amplicon captured on each particle probe region. First, the relative amounts of primers can be adjusted accordingly to alter the reaction kinetics. Second, primer length can be adjusted in order to change binding efficiency—this will likely affect the primer Tm and increase nonspecific amplification, and is therefore not desirable. Third, we have demonstrated that the rate of capture can be adjusted in a very predictable manner by changing the concentration of probe in each region of the particles.

After normalizing quantified signal for each species, we will perform one-pot assays where amplification and hybridization are completed in the same reaction. We will determine the effects that the particles have on the sensitivity and specificity of the primer sets. Iterative optimization of primer and probe sequences may be necessary, along with reaction temperature and duration. In the case of multiplexed, one-pot assays, we will image particles in both static (microscopy) and flow-through modes. We will monitor and compare sensitivity and reproducibility of the two approaches—these will be important considerations when designing the integrated system proposed in Example 17.

Reverse Transcription of Pathogen Genomic Material.

While the genomic DNA of *P. falciparum* and *S. typhi* can be directly amplified, the detection of HIV-1 and dengue virus, both ssRNA viruses, will require reverse transcription of genomic RNA to cDNA for amplification and analysis. This requires the addition of a reverse transcriptase enzyme into the isothermal amplification reaction. Reverse transcription has been successfully coupled with Helicase-Dependent Amplification, and isothermal RT-HAD kits are available commercially (IsoAmp®, NE Biolabs). This is the same kit being used in the previous studies.

We will start with a standard recommended protocol for RNA reverse transcription and cDNA amplification, using Phage MS2 as a model system for optimization. Using the 5 primer sets originally identified for Phage MS2, we will perform a similar optimization as done for DNA amplification. Once optimized, we will assess primer sets for the pathogen RNA targets, again quantifying amplification efficiency and specificity. Using the 3 best primer sets for each RNA species, we will perform a multiplex amplification for each. Again, amplicons will be quantified using encoded gel particles in both static and flow-through modes.

Optimization of One-Pot Assay for Multiplexed Pathogen DNA or RNA Detection.

Having independently optimized both multiplexed detection of DNA targets and RNA targets, we will combine these assays, and optimize for performance and speed. Using a human genomic DNA background, we will spike genomic material from each pathogen into samples at concentrations ranging from 1-100,000 copies. We will investigate and optimize primer concentrations, enzyme concentration, assay duration, and assay temperature. We will evaluate the performance of the assay for each pathogen, measuring specificity, limit of detection, and sensitivity at 100 copies/rxn. It is our goal to demonstrate 95% sensitivity for all pathogens at 100 copies/rxn with an assay time of 60 min.

Although the use of isothermal amplification with a one-step amplification/hybridization reaction capable of detecting both DNA and RNA species in a single sample is ideal, there are several alternative approaches which are perhaps less attractive, but more likely for success.

For example, if Helicase-Dependent Amplification (HDA) does not prove effective, several other isothermal methods will be investigated including Loop-Mediated Isothermal Amplification (LAMP), Strand-Displacement Amplification (SDA), and Nucleic Acid Sequence-Based Amplification (NASBA). Importantly, a NASBA-based assay has previously been approved by the FDA for the detection of HIV-1 and so would serve as an obvious next choice for RNA detection. Alternatively, standard PCR may be used. In fact, microfluidic methods for PCR amplification are becoming very common so the use of this technique would not be out of the question. Also, if the detection of RNA pathogens (which required reverse transcription) and DNA pathogens in the same tube gives rise to insurmountable complications, these assays can be separated into two distinct tests.

In some embodiments, as an alternative approach to one-pot assays, two-step amplification/hybridization can be use in accordance with the present invention. If the particles interfere in any way with the amplification process, it may be necessary to perform amplification and hybridization separately. Envisioning a cartridge-based system in which this technology can be implemented, this assay can still be accomplished on-chip but will require slightly more sophisticated liquid handling. Although this is not the ideal situation, it is manageable and can feasibly meet the needs of diagnostics in the developing world.

Example 16

Validation of One-pot Assay for Multiplexed Pathogen Detection

After developing a one-pot assay for the multiplexed detection of pathogens in Example 15, we will validate it using clinically-relevant samples and benchmark it against pathogen-specific assays developed for quantitative PCR, the current gold standard for nucleic-acid based pathogen diagnostics. This objective will be important in demonstrating the clinical utility of this assay.

We will obtain a representative set of clinically-relevant samples from several collaborators. Without being bound to any particular theory, it is believed that the samples we obtain will be well-preserved. This is especially important for RNA detection as RNA is rapidly degraded by RNase activity. If the available sample volume permits, we will perform quality control via DNA/RNA sizing with an Agilent Bioanalyzer. Another assumption is that these samples will be representative of the samples that would be obtained in the field when our technology is deployed. Ideally, the samples would span a broad range of pathogen load, and states of patients' immunologic response.

There are several stages in the validation of our assay. Initially, we will investigate various methods for purifying nucleic acids from whole blood and determine compatibility with our assay for each pathogen. This will be important in determining which purification technologies could be integrated with our platform after this initial research project is completed. We will ideally be able to select one isolation technique that performs well for all pathogens, and use it for all validation tests. We will purify nucleic acids from the clinical samples (blood or plasma) provided by our collaborators and test the samples using our one-pot test and also commercially-available pathogen qPCR kits. This will allow a direct benchmark of our assay against the current state-of-the art. Details for each part of the validation process are given below.

Assessment of Nucleic Acid Purification Techniques. There are several methods for extracting nucleic acids from whole blood, plasma, or serum. Most of the kits are specific for either RNA or DNA, though a few kits can be used to extract both. We will investigate several commercially-available kits including:

DNA Extraction: QIAamp Blood DNA Mini Extraction Kit (QIAGEN), Genomic DNA Extraction Kit (Bioneer), Extract-N-Amp Blood PCR Kits (Sigma).

RNA Extraction: QIAmp Viral RNA Mini Extraction Kit (QIAGEN), Viral RNA Extraction Kit (Bioneer).

Simultaneous Extraction of DNA and RNA: QIAamp MinElute Virus Spin Kit, QIAamp UltraSens Virus Kit, NucleoSpin Virus Kit (Macherey-Nagel).

Clearly, the optimal mode for multiplexed assays is the use of a single extraction method for parallel isolation of pathogen DNA and RNA. We will devote a significant amount of effort into identifying and optimizing a method for dual nucleic acid extraction that functions well with our one-pot assay. To assess compatibility, we will use well-characterized clinical samples containing each pathogen and perform extraction with each of the kits. The samples will subsequently be assessed with our one-pot assay and also validated using qPCR kits specifically designed for each pathogen.

Assay on Clinical Samples with Direct Comparison to qPCR.

Nucleic acids from clinical samples (at least 30 for each pathogen type) will be purified using the optimal method determined in the previous section. We will perform a one-pot, multiplexed assay for the detection of pathogens in each sample and compare our results to qPCR assays specifically designed for each pathogen. For three of the four pathogens being investigated, there are several qPCR kits available. At the time we reach this objective, we will select the kit that has shown best performance and has received certification for diagnostic testing:

Dengue: Primer Design, Ltd. and Genome Diagnostics
Malaria: Primer Design, Ltd., AccuPower, and Genome Diagnostics
HIV-1: Primer Design, Ltd., and Genome Diagnostics
Typhoid: To our knowledge, there is no commercially-available qPCR assay for *S. tyhpi*. There is a multiplex PCR-based approach by Kumar et al. that will be used in place of qPCR if no test has been developed by the time we reach this objective of the project.

For relative comparison of sensitivity, we will also make serial dilutions of a representative sample for each pathogen type and analyze them using both our assay and the qPCR standard. A strong correlation of our assay results with the state-of-the art is important for validation. If our assay performs less desirably than expected, we will troubleshoot the assay by re-evaluating the regions targeted, primer design, and assay conditions. We will work closely with our collaborators for guidance in resolving any issues.

Example 17

Development of a Proof-of-Concept Integrated System

After successfully developing an assay, it is important to begin conceptualizing methods for the assay to be implemented on chip. For this reason, we will explore methods for performing one-pot assay and analyzing particles in a single chamber. This will require the development of an integrated system capable of precise temperature control with capabilities for fluorescence imaging for static particle analysis or rapid signal acquisition for flow-through analysis. This system will allow periodic analysis of the particles to assess the progress of reaction. As a significant improvement over end-point analysis, we believe that this method of analysis can be calibrated to provide precise quantitative analysis of pathogen load. In this Example, we aim to develop an integrated system to perform rapid, one-pot assays with the ability to accurately quantify pathogen nucleic acids.

As the simplest initial approach, we will use a commercially-available temperature-controlled cell perfusion chamber with static imaging on a microscope. We will perform several studies to evaluate the use of a one-pot chamber reaction for pathogen detection and also assess the feasibility of performing quantitative analysis with periodic image analysis. After successful implementation, we will integrate the heated flow chamber into a stand alone device with an LED illumination source and a CCD camera to acquire images. This represents an important step toward developing a cartridge-based system that would ultimately be deployed in developing countries. More details on the specific activities for this objective are given below.

One-Pot Assays in a Heated Flow Cell.

We will use a commercially-available heated flow cell, similar to those sold by Bioptechs. These flow cells feature (1) customizable channel design, (2) multiple interfaces for sample introduction, (3) precise temperature control with +/−0.2° C. stability, and (4) a standard design for mounting on any microscope. Initially, we will utilize a simple rectangular flow chamber for assay and analysis. We will premix the reaction mixture to include the sample of interest, isothermal amplification reagents, and ~50 particles for each of the four pathogens and two controls. The device will be pre-heated to the isothermal amplification temperature (~55° C.) and the reaction mixture will be introduced into the reaction chamber. Using a standard inverted microscope with a 5× objective (for large field of view), single excitation color, and single detection color, particles will be imaged throughout the course of amplification, likely every 5 minutes. Each image will be analyzed to estimate the amount each amplicon generated, based on probe-region fluorescence. After 60 min reaction, this dynamic data will be used to estimate the amount of template initially present. For a proof-of-concept, we will use the two controls, λ-phage DNA and Phage MS2, in order to characterize system performance and ability to provide quantitative data.

Design and Construction of an Integrated Assay/Scanning System. After successful implementation of a microscope-based system, we will integrate the flow cell into a custom optical system. We will utilize a homogeneous LED illumination, a low-magnification lens, and a CCD chip. The LED array, CCD, and heated flow cell will be interfaced with a laptop computer for control, image acquisition, and analysis. The unit will be thoroughly tested, and results will be compared to those obtained previously in this project. We will re-evaluate the sensitivity and specificity of detection for each pathogen using this setup. We will also investigate the quantitative dynamic range of the system by spiking in targets from 1-1M copies. We take measures to ensure that performance is not compromised in an integrated system.

All literature and similar material cited in this application, including, patents, patent applications, articles, books, treatises, dissertations and web pages, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The section headings used herein are for organizational purposes only and are not to be construed as limiting the subject matter described in any way.

Other Embodiments and Equivalents

While the present disclosures have been described in conjunction with various embodiments and examples, it is not intended that they be limited to such embodiments or examples. On the contrary, the disclosures encompass various alternatives, modifications, and equivalents, as will be appreciated by those of skill in the art. Accordingly, the descriptions, methods and diagrams of should not be read as limited to the described order of elements unless stated to that effect.

Although this disclosure has described and illustrated certain embodiments, it is to be understood that the disclosure is not restricted to those particular embodiments. Rather, the disclosure includes all embodiments that are functional and/or equivalents of the specific embodiments and features that have been described and illustrated.

We claim:

1. A method of encoding a particle comprising:
   a. providing a particle comprising two or more encoding regions, each encoding region bearing one or more anchor oligonucleotides and wherein the encoding regions are separated by an inert region;
   b. providing a plurality of labeled and unlabeled encoding adapters at a ratio to achieve a desired detectable signal level in each encoding region, wherein each individual encoding adapter is designed to specifically bind an individual anchor oligonucleotide and wherein a labeled encoding adapter comprises a detectable moiety;
   c. incubating the particle with the plurality of labeled and unlabeled encoding adapters under conditions that allow the labeled and unlabeled encoding adapters to bind their corresponding anchor oligonucleotides in the two or more encoding regions, thereby encoding the substrate by the desired detectable signal level in the each encoding region.

2. The method of claim 1, wherein the method further comprises a step of coupling the individual encoding adapter to its corresponding anchor oligonucleotide.

3. The method of claim 1, wherein the anchor oligonucleotide is a single-stranded polynucleotide template.

4. The method of claim 3, wherein individual single-stranded polynucleotide template and individual encoding adapter are both linear.

5. The method of claim 3, wherein
   individual single-stranded polynucleotide template forms a hairpin structure and individual encoding adapter does not form a hairpin structure; or
   individual single-stranded polynucleotide template does not form a hairpin structure and individual single-stranded encoding adapter forms a hairpin structure.

6. The method of claim 1, wherein the labeled encoding adapters are labeled with distinct detectable moieties.

7. The method of claim 1, wherein the plurality of labeled and unlabeled encoding adapters comprise one or more sets of labeled and unlabeled encoding adapters, wherein, in each set, the labeled and unlabeled encoding adapters have substantially identical sequences.

8. The method of claim 1, wherein the particle further comprises one or more probe regions that are distinct from the one or more encoding regions.

9. The method of claim 1, wherein the particle is a hydrogel particle.

10. The method of claim 1, wherein the individual anchor oligonucleotide comprises at least 10 bases.

11. The method of claim 1, wherein the each individual encoding adapter is DNA or RNA.

12. The method of claim 1, wherein the each individual encoding adapter comprises up to 30 nucleotides.

13. The method of claim 1, wherein the detectable moiety is selected from fluorophores, chromophores, radioisotopes, quantum dots, nanoparticles and/or intercalating DNA/RNA dyes.

14. The method of claim 1, wherein a signal provided by at least one labeled encoding adapter is used to determine the orientation of the substrate.

15. The method of claim 1, wherein a signal provided by at least one labeled encoding adapter is used to normalized the desired detectable signal level.

16. The method of claim 1, wherein the desired detectable signal level in the each encoding region is distinguishable at multiple levels.

17. The method of claim 16, wherein the desired detectable signal level in the each encoding region is distinguishable for up to 10 levels.

18. The method of claim 16, wherein the desired detectable signal level in the each encoding region is distinguishable for up to 20 levels.

19. The method of claim 2, wherein the step of coupling comprises enzymatic coupling or chemical coupling.

20. The method of claim 18, wherein the enzymatic couple is ligation.

21. The method of claim 5, wherein the method further comprises, after the incubating step, a step of ligation such that the individual single-stranded polynucleotide template is covalently coupled with the individual single-stranded encoding adapter bound to the template.

22. A method of encoding a hydrogel particle, comprising:
   a. providing a hydrogel particle comprising two or more encoding regions, each encoding region bearing one or more anchor oligonucleotides, wherein each individual anchor oligonucleotide is a single-stranded polynucleotide template that forms a hairpin structure and wherein the encoding regions are separated by an inert region;
   b. providing a plurality of labeled and unlabeled encoding adapters at a ratio to achieve a desired detectable signal level in each encoding region, wherein each individual encoding adapter is designed to specifically bind an individual anchor oligonucleotide and wherein a labeled encoding adapter comprises a detectable moiety;
   c. incubating the hydrogel particle with the plurality of labeled and unlabeled encoding adapters under conditions that allow the labeled and unlabeled encoding adapters to bind their corresponding anchor oligonucleotides in the two or more encoding regions, thereby encoding the substrate by generating the desired detectable signal level in the each encoding region.

* * * * *